US011688517B2

(12) United States Patent
Binder et al.

(10) Patent No.: US 11,688,517 B2
(45) Date of Patent: Jun. 27, 2023

(54) MULTIPLE OPERATING POINT FALSE POSITIVE REMOVAL FOR LESION IDENTIFICATION

(71) Applicant: Guerbet, Villepinte (FR)

(72) Inventors: Thomas Binder, Paris (FR); Giovanni John Jacques Palma, Chaville (FR)

(73) Assignee: Guerbet, Villepinte (FR)

( * ) Notice: Subject to any disclaimer, the term of this patent is extended or adjusted under 35 U.S.C. 154(b) by 213 days.

(21) Appl. No.: 17/085,005

(22) Filed: Oct. 30, 2020

(65) Prior Publication Data

US 2022/0139552 A1  May 5, 2022

(51) Int. Cl.
*G16H 50/20* (2018.01)
*G16H 30/20* (2018.01)
(Continued)

(52) U.S. Cl.
CPC ............ *G16H 50/20* (2018.01); *A61B 6/032* (2013.01); *A61B 6/50* (2013.01); *A61B 6/5211* (2013.01);
(Continued)

(58) Field of Classification Search
CPC ........ G16H 30/40; G16H 50/20; G16H 50/50; G16H 40/20; G06T 2207/30096
See application file for complete search history.

(56) References Cited

U.S. PATENT DOCUMENTS 6,138,045 A   10/2000  Kupinski
6,366,800 B1   4/2002  Vining et al.
(Continued)

FOREIGN PATENT DOCUMENTS

CN   109544534 A   3/2019
CN   109635835 A   4/2019
(Continued)

OTHER PUBLICATIONS

Song, Bowen, et al. "ROC operating point selection for classification of imbalanced data with application to computer-aided polyp detection in CT colonography." International journal of computer assisted radiology and surgery 9.1 (2014): 79-89. (Year: 2014).*
(Continued)

*Primary Examiner* — Linh Giang Le
*Assistant Examiner* — Constantine Siozopoulos
(74) *Attorney, Agent, or Firm* — Stephen J. Walder, Jr.

(57) ABSTRACT

A false positive removal engine is provided. The false positive removal engine receives detected objects in one or more images. A machine learning classifier computer model, configured with first operational parameters to implement a first operating point, processes the received input to classify each detected object as being a true positive or a false positive to generate a first set of object classifications. If the first set is empty, the false positive removal engine outputs the first set as a filtered list of objects; otherwise the ML classifier computer model is configured with second operational parameters to implement a second operating point, different from the first operating point, which then processes the received input to classify each detected object and generate a second set of objects classified as true positive, which is output by the false positive removal engine as the filtered list of objects.

20 Claims, 17 Drawing Sheets

(51) Int. Cl.
  *G16H 30/40* (2018.01)
  *G16H 70/60* (2018.01)
  *G06F 16/55* (2019.01)
  *A61B 6/03* (2006.01)
  *A61B 6/00* (2006.01)
  *G06N 20/00* (2019.01)
  *G06F 18/21* (2023.01)
  *G06F 18/2431* (2023.01)

(52) U.S. Cl.
  CPC ............ *G06F 16/55* (2019.01); *G06F 18/217* (2023.01); *G06F 18/2431* (2023.01); *G06N 20/00* (2019.01); *G16H 30/20* (2018.01); *G16H 30/40* (2018.01); *G16H 70/60* (2018.01)

(56) References Cited

U.S. PATENT DOCUMENTS

| | | | |
|---|---|---|---|
| 7,457,444 | B2 | 11/2008 | Geiger et al. |
| 8,023,734 | B2 | 9/2011 | Jolly et al. |
| 8,532,356 | B2 | 9/2013 | Kiraly et al. |
| 9,117,259 | B2 | 8/2015 | Liu et al. |
| 10,049,451 | B2 | 8/2018 | Fisher |
| 10,147,223 | B2 | 12/2018 | Kim et al. |
| 10,580,131 | B2 | 3/2020 | Mazo |
| 10,636,173 | B1 | 4/2020 | Beach et al. |
| 11,188,773 | B2 | 11/2021 | Gao et al. |
| 2003/0144585 | A1 | 7/2003 | Kaufman et al. |
| 2003/0167001 | A1 | 9/2003 | Allain et al. |
| 2006/0210133 | A1 | 9/2006 | Krishnan et al. |
| 2008/0044072 | A1 | 2/2008 | Kiraly et al. |
| 2009/0092302 | A1 | 4/2009 | Kubota et al. |
| 2009/0175531 | A1 | 7/2009 | Boroczky et al. |
| 2009/0226057 | A1 | 9/2009 | Mashiach et al. |
| 2010/0067754 | A1 | 3/2010 | Collins et al. |
| 2011/0125734 | A1 | 5/2011 | Duboue et al. |
| 2011/0274314 | A1 | 11/2011 | Yang et al. |
| 2012/0070055 | A1 | 3/2012 | Liu et al. |
| 2012/0250933 | A1 | 10/2012 | Porikli et al. |
| 2013/0114904 | A1 | 5/2013 | Chang et al. |
| 2013/0032271 | A1 | 12/2013 | Notte |
| 2014/0037170 | A1 | 2/2014 | Sekiguchi et al. |
| 2014/0044328 | A1 | 2/2014 | Matsuda et al. |
| 2014/0307930 | A1 | 10/2014 | Lee |
| 2015/0030219 | A1 | 1/2015 | Madabhushi et al. |
| 2015/0043799 | A1 | 2/2015 | Zhan et al. |
| 2015/0153180 | A1 | 6/2015 | Ettinger et al. |
| 2015/0230773 | A1 | 8/2015 | Cho et al. |
| 2015/0254842 | A1 | 9/2015 | Brown |
| 2017/0084060 | A1 | 3/2017 | Bal et al. |
| 2017/0270664 | A1 | 9/2017 | Hoogi et al. |
| 2018/0046934 | A1 | 2/2018 | Aravkin et al. |
| 2018/0103892 | A1 | 4/2018 | Kaur et al. |
| 2018/0144243 | A1 | 5/2018 | Hsieh et al. |
| 2018/0189953 | A1 | 7/2018 | Nie et al. |
| 2018/0247407 | A1 | 8/2018 | Park et al. |
| 2018/0247414 | A1 | 8/2018 | Novikov et al. |
| 2019/0333225 | A1 | 10/2019 | Wan et al. |
| 2019/0355117 | A1 | 11/2019 | Tan et al. |
| 2020/0012904 | A1 | 1/2020 | Zhao et al. |
| 2020/0085382 | A1* | 3/2020 | Taerum ................ A61B 5/7267 |
| 2020/0160176 | A1 | 5/2020 | Mehrasa et al. |
| 2020/0160945 | A1 | 5/2020 | Lyman et al. |
| 2020/0184708 | A1 | 6/2020 | Petkov et al. |
| 2020/0193603 | A1 | 6/2020 | Golden et al. |
| 2020/0245960 | A1 | 8/2020 | Richter et al. |
| 2020/0315587 | A1 | 10/2020 | Toporek et al. |
| 2020/0380675 | A1 | 12/2020 | Golden et al. |
| 2020/0391053 | A1 | 12/2020 | Koyama |
| 2020/0401843 | A1 | 12/2020 | Peng |
| 2021/0035296 | A1 | 2/2021 | Mahrooghy et al. |
| 2021/0065877 | A1 | 3/2021 | Chen |
| 2021/0110534 | A1* | 4/2021 | Yu ........................ G06T 7/0012 |
| 2021/0153838 | A1 | 5/2021 | Nien et al. |
| 2021/0219936 | A1 | 7/2021 | Chu et al. |
| 2021/0233645 | A1 | 7/2021 | Morard et al. |
| 2021/0248736 | A1 | 8/2021 | Kamen et al. |
| 2021/0255363 | A1 | 8/2021 | Liu et al. |
| 2021/0304002 | A1 | 9/2021 | George et al. |
| 2022/0138931 | A1 | 5/2022 | Palma et al. |
| 2022/0138932 | A1 | 5/2022 | Bonakdar Sakhi et al. |
| 2022/0138933 | A1 | 5/2022 | Wang et al. |
| 2022/0138956 | A1 | 5/2022 | Palma et al. |
| 2022/0139531 | A1 | 5/2022 | Wang et al. |

FOREIGN PATENT DOCUMENTS

| | | |
|---|---|---|
| CN | 109961448 A | 7/2019 |
| CN | 110600122 A | 12/2019 |
| CN | 110827310 A | 2/2020 |
| CN | 110929789 A | 3/2020 |
| CN | 111402268 A | 7/2020 |
| CN | 112241766 A | 1/2021 |
| WO | WO2019/103912 A2 | 5/2019 |
| WO | WO-2022051290 A1 * | 3/2022 |

OTHER PUBLICATIONS

List of IBM Patents or Patent Applications Treated as Related, Jun. 9, 2022, 2 pages.

International Search Report and Written Opinion dated Jan. 26, 2022 for International Application No. PCT/CN2021/126662, 10 pages.

List of IBM Patents or Patent Applications Treated as Related (Appendix P), Jan. 19, 2021, 2 pages.

Sitek, Arkadiusz et al., "Method of Determining Contrast Phase of a Computerized Tomography Image", filed Jul. 13, 2020, U.S. Appl. No. 16/926,880.

Abraham, Nabila et al., "A Novel Focal Tversky Loss Function With Improved Attention U-Net for Lesion Segmentation", https://arxiv.org/abs/1810.07842v1, Oct. 2018, 5 pages.

Almotairi, Sultan et al., "Liver Tumor Segmentation in CT Scans Using Modified SegNet", Sensors 2020, 20, 1516; doi: 10.3390/s20051516, Mar. 10, 2020, 13 pages.

Bellver, Miriam et al., "Detection-aided liver lesion segmentation using deep learning", Computer Vision and Pattern Recognition; Machine Learning 4 Health Workshop from 31st Conference on Neural Information Processing Systems (NIPS 2017), Dec. 4-9, 2017, submitted version arXiv:1711.11069v1 [cs.CV], Nov. 29, 2017, 5 pages.

Beucher, Serge et al., "The Morphological Approach to Segmentation: The Watershed Transfonnation", Mathematical Morphology in Image Processing 34 (1993, 49 pages.

Chan, Tony F. et al., "Active Contours Without Edges", IEEE Transactions on Image Processing, vol. 10, No. 2, Feb. 2001, 12 pages.

Dong, Xin et al., "Liver Cancer Detection Using Hybridized Fully Convolutional Neural Network Based on Deep Learning Network", IEEE Access, Special Section on Deep Learning Algorithms for Internet of Medical Things, vol. 8, 2020, 10 pages.

Gotra, Akshat et al., "Liver Segmentation: Indications, Techniques and Future Directions", Springer Link, Insights into Imaging, Jun. 2017, 16 pages.

High, Rob, "The Era of Cognitive Systems: An Inside Look at IBM Watson and How it Works", IBM Corporation, Redbooks, Dec. 12, 2012, 16 pages.

Hoogi, Assaf et al., "A Fully-Automated Pipeline for Detection and Segmentation of Liver Lesions and Pathological Lymph Nodes", arXiv:1703.06418v1 [cs.CV], Mar. 19, 2017, 4 pages.

Xia, Kaijian et al., "Liver Semantic Segmentation Algorithm Based on Improved Deep Adversarial Networks in combination of Weighted Loss Function on Abdominal CT Images", IEEE Access, 2017, 11 pages.

Yuan, Michael J. , "Watson and healthcare", IBM Corporation, developerWorks, http://www.ibm.com/developerworks/industry/library/ind-watson/, Apr. 12, 2011, pp. 1-14.

Al-Azawi, Razi J. et al., "Enhanced Algorithm of Superpixel Segmentation Using Simple Linear Iterative Clustering", 2019 12th

(56) References Cited

OTHER PUBLICATIONS

International Conference on Developments in eSystems Engineering (DeSE), pp. 160-163, Jul. 2019.

Sahin, Ismet et al., "Tumor Spheres Quantification with Smoothed Euclidean Distance Transform", Journal of Molecular Imaging & Dynamics, vol. 8, Issue 1, 9 pages, Jul. 2018.

Yu, Zeyun et al., "Detecting Circular and Rectangular Particles Based on Geometric Feature Detection in Electron Micrographs", Journal of Structural Biology, vol. 145, Issues 1-2, pp. 168-180, Oct. 2003.

* cited by examiner

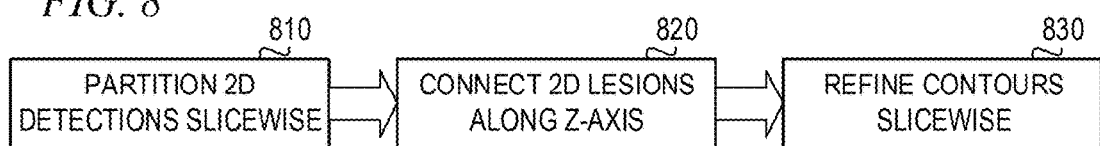
FIG. 8
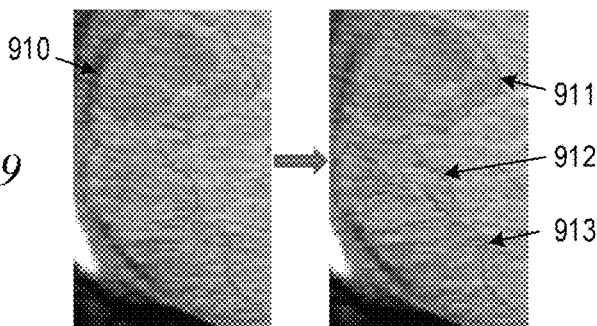
FIG. 9
FIG. 10A
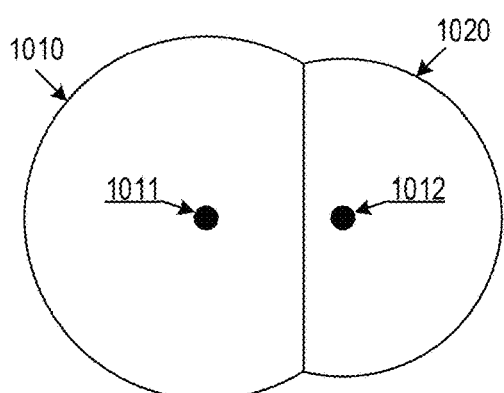
FIG. 10C
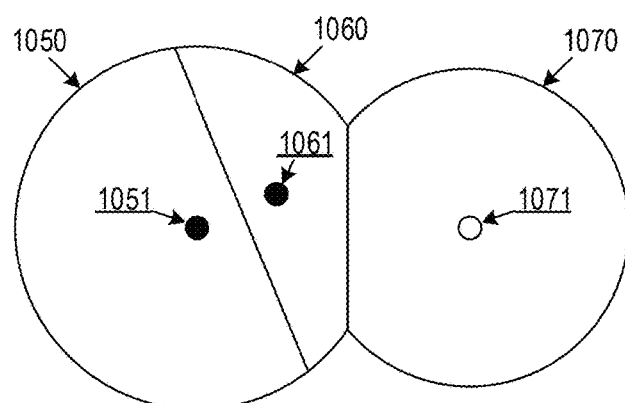
FIG. 10B
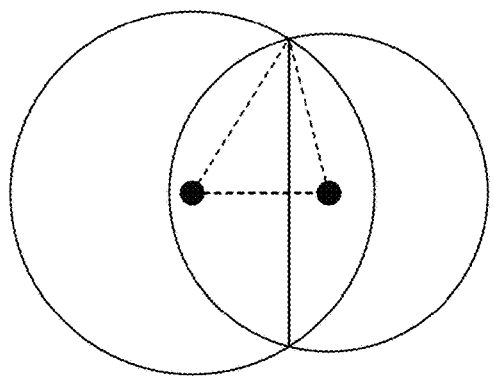
FIG. 10D
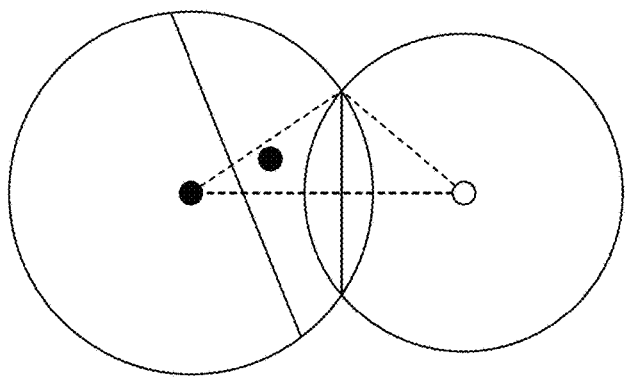

MULTIPLE OPERATING POINT FALSE POSITIVE REMOVAL FOR LESION IDENTIFICATION

BACKGROUND

The present application relates generally to an improved data processing apparatus and method and more specifically to mechanisms for providing multiple operating point false positive removal for lesion identification.

Liver lesions are groups of abnormal cells in a biological entity's liver, and may also be called a mass or tumor. Noncancerous, or benign, liver lesions are common and do not spread to other areas of the body. Such benign liver lesions do not generally cause any health issues. However, some liver lesions form as a result of cancer. Patients with certain medical conditions may be more likely to have cancerous liver lesions than other patients. These medical conditions include hepatitis B or C, cirrhosis, iron storage disease (hemochromatosis), obesity or exposure to toxic chemicals such as arsenic or aflatoxin, for example.

Liver lesions are typically only identifiable by having a medical imaging test, such as an ultrasound, magnetic resonance image (MRI), computerized tomograph (CT), or positron emission tomography (PET) scan, for example. Such medical imaging tests must be viewed by a human medical imaging subject matter expert (SME) who must use their own knowledge and expertise as well as human ability to see patterns in images, to determine if the medical imaging test shows any lesions. If a potentially cancerous lesion is identified by the human SME, the patient's physician may have a biopsy performed to determine if the lesion is cancerous.

Abdominal contrast enhanced (CE) CT is the current standard in assessment of various abnormalities (e.g., lesions) in the liver. These lesions may be evaluated by human SMEs as malignant (hepatocellular carcinoma, cholangiocarcinoma, angiosarcoma, metastasis, and other malignant lesions) or benign (hemangioma, focal nodular hyperplasia, adenoma, cyst or lipoma, granuloma, etc.). The manual evaluation of such images by human SMEs is important to guiding subsequent interventions. Many times, in order to properly evaluate lesions in a CE CT, a multi-phase study is conducted where the multi-phase study provides medical imaging of different stages of enhancement of healthy liver parenchyma and comparison to enhancement of lesions to determine differences detection. The human SME can then determine a diagnosis of the lesions based on these differences.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions executed by the at least one processor to implement a false positive removal engine for removing falsely identified objects in a listing of objects input data set. The method comprises receiving, by the false positive removal engine, a received input comprising a listing of detected objects in one or more images of an input volume of images, and configuring, by the false positive removal engine, at least one machine learning classifier computer model with first operational parameters to implement a first operating point for the at least one machine learning classifier computer model and thereby generate a first operating point configured model. The method also comprises configuring, by the false positive removal engine, the at least one machine learning classifier computer model with second operational parameters to implement a second operating point, different from the first operating point, for the at least one machine learning classifier computer model and thereby generate a second operating point configured model. In addition, the method comprises processing, by the first operating point configured model, the received input to classify each detected object in the listing of objects as to whether or not the detected object is a true positive or a false positive to thereby generate a first set of detected objects classified as true positive. Moreover, the method comprises determining, by logic of the false positive removal engine, whether the first set is empty, and in response to the first set being empty, outputting, by the false positive removal engine, the first set as a filtered list of objects. Furthermore, the method comprises, in response to the first set not being empty, processing, by the second operating point configured model, the received input to classify each detected object in the listing of objects as to whether or not the detected object is a true positive or a false positive to thereby generate a second set of detected objects classified as true positive and outputting, by the false positive removal engine, the second set of detected objects as the filtered list of objects. By providing a false positive removal engine that uses multiple operating points for a machine learning classifier computer model, improved false positive removal is made possible so as to eliminate object detections in images that are not actual objects of interest, e.g., lesions in anatomical structures.

In some illustrative embodiments, the first operating point is a group level operating point that has a relatively higher specificity than the second operating point, and the first set of operational parameters are operational parameters optimized to minimize group level false positives generated by the at least one machine learning classifier computer model. In some illustrative embodiments, the second operating point is an element level operating point that has a relatively higher sensitivity than the first operating point, and the second set of operational parameters are operational parameters optimized to increase a number of element level true positives generated by the at least one machine learning classifier computer model. By providing two different operating points in which differing levels of false positive retention are acceptable, a balanced false positive removal is achieved that balances considerations of maintaining as many true positives at a group level while minimizing false positives at the element level.

In some illustrative embodiments, the first operating point is selected by analyzing a group level receiver operating characteristic (ROC) curve plotting group level object detection sensitivity versus group level object detection specificity, to select a point along the group level ROC curve in which a pairing of object detection sensitivity and object detection specificity results in a predetermined percentage of true positive object detections being maintained in the first set of detected objects. In some illustrative embodiments, the second operating point is selected by analyzing an element level receiver operating characteristic (ROC) curve plotting object detection sensitivity versus object detection specificity, to select a point along the element level ROC curve having an object detection sensitivity that is higher than an object detection sensitivity corresponding to the first operating point, and provides at least a predetermined level of object detection specificity corresponding to a performance of the at least one machine learning classifier computer model. Again, the selection of different operating points in this manner balances false positive removal taking into consideration the maintaining as many true positives at a group level while minimizing false positives at the element level.

In some illustrative embodiments, the at least one machine learning classifier computer model comprises a first machine learning classifier computer model and a second machine learning classifier computer model. Moreover, configuring at least one machine learning classifier computer model with first operational parameters to implement a first operating point may comprise performing machine learning training of the first machine learning classifier computer model based on the first operating point. Configuring at least one machine learning classifier computer model with second operational parameters to implement a second operating point may comprise performing machine learning training of the second machine learning classifier computer model based on the second operation point. In this way, rather than having to reconfigure a single machine learning model with different operating points, two machine learning classifier computer models may be employed.

In some illustrative embodiments, the objects are lesions and the false positive removal engine is a stage of computer logic in a lesion detection and classification artificial intelligence (AI) pipeline comprising a plurality of trained machine learning computer models. The received input may be received from a lesion segmentation logic stage of the AI pipeline that implements an ensemble of at least one trained machine learning computer model that generates the listing of objects. Thus, the false positive removal mechanisms may be employed with medical imaging analysis and the removal of lesions in a listing of lesions detected by lesion detection mechanisms that are determined to not be actual lesions.

In some illustrative embodiments, the plurality of trained machine learning computer models of the AI pipeline comprises one or more first machine learning computer models of the AI pipeline that process an input volume of medical images to detect lesions present in the medical images of the input volume which correspond to an anatomical structure of interest, and one or more second machine learning computer models of the AI pipeline that processes the detected lesions to perform lesion segmentation and combining of lesion contours of different images in the input medical image associated with a same lesion, to generate the listing of lesions and corresponding lesion contours. In this way, the false positive removal mechanisms may be used with listings of lesions generated through a AI pipeline employing segmentation mechanisms and mechanisms for combining contours of lesions for improved lesion detection. The false positive removal improves the resulting listing of lesions by minimizing the number of false positives present in the listing of lesions.

In some illustrative embodiments, the plurality of trained machine learning computer models comprise one or more machine learning computer models that process the filtered listing of lesions output by the false positive removal engine to classify the lesions in the listing of lesions into one or more predetermined classes of lesions corresponding to the anatomical structure of interest. In this way, the false positive removal may be used to improve the listing of lesions and classification of lesions so as to provide a more accurate basis for identifying lesions that should be considered by medical personnel in treating a patient. The classification identifies the type of lesion, e.g., benign, malignant, etc., so that the medical personnel attention can be directed to lesions that pose potential threat to the patient's medical condition.

In some illustrative embodiments, the anatomical structure of interest is a human liver. As noted in the description, lesion detection in the human liver is a difficult task especially in cases where lesions are not necessarily present in the center mass of the liver. The illustrative embodiments provide mechanisms that provide accurate lesion detection in the human liver.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 8 depicts a block diagram of the aspects of lesion segmentation in accordance with one illustrative embodiment;

FIG. 9 depicts a result of lesion detection and slice-wise partitioning in accordance with one illustrative embodiment;

FIGS. 10A-10D illustrate seed positioning in accordance with one illustrative embodiment;

DETAILED DESCRIPTION

Figure 1:
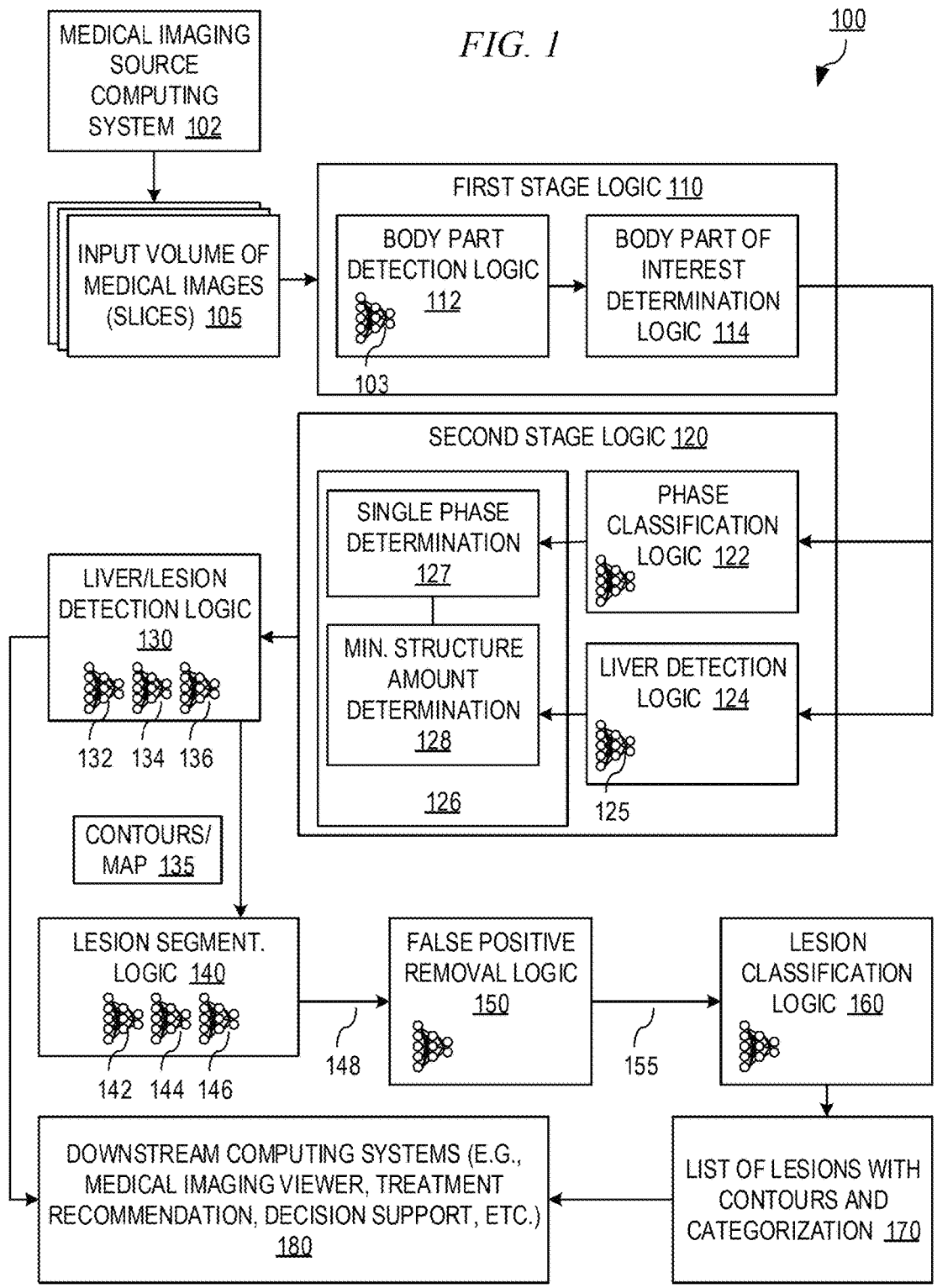
FIG. 1 is an example block diagram of an AI pipeline implementing multiple specifically configured and trained ML/DL computer models to perform anatomical structure identification and lesion detection in input medical image data in accordance with one illustrative embodiment.

The detection of lesions, or groups of abnormal cells, is largely a manual process in modern medicine. As this is a manual process, it is fraught with sources of error due to human limitations with regard to individuals' abilities to detect portions of digital medical images that show such lesions, especially given the greater demands on such individuals to evaluate increasingly greater numbers of images in shorter amounts of time. While some automated image analysis mechanisms have been developed, there is still a need to improve such automated image analysis mechanisms to provide a more efficient and correct analysis of medical image data to detect lesions in an imaged anatomical structure, e.g., the liver or other organs.

The illustrative embodiments are specifically directed to an improved computing tool that provides automated computer driven artificial intelligence medical image analysis that is specifically trained, through machine learning/deep learning computer processes, to detect anatomical structures, detect lesions or other biological structures of interest in or associated with such anatomical structures, perform specialized segmentation of the detected lesions or other biological structures, perform false positive removal based on the specialized segmentation, and perform classification of the detected lesions or other biological structures, and provide the results of the lesion/biological structure detection to downstream computing systems to perform additional computer operations. The following description of the illustrative embodiments will assume embodiments specifically concerned with the mechanisms of the illustrative embodiments being specifically trained with regard to the liver lesions as the biological structure of interest, however the illustrative embodiments are not limited to such. Rather, those of ordinary skill in the art will recognize that the machine learning/deep learning based artificial intelligence mechanisms of the illustrative embodiments may be implemented with regard to a plethora of other types of biological structures/lesions in or associated with other anatomical structures represented in medical imaging data without departing from the spirit and scope of the present invention. Moreover, the illustrative embodiments may be described in terms of the medical imaging data being computed tomography (CT) medical imaging data, however the illustrative embodiments may be implemented with any digital medical imaging data from various types of medical imaging technologies including, but not limited to, positron emission tomography (PET) and other nuclear medicine imaging, ultrasound, magnetic resonance imaging (MRI), elastography, photoacoustic imaging, echocardiography, magnetic particle imaging, functional near-infrared spectroscopy, elastography, various radiography imaging including fluoroscopy, etc.

Overall, the illustrative embodiments provide an improved artificial intelligence (AI) computer pipeline comprising a plurality of specifically configured and trained AI computer tools, e.g., neural networks, cognitive computing systems, or other AI mechanisms that are trained based on a finite set of data to perform specific tasks. The configured and trained AI computer tools are each specifically configured/trained to perform a specific type of artificial intelligence processing of a volume of input medical images, represented as one or more collections of data and/or metadata that define the medical images captured by medical imaging technology. In general, these AI tools employ machine learning (ML)/deep learning (DL) computer models (or simply ML models) to perform tasks that, while emulating human thought processes with regard to the results generated, use different computer processes, specific to computer tools and specifically ML/DL computer models, which learn patterns and relationships between data that are representative of particular results, e.g., image classifications or labels, data values, medical treatment recommendations, etc. The ML/DL computer model is essentially a function of elements including the machine learning algorithm(s), configuration settings of the machine learning algorithm(s), features of input data identified by the ML/DL computer model, and the labels (or outputs) generated by the ML/DL computer model. By specifically tuning the function of these elements through a machine learning process, a specific ML/DL computer model instance is generated. Different ML models may be specifically configured and trained to perform different AI functions with regard to the same or different input data.

As the artificial intelligence (AI) pipeline implements a plurality of ML/DL computer models, it should be appreciated that these ML/DL computer models are trained through ML/DL processes for specific purposes. Thus, as an overview of the ML/DL computer model training processes, it should be appreciated that machine learning is concerned with the design and the development of techniques that take as input empirical data (such as medical image data), and recognizes complex patterns in the input data. One common pattern among machine learning techniques is the use of an underlying computer model M, whose parameters are optimized for minimizing the cost function associated to M, given the input data. For instance, in the context of classification, the model M may be a straight line that separates the data into two classes (e.g., labels) such that $M=a*x+b*y+c$ and the cost function would be the number of misclassified points. The learning process then operates by adjusting the parameters a, b, c such that the number of misclassified points is minimal. After this optimization phase (or learning phase), the model M can be used to classify new data points. Often, M is a statistical model, and the cost function is inversely proportional to the likelihood of M, given the input data. This is just a simple example to provide a general explanation of machine learning training and other types of machine learning using different patterns, cost (or loss) functions, and optimizations may be used with the mechanisms of the illustrative embodiments without departing from the spirit and scope of the present invention.

For purposes of anatomical structure detection and/or lesion detection (where lesions are "anomalies" in medical imaging data), a learning machine may construct a ML/DL computer model of normal structure representations, to detect data points in medical images that deviate from this normal structure representation ML/DL computer model. For example, a given ML/DL computer model (e.g., a supervised, un-supervised, or semi-supervised model) may be used to generate and report anomaly scores to another device, generate classification outputs indicating one or more classes to which an input is classified, probabilities or scores associated with the various classes, or the like. Example machine learning techniques that may be used to construct and analyze such ML/DL computer models may include, but are not limited to, nearest neighbor (NN) techniques (e.g., k-NN models, replicator NN models, etc.), statistical techniques (e.g., Bayesian networks, etc.), clustering techniques (e.g., k-means, etc.), neural networks (e.g., reservoir networks, artificial neural networks, etc.), support vector machines (SVMs), or the like.

The processor-implemented artificial intelligence (AI) pipeline of the illustrative embodiments generally includes one or both of machine learning (ML) and deep learning (DL) computer models. In some instances, one or the other of ML and DL can be used or implemented to achieve a particular result. Traditional machine learning can include or use algorithms such as Bayes Decision, Regression, Decision Trees/Forests, Support Vector Machines, or Neural Networks, among others. Deep learning can be based on deep neural networks and can use multiple layers, such as convolution layers. Such DL, such as using layered networks, can be efficient in their implementation and can provide enhanced accuracy relative to traditional ML techniques. Traditional ML can be distinguished from DL in general in that DL models can outperform classical ML models, however, DL models can consume a relatively larger amount of processing and/or power resources. In the context of the illustrative embodiments, references herein to one or the other of ML and DL can be understood to encompass one or both forms of AI processing.

With regard to the illustrative embodiments, the ML/DL computer models of the AI pipeline are executed, after configuration and training through ML/DL training processes, and perform complex computer medical imaging analysis to detect anatomical structures in input medical images and generate outputs specifically identifying target biological structures of interest (hereafter assumed to be liver lesions for purposes of description of example embodiments), their classifications, contours specifying where these target biological structures of interest (e.g., liver lesions) are present in the input medical images (hereafter assumed to be CT medical image data), and other information that aids human subject matter experts (SMEs), such as radiologists, physicians, and the like, in understanding a patient's medical condition from the viewpoint of the captured input medical images. Moreover, the outputs can be provided to other downstream computer systems to perform additional artificial intelligence operations, such as treatment recommendations and other decision support operations based on the classifications, contours, and the like.

Initially, the artificial intelligence (AI) pipeline of the illustrative embodiments receives an input volume of computed tomography (CT) medical imaging data and detects which part of the biological entity's body is depicted in the CT medical imaging data. A "volume" of medical images is a three-dimensional representation of the internal anatomical structure of the biological entity which is made up of stacks of two-dimensional slices, where the slices may be individual medical images captured by medical imaging technology. The stacks of slices may also be referred to as "slabs" and differ from the slices themselves in that the stacks represent a portion of the anatomical structure having a thickness, with the stacking of slices or slabs generating a three-dimensional representation of the anatomical structure.

For purposes of this description, it will be assumed that the biological entity is a human being, however the present invention may operate on medical images for various types of biological entities. For example, in veterinary medicine, the biological entity may be various types of small (e.g., pets such as dogs, cats, etc.) or large size animals (e.g., horses, cows, or other farm animals). For implementations where the AI pipeline is specifically trained for the detection of liver lesions, the AI pipeline determines if the input CT medical imaging data represents an abdominal scan being present in the CT medical imaging data and if not, the operation of the AI pipeline terminates with regard to the input CT medical imaging data as not being directed to the correct part or portion of the human body. It should be appreciated that there may be different AI pipelines according to the illustrative embodiments, trained to process input medical images for different portions of the body and different target biological structures, and the input CT medical images may be input to each of the AI pipelines, or routed to an AI pipeline based on a classification of the body part or portion of the body depicted in the input CT medical images, e.g., a classification of the input CT medical images as to body part or portion of the body represented in the input CT medical images may first be performed and then a corresponding trained AI pipeline may be selected from a plurality of trained AI pipelines of the type described herein, to process the input CT medical images. For purposes of the following description, a single AI pipeline trained to detect liver lesions will be described, but the extension of this to a suite or collection of AI pipelines will be apparent to those of ordinary skill in the art in view of the present description.

Assuming that the volume of input CT medical images comprises medical images of an abdominal portion of the human body (for purposes of liver lesion detection), further processing of the input CT medical images is performed in two primary stages which may be performed substantially parallel to each other and/or in sequence depending on the desired implementation. The two primary stages comprise a phase classification stage and an anatomical structure detection stage, e.g., liver detection stage in the case where the AI pipeline is configured to perform liver lesion detection.

The phase classification stage determines if the volume of input CT medical images comprises a single imaging phase or multiple imaging phases. The "phase" in medical imaging is an indication of a contrast agent uptake For example, in some medical imaging technologies, phases may be defined in terms of when a contrast medium is introduced into the biological entity which allows for the capturing of medical images that include capturing of the path of the contrast medium. For example, phases may include a pre-contrast phase, an arterial contrast phase, a portal/venous contrast phase and a delayed phase, with medical images being captured in any or all of these phases. Phases are usually related to timing after injection and to characteristics of the enhancement of structures within the images. Timing information can be taken into account to "sort" potential phase (e.g. a delayed phase will always be acquired after a portal phase) and to estimate the potential phase(s) of a given image. With regard to the use of characteristics of enhancement of structures within images, one example of using this type of information to determine phase is described in commonly assigned and co-pending U.S. patent application Ser. No. 16/926,880, filed Jul. 13, 2020, and entitled "Method of Determining Contrast Phase of a Computerized Tomography Image". Additionally, timing information can be used in conjunction with other information (sampling, reconstruction kernel, etc.) to pick up the best representative of each phase (a given acquisition can be reconstructed in several manners).

Once the images in the input volume are assigned or classified into their corresponding phases based on timing and/or characteristics of enhancement, it can be determined based on the phase classification whether the volume comprises images of a single phase (e.g., portal-venous phase present but no arterial) or multiphase exam (e.g., a portal-venous and arterial). If the phase classification indicates a single phase is present in the volume of input CT medical images, then further processing by the AI pipeline is performed as described hereafter. If multiple phases are detected, then the volume is not further processed by the AI pipeline. However, in some illustrative embodiments, while this filter of volumes based on single/multiple phases accepts only volumes with images from a single phase and rejects multi-phase volumes, in other illustrative embodiments the AI pipeline processing described herein may filter out images of a volume that are not classified into a target phase of interest, e.g., the portal-venous phase images in the volume may be maintained while filtering out images of the volume that are not classified as being part of the portal-venous phase to thereby modify the input volume to be a modified volume having only a subset of images classified into the target phase. Moreover, as discussed previously, different AI pipelines may be trained for different types of volumes and, in some illustrative embodiments, the phase classification of images within the input volume may be used to route or distribute images of the input volume to corresponding AI pipelines that are trained and configured to process images of different phases such that an input volume may be sub-divided into constituent sub-volumes and routed to their corresponding AI pipelines for processing, e.g., a first sub-volume corresponding to portal-venous phase images sent to a first AI pipeline while a second sub-volume corresponding to arterial phase being sent to a second AI pipeline for processing. If the volume of input CT medical images comprises a single phase, or after filtering and optionally routing of a sub-volume to a corresponding AI pipeline such that the AI pipeline(s) process images of an input volume, or sub-volume, of a single phase, then the volume (or sub-volume) is passed onto a next stage of the AI pipeline for further processing.

The second primary stage is an anatomical structure of interest (which in the example embodiments is the liver) detection stage in which the portions of the volume that depict the anatomical structure of interest are identified and passed to the next downstream stage of the AI pipeline. The anatomical structure of interest detection stage (hereafter referred to as the liver detection stage in accordance with the example embodiment), comprises a machine learning (ML)/deep learning (DL) computer model that is specifically trained and configured to perform computerized medical image analysis to identify portions of input medical images that correspond to the anatomical structure of interest, e.g., a liver. Such medical image analysis may comprise training the ML/DL model on labeled training medical image data as input to determine whether an input medical image (training image during training) comprises the anatomical structure of interest, e.g., the liver. Based on a ground truth of the image labels, the operational parameters of the ML/DL model may be adjusted to reduce a loss or error in the results generated by the ML/DL model until convergence is achieved, i.e. the loss is minimized. Through this process, the ML/DL model is trained to recognize patterns of medical image data indicative of the presence of the anatomical structure of interest (liver in the example). Thereafter, once trained, the ML/DL model may be executed on new input data to determine if the new input medical image data has patterns indicative of the anatomical structure being present and if the probability is greater than a predetermined threshold, it can be determined that the medical image data comprises the anatomical structure of interest.

Thus, in the liver detection stage, the AI pipeline uses the trained ML/DL computer model to determine if the volume of input CT medical images comprise images depicting the liver. The portions of the volume that depict the liver are passed along with the results of the phase classification stage to a determination stage of the AI pipeline that determines whether a single phase of medical imaging is present and whether at least a predetermined amount of the anatomical structure of interest is present in the portions of the volume depicting the anatomical structure of interest (e.g., liver). The determination of whether a predetermined amount of the anatomical structure of interest is present may be determined based on known measurement mechanisms that determine measurements of structures from medical images, e.g., calculating sizes of structures from differences in pixel positions within an image. The measurements may be compared to predetermined sizes, e.g., average sizes, of the anatomical structure for similar patients having similar demographics such that if the measurements represent at least a predetermined amount or portion of the anatomical structure then further processing may be performed by the AI pipeline. In one illustrative embodiment, this determination determines if at least ⅓ of the liver is present in the portions of the volume of input CT medical images that are determined to depict the liver, for example. While ⅓ is used in the example embodiments, any predetermined amount of the structure, determined to be appropriate for the particular implementation, may be used without departing from the spirit and scope of the present invention.

In one illustrative embodiment, in order to determine whether a predetermined amount of an anatomical structure of interest is present in the volume of input CT medical images, an axial score is defined such that a slice corresponding to a medical image in the volume that has a first representation of the anatomical structure of interest, e.g., liver, i.e. the first slice containing the liver (FSL), is given a slice score of 0 and the last slice containing the liver (LSL) has a score of 1. The first and last slice are defined, assuming a human biological entity, going from most inferior slice in volume (MISV) (closest to a lower extremity, e.g., the feet) to the most superior slice in the volume (MSSV) (closest to the head). The liver axial score estimate (LAE) is defined by a pair of slice scores, $s_{sup}$ and $s_{inf}$, which correspond to slice scores for the MSSV and MISV slices, respectively. A ML/DL computer model is specifically configured and trained to determine the slice scores $s_{sup}$ and $s_{inf}$ for a volume of input CT medical images, as will be described in greater detail hereafter. Knowing these slice scores and knowing from the definition above that the liver extends from 0 to 1, the mechanisms of the illustrative embodiments are able to determine the fraction of the liver in the field of view of the volume of input CT medical images.

In some illustrative embodiments, the slice scores $s_{sup}$ and $s_{inf}$ may be found indirectly by first dividing the volume of input CT medical images into sections and then for each section executing the configured and trained ML/DL computer model on the slices of the section to estimate a height for each slice in order to determine the most superior (closest to the head) and most inferior (closest to the feet) liver slice in the section $s'_{sup}$ and $s'_{inf}$. Given the estimates of $s'_{sup}$ and $s'_{inf}$, estimates of $s_{sup}$ and $s_{inf}$ are found by extrapolation as it is known how the section is located with respect to the entire volume of input CT medical images. This approach is based on a robust estimator of the height of an arbitrary slice from the input volume (or sub-volume associated with the target phase). Such an estimator can be obtained by learning a regression model, for instance by using a deep learning model that performs the estimation of the height from a chunk (set of consecutive slices). A long short-term memory (LSTM) type artificial neural network model, for example, is suitable for these tasks are they have the capability to encode the ordering of the slices containing the liver and abdomen anatomy. It should be noted that for each volume, there will be n number of estimates of $s_{sup}$ and $s_{inf}$ where n is the number of sections per volume. In one illustrative embodiment, the final estimate is obtained by taking the unweighted mean of those n estimates, however in other illustrative embodiments, the final estimate may be generated using other functions of the n estimates.

Having determined the final estimates of the $s_{sup}$ and $s_{inf}$ for the volume of input CT medical images, the fraction of the anatomical structure of interest, e.g., liver, is calculated based on these values. This task is made possible by the estimation of the height of each slice. From an estimation of the height of the first (h1) and last (h2) slices of the liver in the input volume, assuming that the height of the actual first and last slices of the liver (whether they are contained in the input volume or not) are H1 and H2, the portion of liver visible in the input volume can be expressed as (min(h1, H1)−max(h2, H2))/(H1−H2). This calculated fraction may then be compared to a predetermined threshold value to determine if a predetermined minimum amount of the anatomical structure of interest is present in the volume of input CT medical images or not, e.g., at least ⅓ of the liver is present in the volume of input CT medical images.

If the determinations result in a determination that multiple phases are present and/or a predetermined amount of the anatomical structure of interest is not present in the portions of the volume of input CT medical images depicting the anatomical structure, then further processing of the volume may be discontinued. If the determinations result in a determination that the volume of input CT medical images comprise a single phase and at least a predetermined amount of the anatomical structure of interest (e.g. ⅓ of the liver is shown in the images), then the portions of the volume of input CT medical images which depict the anatomical structure are forwarded to the next stage of the AI pipeline for processing.

In the next stage of the AI pipeline, the AI pipeline performs lesion detection on the portions of the volume of input CT medical images representing the anatomical structure of interest, e.g., the liver. This liver and lesion detection stage of the AI pipeline uses an ensemble of ML/DL computer models to detect the liver and lesions in the liver as represented in the volume of input CT medical images. The ensemble of ML/DL computer models uses differently trained ML/DL computer models to perform liver and lesion detection, with the ML/DL computer models being trained and using loss functions to counterbalance false positives and false negatives in lesion detection. Moreover, the ML/DL computer models of the ensemble are configured such that a third loss function forces the outputs of the ML/DL computer models to be consistent with each other.

Assuming a liver detection and lesion detection being performed in this stage of the AI pipeline, a first ML/DL computer model is executed on the volume of input CT medical images to detect the presence of the liver. This ML/DL computer model may be the same ML/DL computer model employed in the prior AI pipeline stage of anatomical structure of interest detection, and thus, the results previously obtained may be utilized. A plurality (two or more) other ML/DL computer models are configured and trained to perform lesion detection in the portions of the medical images depicting the liver. A first ML/DL computer model is configured with two loss functions. The first loss function penalizes errors in false negatives, i.e. classifications falsely indicating that there are no lesions present (normal anatomical structure). The second loss function penalizes errors in false positive results, i.e. classifications falsely indicating that there are lesions present (abnormal anatomical structure). The second ML/DL is trained to detect lesions using an adaptive loss function which penalizes false positive errors in slices of the liver containing normal tissue, and penalizes false negative errors in slices of the liver containing lesions. The detection output from the two ML/DL models is averaged to produce a final lesion detection.

The results of the liver/lesion detection stage of the AI pipeline includes one or more contours (outlines) of the liver as well as a detection map identifying portions of medical imaging data elements corresponding to detected lesions, e.g., a voxel-wise map of liver lesions detected in the volume of input CT medical images. The image map is then input to a lesion segmentation stage of the AI pipeline. The lesion segmentation stage, as will be described in greater detail hereafter, uses a watershed technique to partition the detection map to generate image element, e.g., voxel, partitioning of the input CT medical images. The liver lesion segmentation stage identifies all of the contours corresponding to lesions present in slices of the volume of input CT medical images based on this partitioning and performs operations to identify which contours correspond to the same lesion in three dimensions. The lesion segmentation aggregates correlated lesion contours to generate three dimensional partitioning of lesions. The lesion segmentation uses inpainting of lesion image elements, e.g., voxels, and non-liver tissues represented in the medical images so as to focus on each lesion individually and performs active contour analysis. In this way, individual lesions may be identified and processed without biasing the analysis due to other lesions in the medical images or biasing due to portions of the image outside the liver.

The result of the lesion segmentation is a listing of lesions with their corresponding outlines or contours in the volume of input CT medical images. These output may contain findings that are not actual lesions. In order to minimize the impact of those false positives, the outputs are provided to a next stage of the AI pipeline directed to false positive removal using a trained false positive removal model. This false positive removal model of the AI pipeline acts as a classifier to identify what outputs are actual lesions and what are the false positives from the detected findings. The input is composed of a volume of images (VOI) around the detected finding associated with a mask resulting from the lesion segmentation refinement. The false positive removal model is trained using data that are the result of the detection/segmentation stages: objects that are lesions from the ground truth that are detected by the detection algorithm are used to represent the lesion class during training, while detections that do not match any lesion from the ground truth are used to represent the non-lesion (false positive) class.

In order to further improve the overall performance a dual operating point strategy is employed on the lesion detection and false positive models. The idea is to note that the output of the AI pipeline can be interpreted at different level. First, the output of the AI pipeline can be used to tell whether an exam volume, i.e. input volume or volume of images (VOI), has a lesion or not. Second, the output of the AI pipeline aims at maximizing the detection of lesions regardless of whether they are contained in a same patient/exam/volume or not. For the sake of clarity, measurements made for an exam will be referred to herein as "patient level" and measures made for a lesion will be referred herein as "lesion level." Maximizing the sensitivity at "lesion level" will degrade the specificity at "patient level" (one detection is enough for a patient to be said to contain lesions). This may end up being suboptimal for clinical usage as one would have to choose between having poor specificity at patient level, or low sensitivity at lesion level.

In view of this, the illustrative embodiments use a dual operating point approach for both lesion detection and false positive removal. The principle is to run first the processing with a first operating point that gives reasonable performance at patient level. Then for patients that have at least on detected lesion from the first run, a second operating point is used to re-interpret/process the detected lesion(s). This second operating point is chosen to be more sensitive. While this second operating point is less specific than the first one, this loss of specificity is contained at patient level because all patients that had no lesion detected with the first operating point are kept as is, regardless of whether the second operating point would have detected additional lesion(s) or not. Therefore, patient level specificity is determined only by the first operating point. The patient level sensitivity is between one of the first and second operating points taken alone (one false negative case from the first operating point can be turned into a true positive by the second operating point). On the lesion side, actual lesion level sensitivity is improved compared to the first operating point only. The lesion specificity is better than from the less specific second operating point taken alone as there are no false positives coming from cases processed only with the first operating point.

While the illustrative embodiments will assume particular configurations and uses of the dual operating point approach, it should be appreciated that the dual operating point approach can be used with other configurations and for other purposes where one is interested in measuring performance at group level (in the illustrative embodiments, this group level is "patient level") and element level (in the illustrative embodiments, this element level is "lesion level"). While, in the illustrative embodiments, the dual operating point approach is applied to both lesion detection and false positive removal, in can be appreciated that the dual operating point approach can be extended beyond these stages of the AI pipeline. For example, rather than patient level and lesion level, the detection of a lesion may be performed at voxel level (element) versus volume level (group). As another example, the voxel or lesion level may be used for the element level and slabs (set of slices) may be used as the group level. In still a further example, all the volume of an exam may be used as the group level instead of a single volume. It should be appreciated that this approach may also be applied to two dimensional images (e.g., chest, mammography, etc. 2D xrays) for the images to be analyzed rather than three dimensional volumes. Specificity, such as the average number of false positives per patient/group, can be used for selecting the operating point. Additionally, while the illustrative embodiments are described as applying to lesion detection and classification, the dual operating point based approach may be applied to other structures (clips, stents, implants, etc.) and beyond medical imaging.

The results of the dual operating point based detection and false positive removal lead to identification of the final filtered listing of lesions to be further processed by a lesion classification stage of the AI pipeline. In the lesion classification stage of the AI pipeline a configured and trained ML/DL computer model is executed on the listing of lesions and their corresponding contour data to thereby classify the lesions into one of a plurality of predetermined lesion classifications. For example, each lesion and its attributes, e.g., contour data, in the final filtered listing of lesions may be input to the trained ML/DL computer model which then operates on this data to classify the lesion as a particular type of lesion. The classification can be performed using a classifier (e.g., trained neural network computer model) previously trained on ground truth data in combination with the result of the previous processing steps of the AI pipeline. The classification task can be more or less complex, for instance it can be to provide a label among benign, malignant or indeterminate, for example, or in another example the actual lesion type, e.g., cyst, metastasis, hemangioma, etc. The classifier can be a neural network based computer model classifier, e.g., SVM, decision tree, etc., or a deep learning computer model, for example. The actual input of this classifier is a patch around the lesion, which in some embodiments may be augmented with a lesion mask or outline (contour).

After classification of the lesions by the lesion classification stage of the AI pipeline, the AI pipeline outputs a list of lesions and their classifications, along with any contour attributes of the lesions. Moreover, the AI pipeline may also output the liver contour information for the liver. This AI pipeline generated information may be provided to further downstream computing systems for further processing and generation of representations of the anatomical structure of interest and any detected lesions present in the anatomical structure. For example, graphical representations of the volume of input CT medical images may be generated in a medical image viewer or other computer application with the anatomical structure and detected lesions being superimposed or otherwise accentuated in the graphical representation using the contour information generated by the AI pipeline. In other illustrative embodiments, downstream processing of the AI pipeline generated information may include diagnosis decision support operations, automated medical imaging report generation based on the detected listing of lesions, classifications, and contour. In other illustrative embodiments, based on classifications of lesions, different treatment recommendations may be generated for review and consideration by medical practitioners.

In some illustrative embodiments, the listing of lesions, their classifications, and contours may be stored in a history data structure associated with a patient with which the volume of input CT medical images correspond such that multiple executions of the AI pipeline on different volumes of input CT medical images associated with that patient may be stored and evaluated over time. For example, differences between the listing of lesions and/or their associated classifications and contours may be determined to evaluate the progression of a disease or medical condition of the patient and present such information to a medical professional for assisting with treatment of the patient.

Other downstream computing systems and processing of the specific anatomical structure and lesion detection information generated by the AI mechanisms of the illustrative embodiments may be implemented without departing from the spirit and scope of the present invention. For example, the output of the AI pipeline may be used by another downstream computing system to process the anatomical structure and lesion information in the output of the AI pipeline to identify discrepancies with other sources of information (e.g., a radiology report) in order to make clinical staff aware of potential overlooked findings.

Thus, the illustrative embodiments provide mechanisms that provide an automated AI pipeline comprising a plurality of configured and trained ML/DL computer models that implement various artificial intelligence operations for various stages of the AI pipeline so as to identify anatomical structures and lesions associated with these anatomical structures in a volume of input medical images, determine the contours associated with such anatomical structures and lesions, determine classifications of such lesions, and generate a listing of such lesions as well as the contours of the lesions and the anatomical structures for further downstream computer processing of the AI generated information from the AI pipeline. The operation of the AI pipeline is automated such that there is no human intervention at any of the stages of the AI pipeline and instead specially configured and trained ML/DL computer models, trained through machine learning/deep learning computer processes, are employed to perform the specific AI analysis of the various stages. The only points at which human intervention may be present are prior to the input of the volume of input medical images, e.g., during medical imaging of the patient, and after output of the AI pipeline, e.g., viewing the augmented medical images presented via a computer image viewing application based on the output of the list of lesions and contours generated by the AI pipeline. Thus, the AI pipeline performs operations that cannot be performed by a human being as a mental process and does not organize any human activity as the AI pipeline is specifically concerned with an improved automated computer tool implemented as artificial intelligence using specific machine learning/deep learning processes that only exist within a computer environment.

Before continuing the discussion of the various aspects of the illustrative embodiments and the improved computer operations performed by the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on hardware to thereby configure the hardware to implement the specialized functionality of the present invention which the hardware would not otherwise be able to perform, software instructions stored on a medium such that the instructions are readily executable by hardware to thereby specifically configure the hardware to perform the recited functionality and specific computer operations described herein, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Lesion Detection and Classification AI Pipeline Overview

FIG. 1 is an example block diagram of a lesion detection and classification artificial intelligence (AI) pipeline (herein simply referred to as the "AI pipeline") implementing multiple specifically configured and trained ML/DL computer models to perform anatomical structure identification and lesion detection in input medical image data in accordance with one illustrative embodiment. For illustrative purposes only, the depicted AI pipeline is specifically described as being directed to liver detection and liver lesion detection in medical image data. As noted above, the illustrative embodiments are not limited to such and may be applied to any anatomical structure of interest and lesions associated with such anatomical structures of interest which may be represented in image elements of medical image data captured by medical imaging technology and the corresponding computing systems. For example, the mechanism of the illustrative embodiments may be applied to other anatomical structures, such as the lungs, heart, or the like, and the detection, identification of contours, classification, and the like, of lesions associated with the lungs, heart, or other anatomical structure of interest.

Moreover, it should be appreciated that the following description provides an overview of the AI pipeline from the level illustrated in FIG. 1 and that subsequent sections of this description will go into additional detail regarding individual stages of the AI pipeline. Each of the stages of the AI pipeline, in some illustrative embodiments, are implemented as configured and trained ML/DL computer models, such as a neural network of deep learning neural network, as represented by the symbol 103 in the various stages of the AI pipeline 100. These different ML/DL computer models are specifically configured and trained to perform the particular AI operations described herein, e.g., body part identification, liver detection, phase classification, liver minimum amount detection, liver/lesion detection, lesion segmentation, false positive remove, lesion classification, etc. While these additional sections of the following description will set forth specific embodiments for implementing the various stages of the AI pipeline which provide novel techniques, mechanisms, and approaches to performing the AI operations of the various stages, it should be appreciated that in the context of the AI pipeline as a whole, other equivalent techniques, mechanisms, or approaches may be used without departing from the spirit and scope of the illustrative embodiments. These other equivalent techniques, mechanisms, or approaches will be apparent to those of ordinary skill in the art in view of the present description and are intended to be within the spirit and scope of the present invention.

As shown in FIG. 1, the artificial intelligence (AI) pipeline 100, in accordance with one illustrative embodiment, receives a volume of input medical images 105, which in the depicted example is a volume of input computed tomography (CT) medical images represented as one or more data structures, as input which is then automatically processed by the various stages of the AI pipeline 100 to ultimately generate an output 170 that includes a listing of lesions along with their classifications and contour information, and contour information about the anatomical structure of interest, e.g., the liver in the depicted example. The volume of input medical images 105 may be captured by medical imaging technology 102 using any of a plethora of generally known, or later developed, medical imaging techniques and equipment which render images of the internal anatomical structure of a biological entity, i.e. a patient, as one or more medical image data structures. In some illustrative embodiments, this volume of input medical images 105 comprises two dimensional slices (individual medical images) of a portion of the patient's anatomical structure of a portion of their body, which are then combined to generate slabs (combinations of slices along an axis so as to provide a collection of medical images having a thickness along the axis), and which are combined to generate a three dimensional representation, i.e. a volume, of the anatomical structures of the portion of the body.

In a first stage logic 110 of the AI pipeline 100, the AI pipeline 100 determines 112 the portion of the patient's body that corresponds to the input volume of CT medical imaging data 105 and determines, via body part of interest determination logic 114, if this portion of the patient's boy represents a portion of the patient's body that corresponds to the anatomical structure of interest, e.g., an abdominal scan rather than a cranial scan, lower body scan, or the like. This evaluation is to operate as an initial filter on the use of the AI pipeline 100 only with regard to volumes of input CT medical imaging data 105 (hereafter referred to as the "input volume" 105) for which the AI pipeline 100 is specifically configured and trained to perform anatomical structure identification and contouring and lesion identification, contouring, and classification. This detection of the body part represented in the input volume 105 may look to metadata associated with the input volume 105 which may have fields specifying the region of the patient's body that was scanned, as may be specified by the source medical imaging technology computing system 102 when performing the medical imaging scans. Alternatively, the first stage logic 110 of the AI pipeline 100 may implement a specifically configured and trained ML/DL computer model for body part detection 112 that performs medical image classification with regard to particular portions of patients' bodies that performs computerized pattern analysis on the medical image data of the input volume 105 and predicts a classification of the medical imaging data with regard to one or more predetermined portions of patient bodies. In some illustrative embodiments, this evaluation may be binary, e.g., is or is not an abdominal medical imaging volume, or may be a more complex multi-class evaluation, e.g., specifically identifying probabilities or scores with regard to a plurality of different body part classifications, e.g., abdominal, cranial, lower extremities, etc.

If the body part of interest determination logic 114 of the first stage logic 110 of the AI pipeline 100 determines that the input volume 105 does not represent a portion of the patient's body where the anatomical structure of interest can be found, e.g., an abdominal portion of the body where the liver can be found, then processing of the AI pipeline 100 may be discontinued (reject case). If the body part of interest determination logic 114 of the first stage logic 110 of the AI pipeline 100 determines that the input volume 105 does represent a portion of the patient's body where the anatomical structure of interest can be found, then further processing of the input volume 105 by the AI pipeline 100 is performed as described hereafter. It should be appreciated that in some illustrative embodiments, there may be multiple different instances of the AI pipeline 100 provided, each configured and trained to process input volumes 105 corresponding to different anatomical structures which may be present in different parts of the patient's body. Thus, the first stage logic 110 may be provided outside the AI pipeline(s) 100 and may operate as routing logic to route the input volume 105 to a corresponding AI pipeline 100 that is specifically configured and trained to process input volumes 105 of particular classifications, e.g., one AI pipeline instance for liver and liver lesion detection/classification, another AI pipeline instance for lung and lung lesion detection/classification, a third AI pipeline instance for cardiac and cardiac lesion detection/classification, etc. Thus, the first stage logic 110 may include routing logic that stores a mapping of which AI pipeline instances 100 correspond to different body parts/anatomical structures of interest and, based on the detection of the body part represented in the input volume 105, may route the input volume 105 automatically to a corresponding AI pipeline instance 100 that is specifically configured and trained to process input volumes 105 corresponding to the detected body part.

Assuming that the input volume 105 is detected as representing a part of the patient's body where the anatomical structure of interest is present, e.g., an abdominal scan being present in the input volume 105 for purposes of liver lesion detection, further processing of the input volume 105 is performed by the AI pipeline 100 in second stage logic 120. This second stage logic 120 comprises two primary sub-stages 122 and 124 which may be performed substantially parallel to each other and/or in sequence depending on the desired implementation (parallel execution being represented in FIG. 1 as an example). The two primary sub-stages 122, 124 comprise a phase classification sub-stage 122 and an anatomical structure detection sub-stage 124, e.g., liver detection sub-stage 124 in the case where the AI pipeline 100 is configured to perform liver lesion detection.

The phase classification sub-stage 122 determines if the input volume 105 comprises a single imaging phase, e.g., a pre-contrast phase, an arterial contrast phase, a portal/venous contrast phase, a delayed phase, etc. Again, the phase classification sub-stage 122 may be implemented as logic that evaluates the metadata associated with the input volume 105 that may include fields specifying the phases of the medical imaging study with which the medical images correspond as may be generated by the medical imaging technology computing system 102 when performing the medical imaging. Alternatively, the illustrative embodiments may implement a configured and trained ML/DL computer model that is specifically trained to detect patterns of medical images that are indicative of different phases of a medical imaging study and thereby may classify the medical images of an input volume 105 as to which phases they correspond. The output of the phase classification sub-stage 122 may be binary indicating whether or not the input volume 105 comprises one phase or multiple phases, or may be a classification of each of the phases represented in the input volume 105 which can then be used to determine if a single phase or multiple phases are represented.

If the phase classification indicates a single phase is present in the input volume 105, then further processing by the AI pipeline 100 through the downstream stages 130-170 is performed as described hereafter. If multiple phases are detected, then the input volume 105 is not further processed by the AI pipeline 100, or as described previously, may be filtered and/or divided into sub-volumes, each sub-volume having images of a corresponding single phase such that only a sub-volume corresponding to a target phase is processed by the AI pipeline 100 and/or the sub-volumes are routed to corresponding AI pipelines configured and trained to process input volumes of images corresponding to their particular phase classification. It should be appreciated that an input volume can be rejected for several reasons (e.g., no liver present in the image, not a single-phase input volume, not enough liver present in the image, etc.). Depending on the actual root cause of the rejection, the cause of the rejection may be communicated to a user via a user interface or the like. For example, the output of the AI pipeline 100 in response to the rejection may indicate the reason for the rejection and may be utilized by a downstream computing system, e.g., a viewer or an additional automated processing system, to communicate the reason for the rejection through an output. For instance, in the case of no liver being detected in the input volume, the input volume may be silently ignored, e.g., without communicating the rejection to the user, while for an input volume containing a liver, but comprising a multiphase input volume, the rejection may communicated to the user (e.g., radiologist) by clearly stating in a user interface generated by the viewer downstream computing system that the input volume was not processed by the AI pipeline 100 due to the input volume having images of more than one phase, in order not to be mistaken with a input volumes that do not contain any findings, for example.

The second primary sub-stage 124 is a detection sub-stage for detecting an anatomical structure of interest (which in the example embodiments is the liver) in portions of the input volume 105. That is, the slices, slabs, etc. in the input volume 105, which specifically depict the anatomical structure of interest (liver), are identified and are evaluated to determine if a predetermined minimum amount of the anatomical structure of interest (liver) is present in these slices, slabs, or input volume as a whole. As mentioned previously, the detection sub-stage 124 comprises a ML/DL computer model 125 that is specifically trained and configured to perform computerized medical image analysis to identify portions of input medical images that correspond to the anatomical structure of interest, e.g., a human liver.

Thus, in the liver detection sub-stage 124, the AI pipeline 100 uses the trained ML/DL computer model 125 to determine if the volume of input CT medical images comprise images depicting the liver. The portions of the volume that depict the liver are passed along with the results of the phase classification sub-stage 122 to a determination sub-stage 126, comprising single phase determination logic 127 and minimum structure amount determination logic 128, of the AI pipeline 100 that determines whether a single phase of medical imaging is present 127 and whether at least a predetermined amount of the anatomical structure of interest is present in the portions of the volume depicting the anatomical structure of interest (e.g., liver) 128. As mentioned previously, the determination of whether a predetermined amount of the anatomical structure of interest is present may be determined based on known measurement mechanisms that determine measurements of structures from medical images, e.g., calculating sizes of structures from differences in pixel positions within an image, and compares these measurements to one or more predetermined thresholds to determine if a minimum amount of the anatomical structure of interest, e.g., liver, is present in the input volume 105, e.g., ⅓ of the liver is present in the portions of the input volume 105 that are determined to depict the liver, for example.

In one illustrative embodiment, in order to determine whether a predetermined amount of an anatomical structure of interest (liver) is present in the input volume 105, the previously described axial score mechanism may be used to evaluate the portion of the anatomical structure present in the input volume 105. As described previously, a ML/DL computer model may be configured and trained to estimate the slice scores, $s_{sup}$ and $s_{inf}$, which correspond to slice scores for the MSSV and MISV slices, respectively, for the input volume 105. In some illustrative embodiments, the slice scores $s_{sup}$ and $s_{inf}$ may be found indirectly by first dividing the input volume 105 into sections and then for each section executing the configured and trained ML/DL computer model on the slices of the section to estimate a slice score for the first and last slice in the section $s'_{sup}$ and $s'_{inf}$. Given the estimates of $s'_{sup}$ and $s'_{inf}$, estimates of $s_{sup}$ and $s_{inf}$ are found by extrapolation as it is known how the section is located with respect to the entire volume of input CT medical images. It should be noted that for each input volume 105, there will be n number of estimates of $s_{sup}$ and $s_{inf}$ where n is the number of sections per volume. In one illustrative embodiment, the final estimate is obtained by taking the unweighted mean of those n estimates, however in other illustrative embodiments, the final estimate may be generated using other functions of the n estimates.

Having determined the final estimates of the $s_{sup}$ and $s_{inf}$ for the volume of input CT medical images, the fraction of the anatomical structure of interest, e.g., liver, is calculated based on these values. This calculated fraction may then be compared to a predetermined threshold value to determine if a predetermined minimum amount of the anatomical structure of interest is present in the volume of input CT medical images or not, e.g., at least ⅓ of the liver is present in the volume of input CT medical images.

If the determinations of the determination logic 127 and 128 indicate that multiple phases are present and/or a predetermined amount of the anatomical structure of interest is not present in the portions of the input volume 105 depicting the liver, then further processing of the input volume 105 by the AI pipeline 100 with regard to stages 130-170 may be discontinued, i.e. the input volume 105 is rejected. If the determinations of the determination logic 127 and 128 result in a determination that the input volume 105 has images of a single phase and at least a predetermined amount of the liver is depicted, then the portions of the input volume 105 which depict the anatomical structure are forwarded to the next stage 130 of the AI pipeline 100 for processing. While the example illustrative embodiment forwards the sub portion of the input volume containing the liver for further processing, in other illustrative embodiments, context around the liver may also be provided, which can be done by adding a predetermined amount of margin above and below the selected liver area. Depending on how much context is needed by the subsequent processing operations, that margin can be increased up to the full coverage of the original input volume.

In the next stage 130 of the AI pipeline 100, the AI pipeline 100 performs lesion detection on the portions of the input volume 105 representing the anatomical structure of interest, e.g., the liver. This liver/lesion detection stage 130 of the AI pipeline 100 uses an ensemble of ML/DL computer models 132-136 to detect the liver and lesions in the liver as represented in the input volume 105. The ensemble of ML/DL computer models 132-136 uses differently trained ML/DL computer models 132-136 to perform liver and lesion detection, with the ML/DL computer models 132-136 being trained and using loss functions to counterbalance false positives and false negatives in lesion detection. Moreover, the ML/DL computer models 132-136 of the ensemble are configured such that a third loss function forces the outputs of the ML/DL computer models 132-136 to be consistent with each other.

In one illustrative embodiment, a configured and trained ML/DL computer model 132 is executed on the input volume 105 to detect the presence of the liver. This ML/DL computer model 132 may be the same ML/DL computer model 125 employed in the prior AI pipeline stage 120 and thus, the results previously obtained may be utilized. A plurality (two or more) other ML/DL computer models 134-136 are configured and trained to perform lesion detection in the portions of the medical images of the input volume 105 depicting the liver. A first ML/DL computer model 134 is configured and trained to operate on the input volume 105 directly and generate lesion predictions. A second ML/DL computer model 136 is configured with two different decoders that implement two different loss functions, one being a loss function that penalizes errors in false negatives, i.e. classifications falsely indicating that there are no lesions present (normal anatomical structure), and a second one being a loss function that penalizes errors in false positive results, i.e. classifications falsely indicating that there are lesions present (abnormal anatomical structure). The first decoder of the ML/DL computer model 136 is trained to identify patterns representative of a relatively large number of different lesions at the cost of having a large number of false positives. The second decoder of the ML/DL computer model 136 is trained to be less sensitive to the detection of lesions, but the lesions that are detected are much more likely to be accurately detected. A third loss function of the ensemble of ML/DL computer models as a whole compares the results of the decoders of the ML/DL computer model 136 to each other and forces them to be consistent with each other. The lesion prediction results of the first and second ML/DL computer models 134, 136 are combined to generate a final lesion prediction for the ensemble, while the other ML/DL computer model 132 that generates a prediction of a liver mask provides an output representing the liver and its contour. An example architecture of these ML/DL computer models 132-136 will be described in greater detail hereafter with regard to FIG. 6.

The results of the liver/lesion detection stage 130 of the AI pipeline 100 includes one or more contours (outlines) of the liver, as well as a detection map identifying portions of medical imaging data elements corresponding to detected lesions 135, e.g., a voxel-wise map of liver lesions detected in the input volume 105. The detection map is then input to a lesion segmentation stage 140 of the AI pipeline 100. The lesion segmentation stage 140, as will be described in greater detail hereafter, uses a watershed technique and corresponding ML/DL computer model 142 to partition the detection map to generate image element, e.g., voxel, partitioning of the medical images (slices) of the input volume 105. The liver lesion segmentation stage 140 provides other mechanisms, such as ML/DL computer model 144, which identify all of the contours corresponding to lesions present in slices of the input volume 105 based on this partitioning, and performs operations to identify which contours correspond to the same lesion in three dimensions. The lesion segmentation stage 140 further provides mechanisms, such as ML/DL computer model 146, which aggregate correlated lesion contours to generate three dimensional partitioning of lesions. The lesion segmentation uses in-painting of lesion image elements, e.g., voxels, and non-liver tissues represented in the medical images so as to focus on each lesion individually and performs active contour analysis. In this way, individual lesions may be identified and processed without biasing the analysis due to other lesions in the medical images or biasing due to portions of the image outside the liver.

The results of the lesion segmentation 140 is a listing of lesions 148 with their corresponding outlines or contours in the input volume 105. These outputs 148 are provided to a false positive removal stage 150 of the AI pipeline 100. The false positive removal stage 150 uses a configured and trained ML/DL computer model that uses a dual operating point strategy to reduce false positive lesion detections in the listing of lesions generated by the lesion segmentation stage 140 of the AI pipeline 100. A first operating point is selected to be sensitive to false positives by configuring the ML/DL computer model of the false positive removal stage 150 to remove as many lesions as possible. A determination is made as to whether a predetermined number or less of the lesions in the listing remain after the sensitive removal of false positives. If so, then the other lesions in the listing that were removed are reconsidered using a second operating point that is relatively less sensitive to false positives. The results of both approaches identify the final filtered listing of lesions to be further processed by a lesion classification stage of the AI pipeline.

After having removed false positives from the list of lesions and their contours generated by the lesion segmentation stage 140, the resulting filtered list of lesions 155 is provided as input to a lesion classification stage 160 of the AI pipeline 100 a configured and trained ML/DL computer model is executed on the listing of lesions and their corresponding contour data to thereby classify the lesions into one of a plurality of predetermined lesion classifications. For example, each lesion and its attributes, e.g., contour data, in the final filtered listing of lesions may be input to the trained ML/DL computer model of the lesion classification stage 160 which then operates on this data to classify the lesion as a particular predetermined type or class of lesion.

After classification of the lesions by the lesion classification stage 160 of the AI pipeline 100, the AI pipeline 100 generates an output 170 that includes a finalized list of lesions and their classifications, along with any contour attributes of the lesions. Moreover, the AI pipeline 100 output 170 may also include the liver contour information for the liver as obtained from the liver/lesion detection stage 130. This AI pipeline 100 generated output may be provided to further downstream computing systems 180 for further processing and generation of representations of the anatomical structure of interest and any detected lesions present in the anatomical structure. For example, graphical representations of the input volume may be generated in a medical image viewer or other computer application of the downstream computing system 180 with the anatomical structure and detected lesions being superimposed or otherwise accentuated in the graphical representation using the contour information generated by the AI pipeline. In other illustrative embodiments, downstream processing by downstream computing systems 180 may include diagnosis decision support operations, automated medical imaging report generation based on the detected listing of lesions, classifications, and contour. In other illustrative embodiments, based on classifications of lesions, different treatment recommendations may be generated for review and consideration by medical practitioners. In some illustrative embodiments, the listing of lesions, their classifications, and contours may be stored in a history data structure of a downstream computing system 180 in association with a patient identifier such that multiple executions of the AI pipeline 100 on different input volumes 105 associated with the same patient may be stored and evaluated over time. For example, differences between the listing of lesions and/or their associated classifications and contours may be determined to evaluate the progression of a disease or medical condition of the patient and present such information to a medical professional for assisting with treatment of the patient. Other downstream computing systems 180 and processing of the specific anatomical structure and lesion detection information generated by the AI pipeline 100 of the illustrative embodiments may be implemented without departing from the spirit and scope of the present invention.

Figure 2:
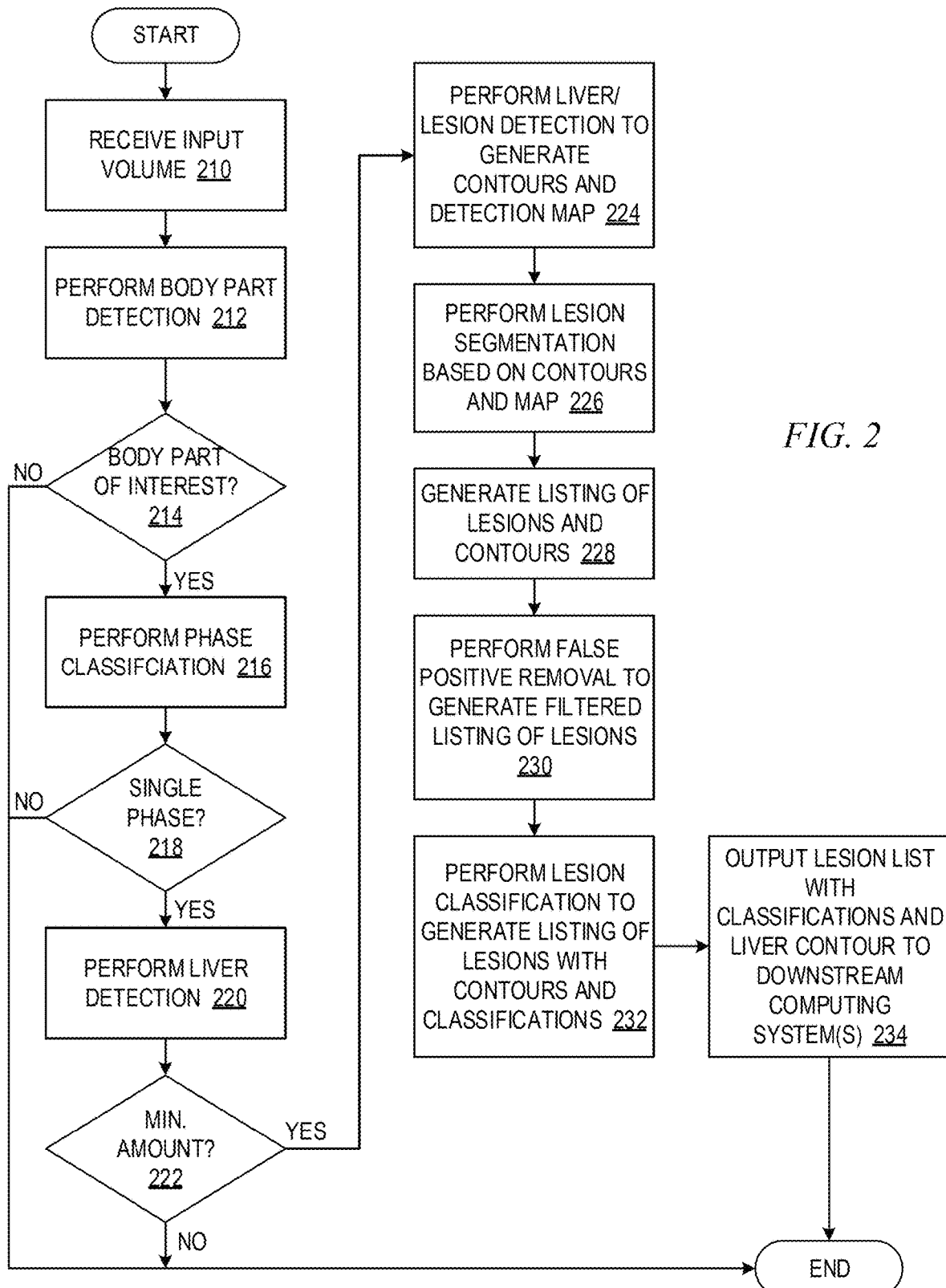
FIG. 2 is an example flowchart outlining an example operation of an AI pipeline in accordance with one illustrative embodiment.

FIG. 2 is an example flowchart outlining an example operation of an AI pipeline in accordance with one illustrative embodiment. The operation outlined in FIG. 2 may be implemented by the various stages of logic, including the configured and trained ML/DL computer models, shown in FIG. 1 and described above with specific example embodiments described hereafter in the following separate sections of this description. It should be appreciated that this operation is specifically directed to an automated artificial intelligence pipeline implemented in one or more data processing systems having one or more computing devices which are specifically configured to implement these automated computer tool mechanisms. Other than at medical image volume creation time, and use of outputs from downstream computing systems, there is no human intervention in this outlined operation of FIGS. 1 and 2. The present invention is specifically providing improved automated artificial intelligence computing mechanisms to perform the described operations which avoid human interaction and reduce potential errors due to previous manual processes by providing new and improved processes that are specifically different than any previous manual process and are specifically directed providing logic and data structures that permit the improved artificial intelligence computing mechanisms of the present invention to be implemented in automated computing tools.

As shown in FIG. 2, the operation starts by receiving an input volume of medical images from a medical imaging technology computing system, e.g., a computing system providing computer tomography (CT) medical images (step 210). The AI pipeline operates on the received input volume to perform body part detection (step 212) so that a determination may be performed as to whether a body part of interest is present in the receive input volume (step 214). If a body part of interest, e.g., the abdomen in the case of liver lesion detection and classification, is not present in the input volume, then the operation terminates. If the body part of interest is present in the input volume, phase classification and minimum anatomical structure evaluations are performed, either sequentially or in parallel.

That is, as shown in FIG. 2, phase classification is performed (step 216) on the input volume to determine if the input volume comprises medical images (slices) for a single phase of medical imaging (e.g., pre-contrast imaging, partial contrast imaging, delay phase, etc.) or multiple phases. A determination is then made as to whether the phase classification indicates a single phase or multiple phases (step 218). If the input volume comprises medical images directed to multiple phases, the operation terminates; otherwise if the input volume comprises medical images directed to a single phase, the operation continues to step 220.

In step 220, detection of the anatomical structure of interest, e.g., the liver in the depicted examples, is performed so as to determine whether a minimum amount of the anatomical structure is present in the input volume to be able to perform accurately the subsequent stages of the AI pipeline operations. A determination is made as to whether a minimum amount of the anatomical structure is present or not, e.g., at least ⅓ of the liver is represented in the input volume (step 222). If the minimum amount is not present, the operation terminates; otherwise, the operation continues to step 224.

In step 224 liver/lesion detection is performed to generate contours and a detection map for the lesions. These contours and detection map are provided to lesion segmentation logic which performs lesion segmentation, e.g., liver lesion segmentation in the depicted example, based on these contours and detection map (step 226). The lesion segmentation results in the generation of a listing of lesions and their contours, as well as detection and contour information for the anatomical structure (e.g., liver) (step 228). Based on this listing of lesions and their contours, false positive removal operations are performed on the lesions in the listing to remove false positives and generate a filtered listing of lesions and their contours (step 230).

The filtered listing of lesions and their contours are provided to lesion classification logic which performs lesion classification to generate a finalized listing of lesions, their contours, and the lesion classifications (step 232). This finalized listing is provided along with liver contour information to downstream computing systems (step 234) which may operate on this information to generate medical imaging views in a medical imaging viewer application, generate treatment recommendations based on classifications of detected lesions, evaluate historical progression of lesions over time for the same patient based on a comparison of the finalized listing of lesions generated by the AI pipeline at different points in time, or the like.

Thus, the illustrative embodiments as outlined above provide automated artificial intelligence mechanisms and ML/DL computer models that operate on an input volume of medical images and generates a listing of lesions, their contours, and classifications, while minimizing false positives. The illustrative embodiments provide automated artificial intelligence computer tools that specifically identify, in a given set of image voxels of the input volume, which ones of the voxels correspond to a portion of an anatomical structure of interest (e.g., the liver), and which ones of those voxels correspond to lesions in the anatomical structure of interest (e.g., liver lesions). The illustrative embodiments provide a distinct improvement over previous approaches, both manual and automated, in that the illustrative embodiments can be integrated in a fully automated computer tool in the clinician workflow. In fact, based on the early stages of the AI pipeline design of the illustrative embodiments, which to accept input volumes of only a single phase, e.g., abdominal scans, and reject input volumes that do not depict an anatomical structure of interest (e.g., liver), or do not depict a predetermined amount of the anatomical structure of interest, (e.g., too small and amount of the liver), only the meaningful input volumes are processed through the automated AI pipeline, thereby preventing the radiologist spending valuable manual resources on useless or faulty results when reviewing non-anatomical structure of interest input volumes, e.g., non-liver cases. In addition to preventing flooding the radiologist with useless information, the automated AI pipeline of the illustrative embodiments also ensure smooth information technology integration by avoiding congestion of the AI pipeline and downstream computing systems such as network, archiving, and review computing systems with data associated with cases that do not corresponding to anatomical structures of interest or cases that fail to provide a sufficient amount of the anatomical structure of interest. Moreover, as described above, the automated AI pipeline of the illustrative embodiments allows for accurate detection, measurements and characterization of lesions in a fully automated manner, which is made technically possible by the automated AI pipeline structure and its corresponding automated ML/DL computer model based components of one or more of the illustrative embodiments.

ML/DL Computer Model for Detecting Minimum Amount of Anatomical Structure Present in Input Volume As noted previously, as part of the processing of the input volume 105, it is important to ensure that the input volume 105 represents a single phase of medical imaging and that at least a minimum amount of the anatomical structure of interest is represented in the input volume 105. In order to determine if a minimum amount of the anatomical structure of interest is present in the input volume 105, in one illustrative embodiment, the determination logic 128 implements a specifically configured and trained ML/DL computer model that estimates slice scores for determining a portion of the anatomical structure, e.g., liver, present in the input volume 105. The following description provides an example embodiment of this configured and trained ML/DL computer model based on a defined axial score technique.

Figure 3A:
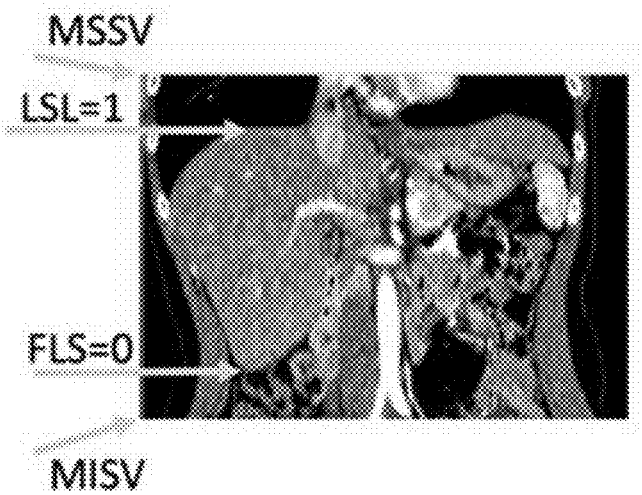
FIG. 3A is an example diagram illustrating an example input volume of slices (medical images) of an abdominal portion of a human patient in accordance with one illustrative embodiment.

FIG. 3A is an example diagram illustrating an example input volume (medical images) of an abdominal portion of a human patient in accordance with one illustrative embodiment. In the depiction of FIG. 3A, a two-dimensional representation of the three-dimensional volume is shown. Slices are horizontal lines within the two-dimensional representation shown in FIG. 3A, but would be represented as planes extending into and/or out of the page to represent a flattened two-dimensional slice of the human body with the stacking of these planes resulting in a three-dimensional image As shown in FIG. 3A, the illustrative embodiments define an axial score for slices that range from 0 to 1. The axial score is defined such that a slice corresponding to a first slice containing liver (FSL) has a slice score of 0 and a last slice containing liver (LSL) has a score of 1. In the depicted example, the first and last slices are defined in association with a most inferior slice in the volume (MISV) and a most superior slice in the volume (MSSV), where inferior and superior are determined along a given axis of the volume, e.g., the y-axis in the depicted example of FIG. 3A. Thus, in this depicted example, the MSSV is at a highest y-axis valued slice and the MISV is at a lowest y-axis valued slice. For example, the MISV may be closest to a lower extremity of the biological entity, e.g., the feet of a human subject, and the MSSV may be closest to an upper portion of the biological entity, e.g., the head of a human subject. The FLS is a slice depicting the anatomical structure of interest, e.g., the liver, that is relatively closest to the MISV. The LSL is a slice depicting the anatomical structure of interest that is relatively closest to the MSSV. In one illustrative embodiment, a trained ML/DL computer model, e.g., neural network, may assign axial scores by taking chunks of slices as an input and outputting the height (axial score) of the central slice in the chunk. This trained ML/DL computer model is trained with a cost function that minimizes the error in the actual height (e.g., least square error). This trained ML/DL computer model is then applied to all the chunks that cover the input volume (with possibly some overlap between the chunks).

The liver axial score estimate (LAE) is defined by a pair of slice scores, $s_{sup}$ and $s_{inf}$, which correspond to slice scores for the MSSV and MISV slices, respectively. A ML/DL computer model of the determination logic 128 in FIG. 1 is specifically configured and trained to determine the slice scores $s_{sup}$ and $s_{inf}$ for an input volume 105 and knowing these slice scores, the mechanisms of the illustrative embodiments are able to determine the fraction of the liver in the field of view of the input volume 105.

In some illustrative embodiments, the slice scores $s_{sup}$ and $s_{inf}$ may be found indirectly by first dividing the input volume 105 into sections, e.g., sections comprising X number of slices, e.g., 20 slices, and then for each section executing the configured and trained ML/DL computer model on the slices of the section to estimate a slice score for the first and last slice in the section $s'_{sup}$ and $s'_{inf}$, where "first" and "last" may be determined in accordance with a progression direction along an axis of the three-dimensional volume 105, e.g., from a first slice to a last slice along a y-axis progressing from smallest y-axis value slice to highest y-axis value slice. Given the estimates of $s'_{sup}$ and $s'_{inf}$, estimates of $s_{sup}$ and $s_{inf}$ are found by extrapolation as it is known how the section is located with respect to the entire volume 105. It should be noted that for each volume, there will be n number of estimates of $s_{sup}$ and $s_{inf}$ where n is the number of sections per volume. In one illustrative embodiment, the final estimate is obtained by taking the unweighted mean of those n estimates, however in other illustrative embodiments, the final estimate may be generated using other functions of the n estimates.

Figure 3B:
FIG. 3B shows another depiction of the input volume of FIG. 2A with a section of slices represented along with its corresponding axial scores $s'_{inf}$ and $s'_{sup}$.

For example, FIG. 3B shows another depiction of the input volume of FIG. 3A with a section of slices represented along with its corresponding axial scores $s'_{inf}$ and $s'_{sup}$. As shown in FIG. 3B, a section is defined as 20 slices 5 mm apart in this example. For each 20-slice section of the volume, slice score $s'_{sup}$ and inf are estimated by the ML/DL computer model and $s_{sup}$ and $s_{inf}$ are obtained from an extrapolation of these $s'_{sup}$ and $s'_{inf}$ values along a given range, e.g., a range from 0 to 1, a range from −0.5 to 1.2, or any other desired predetermined range suitable to the particular implementation. In this example, assuming a predetermined range of −0.5 to 1.2, if $s_{sup}$ is estimated by the application of the ML/DL computer model and the extrapolation to be approximately 1.2 and $s_{inf}$ is estimated to be −0.5 indicates that the entire liver is contained in the volume. Similarly, if the $s_{sup}$ is estimated to be 1.2 and the $s_{inf}$ is 0.5, these values indicate that approximately 50% of the superior axial liver extend is contained in the volume, e.g., coverage is (1.2−0.5)/(1.2−(−0.5))=0.41. As an additional example, in another illustrative embodiment in which the liver starts at −2.0 and ends at 0.8 (i.e., $s_{sup}$ is estimated to be 0.8 and $s_{inf}$ is estimated to be 2.0), the upper bound of the liver is lower than 1.2 so the liver is cut on the upper part and the lower bound is lower than −0.5 such that the bottom part of the liver is fully covered. This indicates that approximately 80% of the inferior axial liver extend is contained in the volume, i.e. coverage is (0.8−max(−2, −0.5))/(1.2−(−0.5))=0.76.

Figure 3C:
FIG. 3C is an example diagram of the input volume of FIG. 2A in which the volume is divided axially into n fully overlapping sections.

FIG. 3C is an example diagram of the input volume of FIG. 3A in which the volume is divided axially into n fully overlapping sections. In the depicted example, there are 7 sections indicated by arrows. It should be noted in this example that the last two sections (arrows at the top of the diagram) are almost completely the same. As mentioned previously, the $s'_{sup}$ and $s'_{inf}$ values are estimated by the ML/DL computer model for each of these sections and used to extrapolate the $s_{sup}$ and $s_{inf}$ values for the MSSV and MISV slices, which can then be used to determine an amount of the anatomical structure of interest that is present in the input volume 105.

Thus, the $s_{sup}$ and $s_{inf}$ values for MSSV and MISV are found indirectly by first dividing the input volume 105 into sections and then for each section estimating the slice scores for the first and last slice in the section $s'_{sup}$ and s' mf. Given these estimates, the values for $s_{sup}$ and $s_{inf}$ are estimated through an extrapolation since it is known how the section is located with respect to the entire input volume 105. There are n number of estimates of $s_{sup}$ and $s_{inf}$, extrapolated from each section, where n is the number of sections per volume. The final estimate may be obtained, for example, by any suitable combinational function that evaluates the n estimates, such as an unweighted mean of the n estimates or any other suitable combinational function.

Figure 4A:
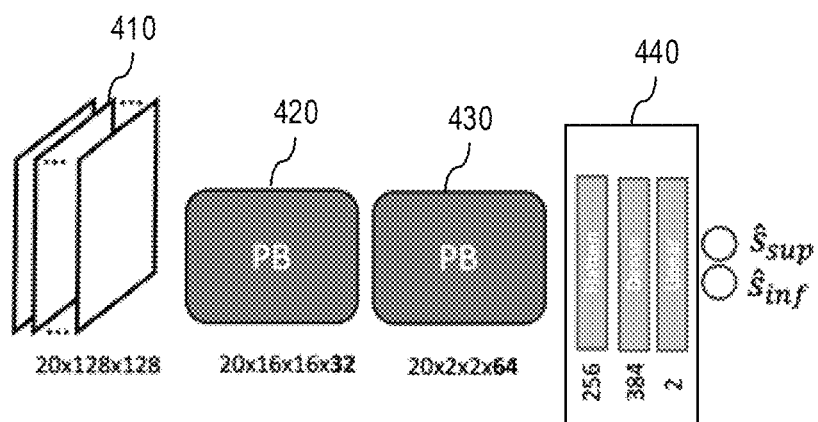
FIGS. 4A-4C are example diagrams of one illustrative embodiment of the ML/DL computer model configured and trained to estimate the $s'_{sup}$ and $s'_{inf}$ values for a section of an input volume of medical images in accordance with one illustrative embodiment.
Figure 4B:
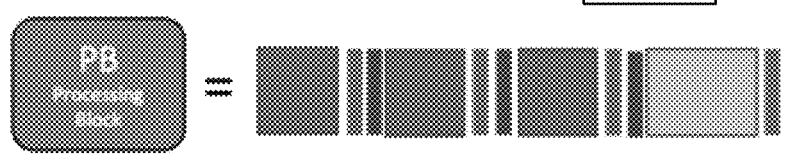
Figure 4C:
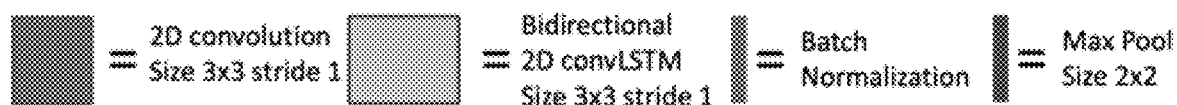

FIGS. 4A-4C show an example diagram of one illustrative embodiment of the ML/DL computer model configured and trained to estimate the $s'_{sup}$ and $s'_{inf}$ values for a section of an input volume of medical images in accordance with one illustrative embodiment. The ML/DL computer model of FIGS. 4A-4C is only one example of an architecture of the ML/DL computer model and many modifications to this architecture may be made without departing from the spirit and scope of the present invention, such as changing the tensor sizes of the input slices of the input volume, changing the number of nodes in the layers of the ML/DL computer model, changing the number of layers, etc. Those of ordinary skill in the art will recognize how to modify the ML/DL computer model of the illustrative embodiments to the desired implementation in view of the present description.

As shown in FIG. 4A, a sequence of 20 slices, representing a section 410 or "slab" of the input volume 105 is provided as input to the processing blocks (PBs) 420-430. In the depicted illustrative embodiment, the PBs 420-430 are blocks of logic that mix convolutional and LSTM layers, as shown in FIGS. 4B and 4C. Features are extracted from the convolutional layers of the PB 420, 430, which are then fed as input to the LSTM layers of the PB 420, 430. This is a type of smart/light modeling of the fact that slides have a particular order in the anatomical region or anatomical structure of interest, e.g., abdomen/liver, driven by the anatomy, e.g., relative position of the liver, kidney, heart, etc. in addition to the liver anatomy itself. In the depicted example, initially the tensor size of the 20 slices 410 is 128×128 in this example. The first processing block 420 reduces the size of the tensor by 8 in this example embodiment to generate a 20 slice section (it should be appreciated that the number of slices in a section is implementation specific and can be modified without departing from the spirit and scope of the present invention) with slices having dimensions 16×16×32, where 32 is the number of filters. A second processing block 430 converts the input section slices to a 20 slice section with slices having dimensions 2×2×64, where 64 is the number of filters. A subsequent neural network 440 configured with flattening, dense, and linear layers is configured and trained to generate the $s'_{sup}$ and $s'_{inf}$ estimates for the input section 410 of the input volume 105. FIG. 4B shows the composition of the processing block (PB) with regard to the convolutional and LSTM layers, and FIG. 4C shows example configurations of each of these convolutional and LSTM layers of each PB in accordance with one illustrative embodiment.

With the ML/DL computer model architecture of FIGS. 4A-4C as an example, during training of this ML/DL computer model, in one illustrative embodiment, medical imaging data, e.g., Digital Imaging and Communications in Medicine (DICOM) data, is assembled into an input volume, e.g., a three dimensional array with $S_i \times 512 \times 512$ size, float 32, with Hounsfield Unit (HU) value, which is a normalized physical value depicting the attenuation of the X-ray of the material being presented at a given location, e.g., voxel. $S_i$ is the number of slices in the $i^{th}$ volume where i is in the range of 0 to N−1 with N being the total number of volumes. Each input volume is processed by a body part detector and an approximate region corresponding to the abdomen is extracted (in the case of liver detection) as described previously. The abdomen is defined as a continuous region between axial scores −30, 23, for example, from the body part detector. Slices outside this continuous region are rejected and the ground truth may be defined as locations of FSL and LSL that are appropriately adjusted. For example, assuming the input volume ranges from a to b, the input volume is rejected if there is no overlap between [a:b] and [−30, 23]. In other words, if b>23 or if a<−30.

The input sections 410, or "slabs", are resliced to a predetermined slice separation, e.g., 5 mm. The input sections 410 are reshaped in x, y dimension to 128×128 which results in N sections 410 of shape $M_i \times 128 \times 128$. This is referred to as downsampling of the data in the input volume. As the ordering of slices within an input volume relies on rough information, e.g., size of the organs, the AI pipeline still operates well on the downsampled data and both processing and training time for the AI pipeline are improved due to the reduction in size of the downsampled data.

Input sections 410 which have less than a predetermined number of slices, e.g., 20, or a pixel size smaller than a predetermined pixel size, e.g., 0.55 mm, are rejected resulting in N' of the $M_i \times 128 \times 128$ sections. Values in sections are clipped and normalized using linear transformation from their acquisition range (e.g. −1024, 2048) to range (0, 1). At this point N' of $M_i \times 128 \times 128$ sections processed are, as described above, constitute a training set upon which the neural network 440 is trained to generate estimates of $s'_{sup}$ and $s'_{inf}$ for the input sections.

With regard to performing inference with the trained neural network 440, the above operations for processing the input volume 105 through body part detection, slice selection corresponding to the body part of interest, re-slicing, reshaping, rejection of certain sections not meeting predetermined requirements, and generating the clipped and normalized sections are again performed with regard to new sections of an input volume 105. After generating the clipped and normalized sections, the input volume 105 is divided into R−ceil(M−10)/10 sub-volumes, or sections, containing 20 slices, to thereby generate a partitioning of the slices with overlapping chunks. For example, if there is a N'=31 slices volume (slices numbered 0-30), three sections or sub-volumes are defined which contain the following overlapping slices: 0-19, 10-29, 11-30. The sections or sub-volumes will typically have an overlap of approximately at least 50%.

Thus, a ML/DL computer model is provided, configured, and trained so as to estimate the $s_{sup}$ and $s_{inf}$ values for an input volume based on estimates of the $s'_{sup}$ and $s'_{inf}$ values for sections of the volume corresponding to a predetermined number of slices (medical images) given a defined axial score range from 0 to 1. From these estimates, a determination can be made as to whether the input volume comprises medical slices that together constitute at least a predetermined amount of the anatomical structure of interest, e.g., the liver. This determination may be part of the determination logic 128 of the AI pipeline 100 for determining whether sufficient representation of the anatomical structure is present in the input volume 105 to allow for accurate liver/lesion detection, lesion segmentation, etc. in further downstream stages of the AI pipeline 100 as previously discussed above.

Figure 5:
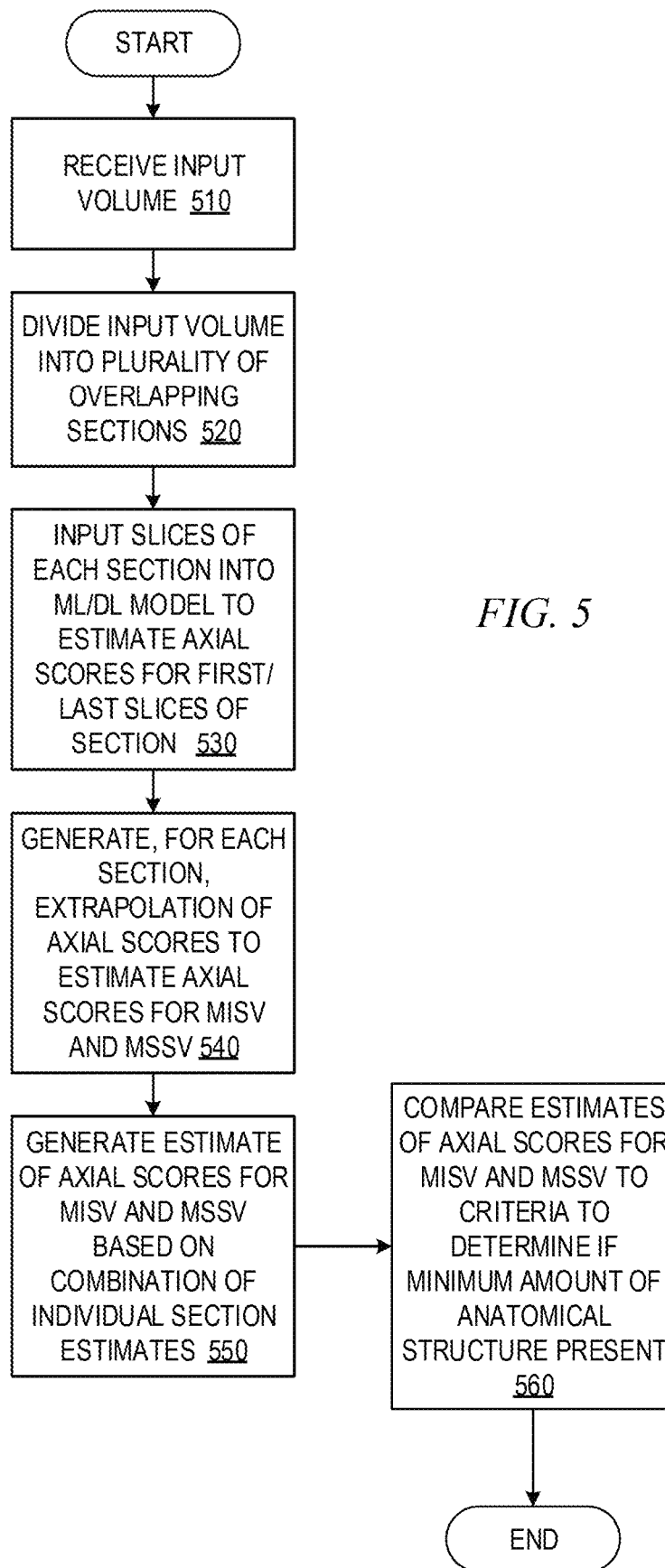
FIG. 5 is a flowchart outlining an example operation of liver detection and predetermined amount of anatomical structure determination logic of an AI pipeline in accordance with one illustrative embodiment.

FIG. 5 is a flowchart outlining an example operation of liver detection and predetermined amount of anatomical structure determination logic of an AI pipeline in accordance with one illustrative embodiment. As shown in FIG. 5, the liver detection operation of the AI pipeline starts by receiving the input volume (step 510) and divides the input volume into a plurality of overlapping sections of a predetermined number of slices for each section (step 520). The slices for each section are input to a trained ML/DL computer model that estimates the axial scores for the first and last slices in each section (step 530). The axial scores for the first and last slices are used to extrapolate to scores for the most inferior slice in the volume (MISV) and the most superior slice in the volume (MSSV) for the input volume (step 540). This results in a plurality of estimates for the axial scores for the MISV and MSSV which are then combined through a function of the individual estimates to thereby generate an estimate of the axial scores for the MISV and MSSV of the input volume, e.g., a weighted mean of the like (step 550). Based on the estimate of the axial score for the MISV and MSSV, the axial scores are compared to criteria for determining whether or not a predetermined amount of an anatomical structure of interest, e.g., the liver, is present in the input volume (step 560). Thereafter the operation terminates.

Liver/Lesion Detection

Assuming that the input volume 105 is determined to have a single phase represented, and that the input volume 105 has a predetermined amount of the anatomical structure of interest represented in the slices of the input volume 105, as described previously, liver/lesion detection is performed on the portion of the input volume 105 comprising the anatomical structure of interest. The liver/lesion detection logic of the AI pipeline 100 stage 130, in one illustrative embodiment, employs a configured and trained ML/DL computer model that operates to detect the anatomical structure of interest (e.g., liver) in the slices of the input volume 105 (again, in some illustrative embodiments, this may be the same ML/DL computer model 125 used in stage 120 for liver detection). The liver/lesion detection logic of the AI pipeline 100 stage 130 also includes an ensemble of a plurality of other configured and trained ML/DL computer models to detect lesions in images of the anatomical structure of interest (liver).

Figure 6:
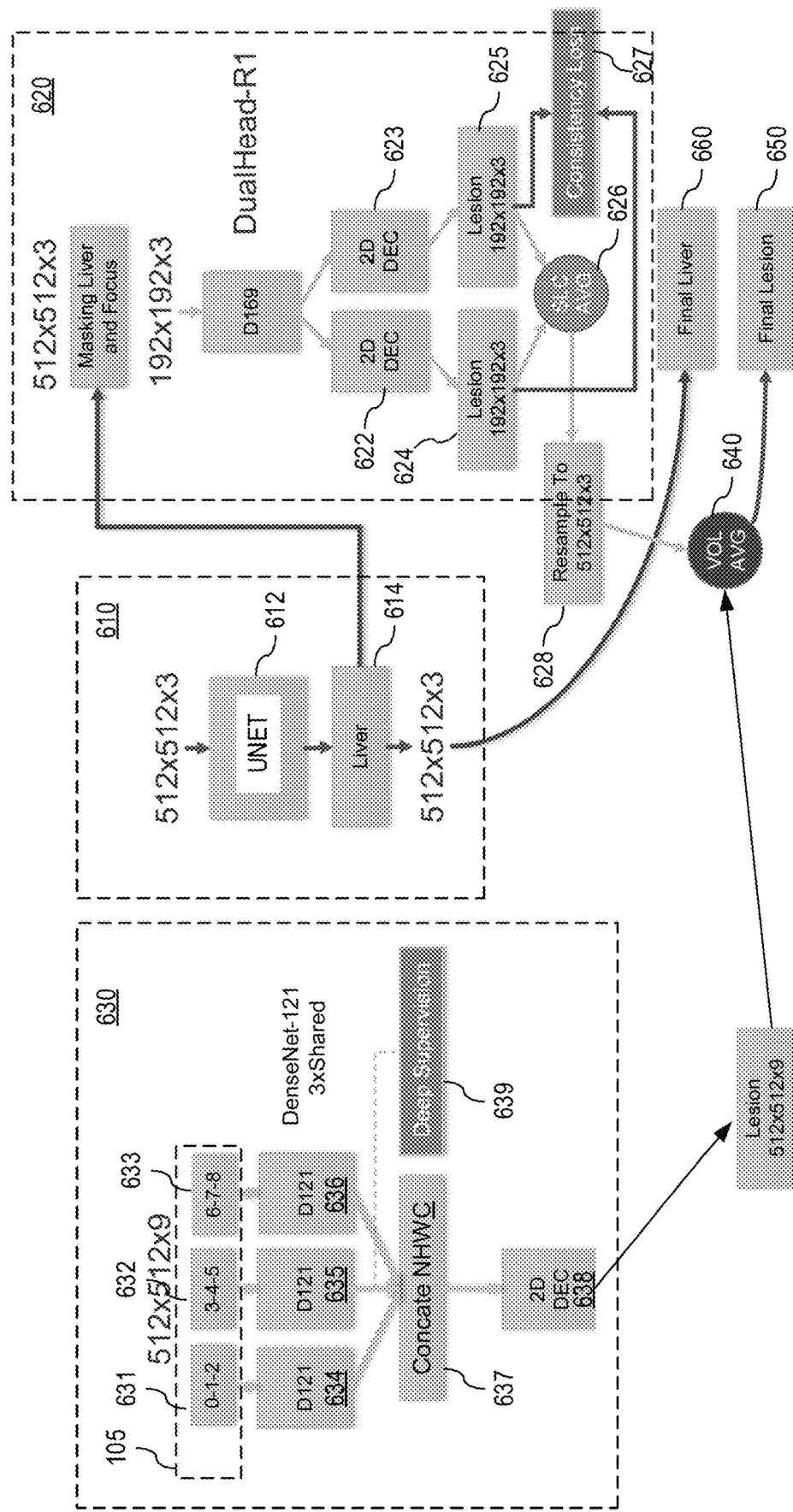
FIG. 6 is an example diagram of an ensemble of ML/DL computer models used to perform lesion detection in an anatomical structure of interest (e.g., the liver) in accordance with one illustrative embodiment.

FIG. 6 is an example diagram of an ensemble of ML/DL computer models used to perform lesion detection in an anatomical structure of interest (e.g., the liver) in accordance with one illustrative embodiment. The ensemble of ML/DL computer models 600 comprises a first ML/DL computer model 610 for detecting an anatomical structure of interest, e.g., the liver, and generating a corresponding mask. The ensemble of ML/DL computer models 600 also comprises a second ML/DL computer model 620 that is configured and trained to process a liver masked input and generate lesion predictions using two competing loss functions implemented in two decoders of the second ML/DL computer model 620. One loss function is configured to penalize false positive errors (yielding low sensitivity, but high precision) and the other is configured to penalize false negative errors (yielding high sensitivity, but lower precision). An additional loss function, referred to as the consistency loss 627 in FIG. 6, is employed for the second ML/DL computer model 620 and forces the outputs generated by the two competing decoders to be similar (consistent) to each other. The ensemble of ML/DL computer models further includes a third ML/DL computer model 630 that is configured and trained to process the input volume 105 directly and generate lesion predictions.

As shown in FIG. 6 and noted above, the ensemble 600 comprises a first configured and trained ML/DL computer model 610 that is specifically configured and trained to identify an anatomical structure of interest in input medical images. In some illustrative embodiments, this first ML/DL computer model 610 comprises a U-Net neural network model 612 configured and trained to perform image analysis to detect the liver within a medical image, however it should be appreciated that the illustrative embodiments are not limited to this particular neural network model and any ML/DL computer model that may perform segmentation may be utilized without departing from the spirit and scope of the present invention. U-Net is a convolutional neural network developed for biomedical image segmentation at the Computer Science Department of the University of Freiburg, Germany. The U-Net neural network is based on a fully convolutional network with an architecture modified and extended to work with fewer training images and to yield more precise segmentations. U-Net is generally known in the art and thus, a more detailed explanation is not provided herein.

As shown in FIG. 6, in one illustrative embodiment, the first ML/DL computer model 610 may be trained to process a predetermined number of slices at a time with the number being determined as appropriate for the desired implementation, e.g., 3 slices was determined through empirical processes to yield good results. The slices of the input volume, in one illustrative embodiment were 512×512 pixel medical images, for example, although other implementations may use different slice dimensions without departing from the spirit and scope of the illustrative embodiments. The U-Net generates segmentations of anatomical structures in the input slices resulting in one or more segments corresponding to an anatomical structure of interest, e.g., the liver. The first ML/DL computer model 610 generates, as part of this segmentation, a segment representing a liver mask 614. This liver mask 614 is provided as an input to at least one of the other ML/DL computer models 620 of the ensemble 600 in order to focus processing by the ML/DL computer model 620 on only the portion of input slices of the input volume 105 corresponding to the liver. By pre-processing the input to the ML/DL computer model with a liver mask 614, the processing by the ML/DL computer model may be focused on the portions of the input slices that correspond to the anatomical structure of interest and not on the "noise" in the input images. The others of the ML/DL computer models, e.g., ML/DL computer model 630, receives the input volume 105 directly without liver masking using the liver mask 614 generated by the first ML/DL computer model 610.

In the depicted ensemble 600 illustrative embodiment, the third ML/DL computer model 630 is composed of an encoder section 634-636 and a decoder section 638. ML/DL computer model 630 is configured to receive a 9-slice slab of the input volume 105 which is then separated into groups 631-633 of 3 slices each, with each group 631-633 being input to a corresponding encoder network 634-636. Each encoder 634-636 is a convolutional neural network (CNN), such as a DenseNet-121 (D121), without the fully connected head, which has been pre-trained to recognize different types of objects (e.g., lesions) present in the input slices and output classification outputs indicating the detected types of objects present in the input slices, e.g., as an output classification vector or the like. The CNNs 634-636 may operate, for example, on 3 channels of the input slices and the resulting output features of the CNNs 634-636 are provided to concatenation NHWC logic 637, where NHWC refers to number of images in the batch (N), height of the image (H), width of the image (W), and number of channels of the image (C). The architecture of the original DenseNet network comprises many convolutional layers and skip-true connections that down-sample the 3-slice full resolution input to many feature channels with a smaller resolution. From then, a fully connected head aggregates all the features and maps them to multiple classes in the final output of the DenseNet. Because the DenseNet network is used as an encoder in the depicted architecture, the head is removed and only the down-sampled features are kept. Then in the concatenation NHWC logic 637 all the feature channels are concatenated to pass them into the decoder stage 638 which has the role of up-sampling the images until a desired (e.g. 512×512) output probability map resolution is reached.

The encoders 634-636 share the same parameters which are optimized through the training process, e.g., the weights, sampling on lesion types during training, weights on the loss, type of augmentation, etc. The training of the ML/DL computer model 630 uses two different loss functions. The main loss function is an adaptive loss which is specifically configured to penalize false positive errors in slices that do not have lesions in the ground-truth and also to penalize false negative errors in slices that have lesions in the ground-truth. The loss function is a modified version of the Tversky loss as follows: for each output slice:

$TP=\text{sum}(\text{prediction}*\text{target})$ $FP=\text{sum}((1-\text{target})*\text{prediction})$ $FN=\text{sum}((1-\text{prediction})*\text{target})$ $\text{LOSS}=1-((TP+1)/(TP+1+\text{alpha}*FN+\text{beta}*FP))$ In which "prediction" is the output probabilities of the ML/DL computer model 630 and "target" is the ground-truth lesion mask. Output probability values range between 0 and 1. Target has either 0 or 1 for each pixel in the slice. For slices that do not have lesions in them, the "alpha" term is small (e.g., zero) and "beta" is large (e.g., 10). For slices that have lesions in them, "alpha" is large (e.g., 10) and "beta" is small (e.g., 1).

The second loss function 639 is one that is connected to the output of the encoders 634-636. Because the input for this loss is coming from the middle of the ML/DL computer model 630, it is it is referred to as "deep supervision" 639. Deep supervision has shown that it forces the encoder neural networks 634-636, during the training, to learn better representations of the input data. In one illustrative embodiment, this second loss is a simple mean square error to predict whether a slice has a lesion in it or not. Hence a mapping network is used to map the output features of the encoders 634-636 to 9 values between 0 and 1 which represent the probability of having a lesion in each of the 9-slice inputs. The decoder 638 generates outputs specifying the probability map for detected lesions in the input images.

The second ML/DL computer model 620 receives a pre-processed input of 3 slices from the input volume, which have been pre-processed with the liver mask 614 generated by the first ML/DL computer model 610 to identify the portion of the 3 slices that corresponds to the liver mask 614. The resulting pre-processed input slices (which are of size 192×192×3 in the depicted example illustrative embodiment) are provided to the second ML/DL computer model 620 comprising a DenseNet-169 (D169) encoder 621 connected to two decoders (2D DEC—representing that the decoders consist of 2-dimensional neural network layers). The D169 encoder 621 is a neural network feature extractor, widely used in computer vision applications. It consists of a series of convolutional layers where features extracted from each layer are connected to any other layer in a feed-forward fashion. The features extracted in the encoder 621 are transferred to two independent decoders 622, 623, where each decoder 622, 623 is composed of 2-dimensional convolution and up-sampling layers (referred to as 2D DEC in FIG. 6). Each decoder 622, 623 is trained to detect lesions (e.g., liver lesions) in the input slices. Although both decoders 622, 623 are trained to perform a same task, i.e. lesion detection, a key difference in their training is that the two decoders 622, 623 each utilize a different loss function in order to drive the detection training into two competing directions, as discussed previously and hereafter. The final detection map of the second ML/DL model 620 is combined with that of the third ML/DL model 630 by means of the average operation 640. This procedure is applied over all the input slabs of the input volume 105 to generate the final detection map (e.g. liver-lesions).

As mentioned above, the second ML/DL computer model 620 is trained using two different loss functions, which attempt to achieve opposite detection operating point performances. That is, where one of the encoders 622 uses a loss function for training that penalizes errors in false negative lesion detection and thus, produces high sensitivity detection with relatively low precision, the other of the encoders 623 uses a loss function for training that penalizes errors in false positive lesion detection, resulting in low sensitivity detection but with high precision. One example of these loss functions may be the Focal Tversky Loss (see Abraham et al., "A Novel Focal Tversky Loss function with Improved Attention U-Net for Lesion Segmentation," arXiv: 1810.07842[cs], October 2018) with parameters adjusted for high or low penalty of false positives and false negatives in accordance with the illustrative embodiments. A third loss function, the consistency loss 627, is used to enforce consistency between the predicted detections of each decoder 622, 623. The consistency loss logic 627 compares the outputs 624, 625 of the two encoders 622, 623 to each other and forces these outputs to be similar to each other. This loss may be, for example, a mean-squared error loss between the two predicted detections, a structural similarity loss, or any other loss that enforces consistency/similarity between the compared predicted detections.

At run time, using these opposed operating point encoders 622, 623, the second ML/DL computer model 620 generates two lesion outputs 624, 625 which are input to a slice averaging (SLC AVG) logic 623 that generates an average of the lesion outputs. This average of the lesion outputs is then re-sampled to generate an output commensurate in dimension to the output of the third ML/DL computer model 630 for comparison (please note that this process consists of reverting the liver masking operation, and therefore, computing the lesion output in the original 512×512×3 resolution).

At run time, the slice averaging (SLC AVG) logic 626 operates on the lesion prediction outputs 624 and 625 of the encoders 622, 623 to generate a final detection map of the ML/DL model 620. It should be appreciated that, while the consistency loss 627 was applied during training to drive each decoder 622, 623 to learn consistent detections, at run time this consistency loss is no longer utilized and instead the ML/DL model 620 outputs two detection maps that need to be aggregated by the SLC AVG module 626. The results of the SLC AVG logic 626 are resampled to generate an output having dimensions commensurate with the input slab (512×512×3). All the generated detections of the ML/DL model 620 for each slab of the input volume 105 are combined with the generated detections of the ML/DL model 630 via the volume averaging (VOL AVG) logic 640. This logic computes the average of the two detection masks at the voxel level. The result is a Final Lesion mask 650 corresponding to the detected lesions in the input volume 105.

Thus, after training the ML/DL computer models 620, 630, when presented with new slices of a new input volume 105, the first ML/DL computer model 610 generates the liver mask 614 for pre-processing the input to the second ML/DL computer model 620, and the two ML/DL computer models 620, 630 process the input slices to generate lesion predictions that are averaged for the volume by the volume averaging logic 640. The result is a final lesion output 650 along with the liver mask output 660 based on the operation of the first ML/DL computer model 610. These outputs may be provided as the liver/lesion detection logic stage 130 output of the AI pipeline 100 which is provided to the lesion segmentation logic stage 140 of the AI pipeline 100 as previously discussed above, and described in greater detail hereafter. Thus, the mechanisms of the illustrative embodiments provide an ensemble 600 approach to anatomical structure identification and lesion detection in an input volume 105 of medical images (slices).

With the ensemble architecture as shown in FIG. 6, improved performance over the use of a single ML/DL computer model is achieved. That is, it has been observed that through the use of the ensemble architecture, an improved detection specificity at a same level of sensitivity as a single ML/DL computer model is achieved through the combining of the detection outputs of the multiple ML/DL computer models of the ensemble. That is, with the ML/DL models 620, 630 making errors (false positives) in different locations, when their detection outputs are averaged, the signal from the false positives decreases while the signal from the true positive lesions prevails, leading to improved performance.

Figure 7:
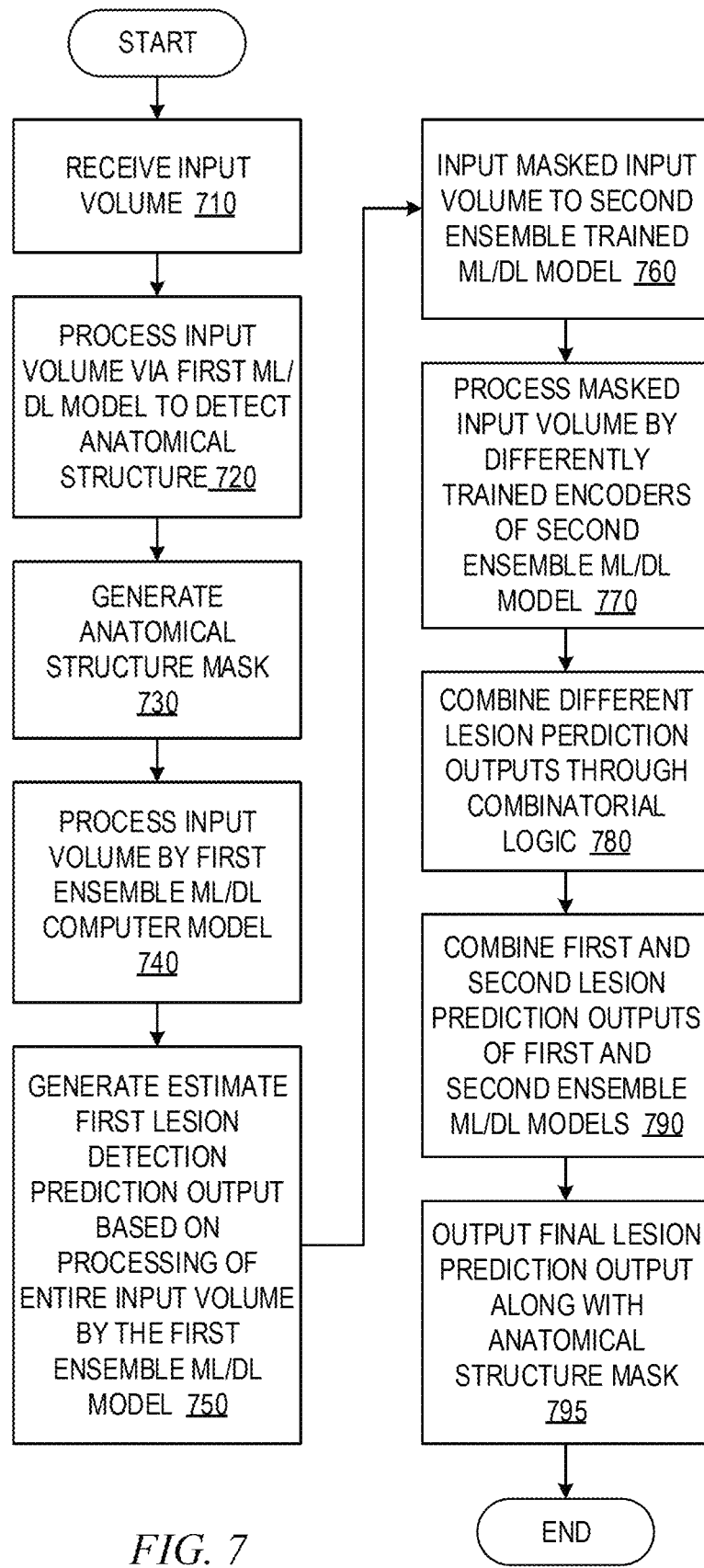
FIG. 7 is a flowchart outlining an example operation of liver/lesion detection logic in an AI pipeline in accordance with one illustrative embodiment.

FIG. 7 is a flowchart outlining an example operation of liver/lesion detection logic in an AI pipeline in accordance with one illustrative embodiment. As shown in FIG. 7, the operation starts by receiving the input volume (step 710) and performing anatomical structure detection, e.g., liver detection, using a first trained ML/DL computer model, such as a U-Net computer model configured and trained to identify the anatomical structure (e.g., liver) (step 720). The result of the anatomical structure detection is a segmentation of the input volume to identify a mask for the anatomical structure, e.g., liver mask (step 730). The input volume is also processed via a first trained ML/DL computer model of an ensemble, which is specifically configured and trained to perform lesion detection (step 740). The first trained ML/DL computer model generates a first set of lesion detection prediction outputs based on its processing of the input volume (step 750).

A second trained ML/DL computer model of the ensemble receives a masked input generated by applying the generated anatomical structure mask to the input volume and thereby identify portions of the medical images in the input volume that correspond to the anatomical structure of interest (step 760). The second trained ML/DL computer model processes the masked input via two different decoders having two different and competing loss functions, e.g., one that penalizes errors in false positive lesion detection and another that penalizes errors in false negative lesion detection (step 770). The result is two sets of lesion predictions outputs which are then combined through combinational logic to generate a lesion prediction output of the second ML/DL computer model (step 780). The second lesion prediction output is resampled if necessary and combined with the first lesion prediction output generated by the first ML/DL computer model of the ensemble to generate a final lesion prediction output (step 790). The final lesion prediction output is then output along with the anatomical structure mask (step 795) and the operation terminates.

Lesion Segmentation

As described previously, through the operation of the various ML/DL computer models and stages of logic of the AI pipeline including body part detection, body part of interest determination, phase classification, anatomical structure of interest identification, and anatomical structure/lesion detection, a lesion prediction output is generated. For example, in the AI pipeline 100 shown in FIG. 1, the results of the liver/lesion detection stage 130 of the AI pipeline 100 includes one or more contours (outlines) of the liver, as well as a detection map identifying portions of medical imaging data elements corresponding to detected lesions 135, e.g., a voxel-wise map of liver lesions detected in the input volume 105. The detection map is then input to a lesion segmentation stage 140 of the AI pipeline 100.

As mentioned previously, the lesion segmentation logic, e.g., lesion segmentation stage 140 in FIG. 1, uses a watershed technique and corresponding ML/DL computer model to partition the detection map to generate image element partitioning of the medical images (slices) of the input volume. The liver lesion segmentation stage also provides other mechanisms, such as one or more other ML/DL computer models, which identify all of the contours corresponding to lesions present in slices of the input volume based on the image element partitioning, and performs operations to identify which contours correspond to the same lesion in three dimensions. The lesion segmentation stage further provides mechanisms, such as one or more additional ML/DL computer models, which aggregate correlated lesion contours to generate three dimensional partitioning of lesions.

The lesion segmentation uses in-painting of lesion image elements and non-liver tissues represented in the medical images so as to focus on each lesion individually and performs active contour analysis. In this way, individual lesions may be identified and processed without biasing the analysis due to other lesions in the medical images or biasing due to portions of the image outside the liver. The results of the lesion segmentation is a listing of lesions with their corresponding outlines or contours in the input volume.

FIG. 8 depicts a block diagram of an overview of the aspects of a lesion segmentation process performed by the lesion segmentation logic in accordance with one illustrative embodiment. As depicted in FIG. 8, lesion segmentation encompasses mechanisms for partitioning two-dimensional detections, i.e. detections of lesions in two-dimensional slices, slice-wise (block 810), connecting two-dimensional lesions along the z-axis (block 820), and refining contours slice-wise (block 830). Each of these blocks will be described in greater detail hereafter with regard to subsequent figures. The segmentation process shown in FIG. 8 is implemented as a process for identifying all lesions in a given input volume under analysis and distinguishing between lesions that are close to one another in the images (slices) of the input volume. For example, two lesions that appear to merge in pixel terms in one or more images may need to be identified as two different regions or distinct lesions for purposes of performing other downstream processing of detected lesions, such as during lesion classification, and in separate identification of lesions in the output of a list of lesions for downstream computing system operations, such as providing a medical viewing application, performing treatment recommendation operations, performing decision support operations, and the like.

As part of the partitioning of the 2D images slice-wise in block 810, a mechanism of the illustrative embodiments uses an existing watershed technique to partition the detection map from the previous lesion detection stage of the AI pipeline, e.g., the detection map 135 generated by the liver/lesion detection logic 130 of the AI pipeline 100 in FIG. 1. The watershed algorithm requires the definition of seeds to perform mask partitioning. It will split a mask into as many regions as there are seeds such that every region has exactly one seed sitting roughly at its center as shown in FIGS. 10A and 10C. In automatic segmentation, seeds in a mask can be obtained as the local maxima of its distance map (distance to the mask contour). However, such an approach is prone to noise and may lead to too many seeds, thereby over-splitting the mask. Therefore, we need to edit the partition by regrouping some of its regions. Considering the empirical observations that most lesions are of a bubble shape, the guiding principle for region regrouping is to make the resulting new region roughly circular. For example, for the mask shown in FIG. 10C, the mechanism will merge the two regions identified respectively by seed 1051 and 1061, thereby producing a new mask partition comprising of only two roughly round regions. Thus for a detected lesion defined in detection map 135, such as the lesion shown on the left side of FIG. 9, described thereafter, it may be segmented into a few bubble-shaped lesions, as shown on the right side of FIG. 9. They will be interpreted as cross sections of 3D lesions on the slice.

Watershed segmentation is a region-based method that has its origins in mathematical morphology. In watershed segmentation, an image is regarded as a topographical landscape with ridges and valleys. The elevation values of the landscape are typically defined by the gray values of the respective pixels or their gradient magnitudes, thus considering a two-dimensional as a three-dimensional representation. The watershed transform decomposes an image into "catchment basins." For each local minimum, a catchment basin comprises all points whose path of steepest descent terminates at this minimum. Watersheds separate basins from one another. The watershed transform decomposes an image completely and assigns each pixel into either a region or a watershed.

Watershed segmentation requires selection of at least one marker, referred to as a "seed" point, interior to each object of the image. Seed points may be chosen by an operator. In one embodiment, the seed points are chosen by an automatic procedure that considers the application-specific knowledge of the objects. Once the objects are marked, they can be grown using a morphological watershed transformation, to be described in further detail below. Lesions typically have a "bubble" shape. The illustrative embodiment provides a technique for merging watershed partitioned regions based on this assumption.

Thereafter, in block 820, a mechanism of the illustrative embodiments aggregates the voxel partitioning on each of the slices along the z-direction to produce a three-dimensional output. Therefore, the mechanism must determine if two sets of image elements, e.g., voxels, in different slices belong to the same lesion, i.e., whether they are aligned in three-dimensions. The mechanism computes measurements between lesions in adjacent slices based on intersection and union of the lesions and applies a regression model to determine whether the two lesions in the adjacent slices are part of the same region. One may view each lesion as a set of voxels, and the mechanism determines an intersect of two lesions as an intersect of the two sets of voxels and determines a union of two lesions as a union of the two sets of voxels.

This results in a three-dimensional partitioning of the lesions; however, the contours may not fit the actual image well. There may be over segmented lesions. The illustrative embodiments propose using active contouring, which is a traditional framework to tackle the segmentation problem. Such an algorithm seeks to edit a contour iteratively to make it fit image data better and better and, in the meantime, ensure it maintains certain desirable properties such as shape smoothness. In block 830, a mechanism of the illustrative embodiments initializes the active contours with partitioning obtained from the first and second stages 810, 820 and focuses on one lesion at a time; otherwise, running active contours or random segmentation methods on close lesions may result in their being merged into one contour again, which is counterproductive because this amounts to essentially erasing the benefits brought by the previous partitioning stage. The mechanism focuses on one lesion and performs "inpainting" on lesion voxels and non-liver tissues in the vicinity of the lesion under focus.

The chaining of these three stages of processing allows processing that is unbiased by other lesions in the image or by pixels or lesions outside the liver.

Partitioning 2D Detections Slice-Wise

FIG. 9 depicts a result of lesion detection and slice-wise partitioning in accordance with one illustrative embodiment. As seen on the left side of FIG. 9, a lesion area 910 is detected through the previous AI pipeline processes described above and may be defined in the output of the contours and detection map, e.g., 135 in FIG. 1, from the lesion detection logic, e.g., 130 in FIG. 1. In accordance with one illustrative embodiment, the logic of block 810 in FIG. 8 attempts to partition this region into three lesions 911, 912, and 913, as shown on the right side of FIG. 9. The partitioning mechanism of the illustrative embodiment is based on an existing watershed technique that operates to partition the detection map from the previous lesion detection stage of the AI pipeline. Watershed algorithms are used in image processing primarily for segmentation purposes. The philosophy behind these known watershed algorithms is that grayscale images can be viewed as a topographic surface where high intensity denotes peaks and hills, while low intensity denotes valleys. The watershed technique starts filling every isolated valley (local minima) with different colored water (labels). As the water rises, depending on the peaks (gradients) nearby, water from different valleys, with different colors, will start to merge. To avoid this, barriers are built in locations where water merges. The work of filling water and building barriers continues until all the peaks are under water at which point the barriers that were created gives the segmentation result. Again, watershed techniques are generally known and, thus, a more detailed description is not provided herein. Any known technique for partitioning 2D images slice-wise may be used without departing from the spirit and scope of the present invention.

In the context of lesion segmentation, the empirical observation that most lesions are of circular shape strongly suggests that a partition that results in a set of round regions is likely to be a good one. However, as previously stated, the quality of watershed type partition hinges on that of the seeds. As a matter of fact, an arbitrary set of seeds need not lead to a set of round regions. For instance, FIG. 10C shows a watershed partition induced by 3 seeds that contains only one roughly circular region. The other two are not circular. However, their union is again roughly circular. Such a configuration is termed over-splitting because the slanted split in the figure breaks an otherwise circular region into two smaller, no circular regions. Therefore, it is desirable to have an algorithm able to correct over-splitting. The seed relabeling mechanism does this by merging a few over-split regions to form a coarser partition containing only round shaped regions. For instance, the mechanism decides for the partition in FIG. 10C that merging two regions identified by seed 1051 and 1061 makes a more circular new region.

The illustrative embodiment merges regions in a partition into rounder and larger regions that may correspond to a physical lesion. The partition breaks an area into smaller regions, or as described herein, the partition breaks a mask into smaller regions. In terms of contours, a partition thus produces a set of smaller contours from a large contour (see FIG. 9 left to right).

Seeds are obtained by extracting local maxima from a distance map computed from an input mask to partition. The map measures for each pixel its Euclidean distance to the mask contour. Depending on the topology of the input mask, local maxima derived from this distance map may lead to an overly fragmented partition by watershed algorithms. In this case, watershed is said to over-split and tends to produce regions that are not circular, which may be desirable in some applications, but is not ideal for lesion segmentation. In FIG. 10C, we show a synthetic input mask whose distance map has three local maxima. Watershed thus results in a partition which contains three regions, of which only one is roughly circular (corresponding to seed 1071). The other two are not. The region having seed 1051 is only half circular. The seed relabeling mechanism then checks all seed pairs and determines that two regions corresponding to seed 1051 and 1061 should be merged as together they will form a more perfect bubble. Such an operation leads to a new partition containing only two regions, and both are roughly circular in shape.

Local maxima are points that have the largest distance to the contour compared to its immediate neighbor. A local maximum is a point, and its distance to the contour is known. As a result, the mechanism of the illustrative embodiment can draw a circle centered on this point. The circle's radius is the distance. For two local maxima, the mechanism can thus compute the overlap their respective circles. This is depicted in FIG. 10A and FIG. 10B.

The seed relabeling determines whether to merge two regions as follows. For two regions whose associated seeds are immediate neighbors, the merge will occur; otherwise, the mechanism bases its decision on a hypothesis testing procedure. For example, with reference to FIG. 10A, the depicted example describes a situation where a distance map yields two distinct local maxima, which leads to the hypothesis that each maximum represents the center of a distinct circular lesion. Note that the distance map also allows the mechanisms of the illustrative embodiments to tell how far the maxima are from the contour (boundary). This distance is represented in FIG. 10B by the dotted segments connecting a maximum and a point on the contour. Therefore, if the hypothesis holds, one can infer the spatial extents of these two lesions due to the assumption that lesions are of approximately round or "bubble" shape. This allows the mechanisms of the illustrative embodiments to draw two completed circles as shown in FIG. 10B. From this, the mechanism then measures the two circles' overlap (e.g., with the classic dice metric) and compares it to a predetermined threshold. If the overlap metric's value is greater than the threshold, the mechanism concludes that the two bubbles overlap too much to be distinct and a merge will take place. In other words, the mechanism of the illustrative embodiment then concludes that the two local maxima correspond to two "centers" of the same lesion. However, in conventional watershed, no such seed (i.e., maxima) relabeling mechanism exists. Thus, mask over-splitting occurs often.

The overlap can be measured in a number of ways. In one example embodiment, the mechanism uses the dice coefficient. For two full circles corresponding to two local maxima as shown in FIG. 10B, the mechanism may calculate the dice metric of these two circles. In this way, the mechanism may learn from the training dataset what the optimal threshold to apply in practice such that once the dice metric is greater than the threshold, the two local maxima are actually centers of the same lesion.

FIGS. 10C and 10D provide an example of another lesion mask shape which differs from that of FIGS. 10A and 10B in that two partially merging circles are closer to one another in FIG. 10A than in FIG. 10C. Due to the distance map, which may be very sensitive to the mask shape, there are three seeds in the example lesion mask shape of FIG. 10C. Following the above reasoning, the lesion splitting algorithm will split the lesions represented in FIG. 10C into two separate lesions, but not three separate lesions as would occur in the watershed technique without seed relabeling.

In FIGS. 10C and 10D, seeds 1051 and 1061 represent a more extreme case than the one described in FIGS. 10A and 10B. Without seed relabeling technique of the illustrative embodiments, a splitting will take place (represented by the slanted solid line) to separate them. But with the seed relabeling mechanism of the illustrative embodiments, this undesirable outcome can be effectively avoided. To the contrary, since seed 1071 lies sufficiently far away from seed 1051 and 1061, the same hypothesis testing procedure described above will help accept the hypothesis that seed 1071 corresponds to the center of a distinct bubble, leading to the vertical split as shown in FIGS. 10C and 10D. Equivalently, this translates into a different label for seed 1071 from the one assigned to seed 1051 and 1061. However, similar to the situation in FIGS. 10A and 10B, the hypothesis testing procedure of the seed relabeling technique of the illustrative embodiments will determine that the seeds 1051 and 1061 correspond to the same lesion.

Figure 11A:
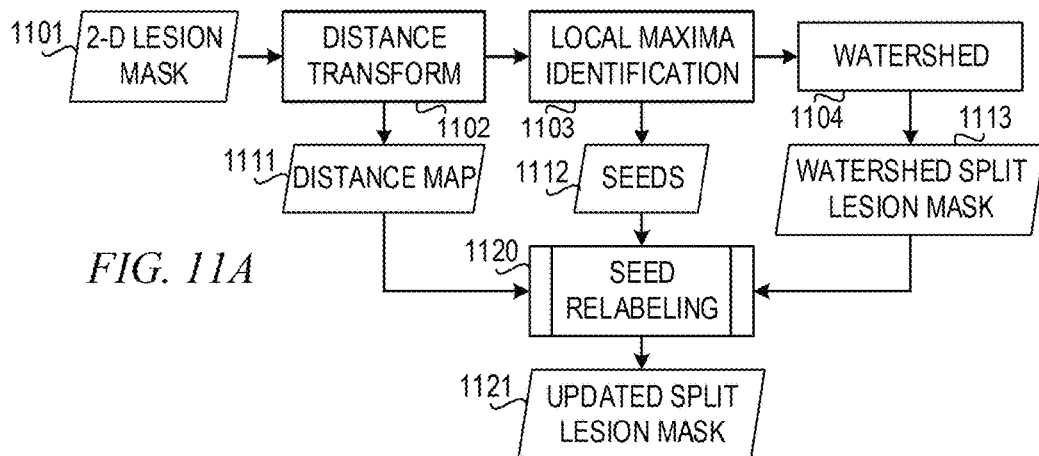
FIG. 11A is a block diagram illustrating a mechanism for lesion splitting in accordance with one illustrative embodiment.

FIG. 11A is a block diagram illustrating a mechanism for lesion splitting and relabeling in accordance with one illustrative embodiment. As shown in FIG. 11A, the mechanism, which may be implemented as a computer model comprising one or more algorithms, machine learning computer models, and the like, executed by one or more processors of one or more computing devices and which operates on input volumes of one or more medical image data structures, receives a two-dimensional lesion mask 1101 and performs a distance transform (block 1102) to generate distance map 1111. The distance transform (block 1102) is an operation performed on a binary mask which computes, for each point in the lesion mask, its shortest distance to the mask contour (boundary). The more one moves towards the interior of the lesion mask, the further one will be away from its contour (boundary). Thus, the distance transform identifies the lesion mask's center points, i.e., those points with a larger distance than others. In one embodiment, the mechanism optionally performs Gaussian smoothing on the distance map 1111.

The mechanism then performs local maxima identification (block 1103) to generate seeds 1112. As described above, these local maxima are the points in the distance map 1111 that have a highest distance from a contour or boundary. The mechanism performs the watershed technique (block 1104) based on seeds 1112 to generate a watershed split lesion mask 1113. As explained above, this split lesion mask 1113 may be over-split, resulting in regions that do not conform to the assumed bubble shape of a lesion. Therefore, the mechanism performs seed relabeling (block 1120) based on the distance map 1111, seeds 1112, and the split 2D lesion mask 1113 to generate updated split lesion mask 1121. The seed relabeling is described in further detail below with reference to FIG. 11B. The resulting updated split lesion mask 1121 will have regions that have been merged to form regions that more accurately conform to bubble shapes assumed for lesions.

Figure 11B:
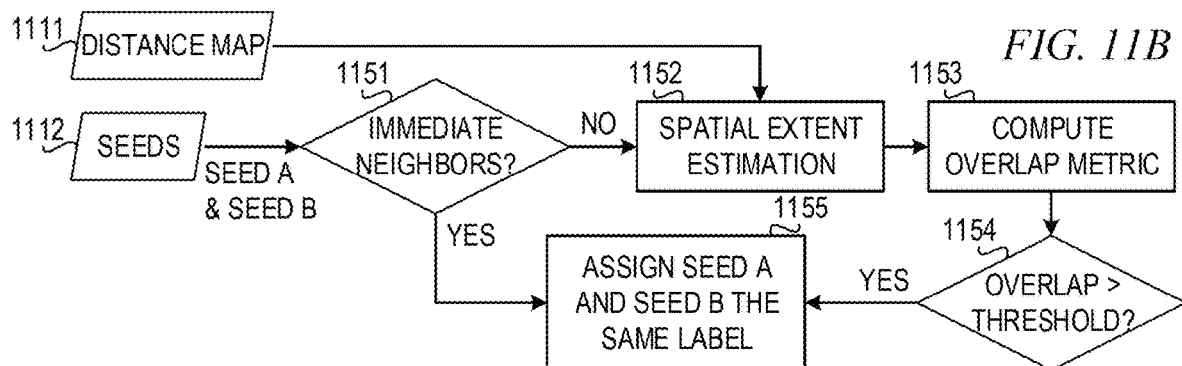
FIG. 11B is a block diagram illustrating a mechanism for seed relabeling in accordance with one illustrative embodiment.

FIG. 11B is a block diagram illustrating a mechanism for seed relabeling in accordance with one illustrative embodiment. As shown in FIG. 11B, the mechanism, which may be implemented as a computer model comprising one or more algorithms, machine learning computer models, and the like, executed by one or more processors of one or more computing devices and which operates on input volumes of one or more medical image data structures, receives distance map 1111 and seeds 1112. More specifically, the mechanism considers each pair of seeds (seed A and seed B) in seeds 1112. The mechanism determines whether seed A and seed B are immediate neighbors (block 1151). If seed A and seed B are immediate neighbors, then the mechanism assigns seed A and seed B the same label (block 1155). In other words, seed A and seed B are grouped to represent a single region.

If seed A and seed B are not immediate neighbors in block 1151, then the mechanism performs spatial extent estimation (1152) based on the distance map 1111 and determines pairwise affinity for seed A and seed B, as described below. In accordance with the illustrative embodiment, spatial extent estimation assumes that a region is a "bubble" shape. Thus, the mechanism assumes each seed represents a circle with the distance from the distance map as the radius of the circle.

Then, the mechanism computes an overlap metric (block 1153) for the circles represented by seed A and seed B. In one example embodiment, the mechanism uses a dice metric as follows:

$$\frac{2|A \cap B|}{|A| + |B|}$$

where $|A|$ denotes the area of the circle represented by seed A, $|B|$ denotes the area of the circle represented by seed B. Similarly, $|A \cap B|$ denotes the area of the intersection of A and B. In an alternative embodiment, the mechanism may compute the overlap metric as follows:

$$\frac{|A \cap B|}{|A \cup B|}$$

where |A| denotes the area of the circle represented by seed A, |B| denotes the area of the circle represented by seed B, |A∩B| denotes the area of the intersection of A and B, and |A∪B| denotes the area of the union of A and B.

The mechanism determines whether the overlap metric is greater than a predetermined threshold (block 1154). If the overlap metric is greater than the threshold in block 1154, then the mechanism merges the corresponding regions (block 1155) in split 2D lesion mask 1113.

If the affinity between two seeds is greater than the threshold, then they are assigned the same label. Otherwise, at this stage, it is not known whether they should belong to the same group or not. This decision is left to the label propagation stage (block 1512 in FIG. 15), the same module used in z-wise connection, to be described below.

In a situation where we have more than two seeds, the same operation of FIG. 11B is repeated for all seed pairs before label propagation, which produces seed groups. For instance, there are situations where seed pair (a, b) and (b, c) are determined to belong to the same group, whereas seed pair (a, c) fails the test as shown in FIG. 11B. Then the label propagation will have to put a, b, c in the same group, that is, regions corresponding to seeds a and c will still merge. However, if there are seeds a, b, c, and d and affinity computation (performed on six pairs in total) shows that only (a, b) and (c, d) pass the test, then label propagation would result in two groups, containing respectively (a, b) and (c, d). Therefore, if a seed pair fails the test, it means that it is not known whether they should be put in the same group, but not they should belong to different groups.

For example, in FIG. 10C, there are 3 seed pairs (1051-1061, 1051-1071, 1061-1071) and the mechanism should determine that seed 1051 and 1061 should be assigned the same label (belonging to the same group). A label propagation step will then cluster these 3 seeds into 2 groups, the first containing only 1071 and the second having both 1051 and 1061.

Figure 12:
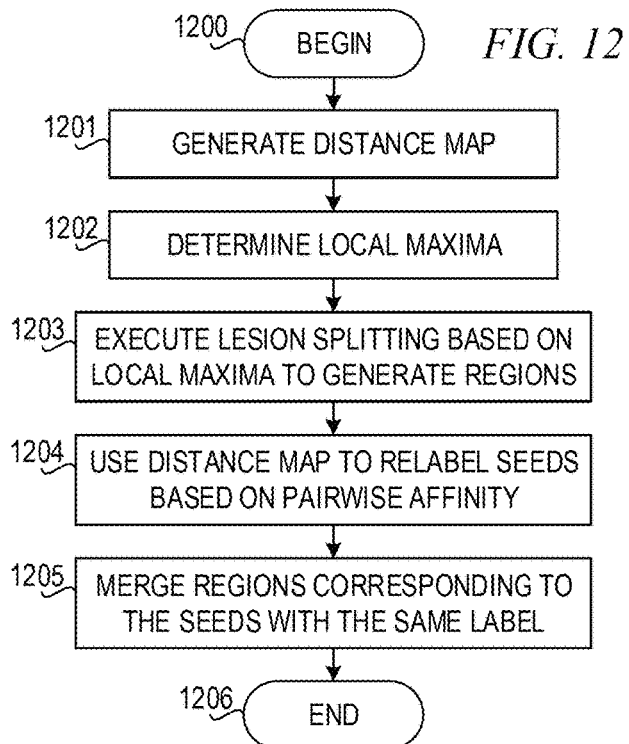
FIG. 12 is a flowchart outlining an example operation of lesion splitting in accordance with one illustrative embodiment.

FIG. 12 is a flowchart outlining an example operation for lesion splitting in accordance with an illustrative embodiment. The operation outlined in FIG. 12 may be performed by the mechanisms described above with regard to FIGS. 11A-11B. As shown in FIG. 12, the operation begins (step 1200), and the mechanism generating a distance map for a two-dimensional lesion mask (block 1101). As discussed above, this distance map may be generated by performing a distance transformation operation on the two-dimensional lesion mask and optionally performing Gaussian smoothing to remove noise. The mechanism then uses local maxima identification to generate groupings of data points, e.g., the local maxima for each group (step 1202). The mechanism executes lesion splitting based on local maxima to generate regions (step 1203). The mechanism then uses the distance map to relabel seeds based on pairwise affinity (step 1204). Then, the mechanism merges regions corresponding to the seeds with the same label (step 1205). It should be appreciated that due to the seed relabeling performed by the mechanisms of the illustrative embodiments, the split lesion mask output in step 1205 will not have the over-splitting problems associated with the watershed technique due to the wrong labels being associated with the data points associated with each of the lesion shapes, as previously discussed above. Thereafter, the operation ends (step 1206).

Z-Wise Connection of Lesions

The above process for lesion splitting and seed relabeling may be performed with regard to each of the two-dimensional images, or slices, of the input volume to thereby generate appropriately labeled lesion masks for each of the lesions represented in the corresponding two-dimensional images. However, the input volume represents a three-dimensional representation of the biological entity's internal anatomical structure and lesions that may appear to be associated with the same lesion, when considered in three-dimensions, may in fact be associated with different lesions. Thus, in order to be able to properly identify separate lesions within the biological entity as represented in three-dimensions of the input volume, the illustrative embodiments provide a mechanism for connecting two-dimensional lesions along the z-axis, i.e., in three-dimensions.

The mechanism that performs connection of the two-dimensional lesions along the z-axis, referred to as the z-wise connection of lesions, includes a logistic regression model that executes on the split lesion output generated by the mechanisms described above, to determine three-dimensional z-wise lesion detection. The mechanism connects two lesions in neighboring image slices. Two lesions are connected when the logistic regression model determines that they represent the same lesion. For example, for any two-dimensional lesions on neighboring image slices, i.e. slices that have consecutively ordered z-axis coordinates along a z-axis in a three-dimensionally organized collection of the slices, the mechanism determines whether theses two-dimensional lesions belong to the same three-dimensional lesion or not, as will be described hereafter.

Figure 13A:
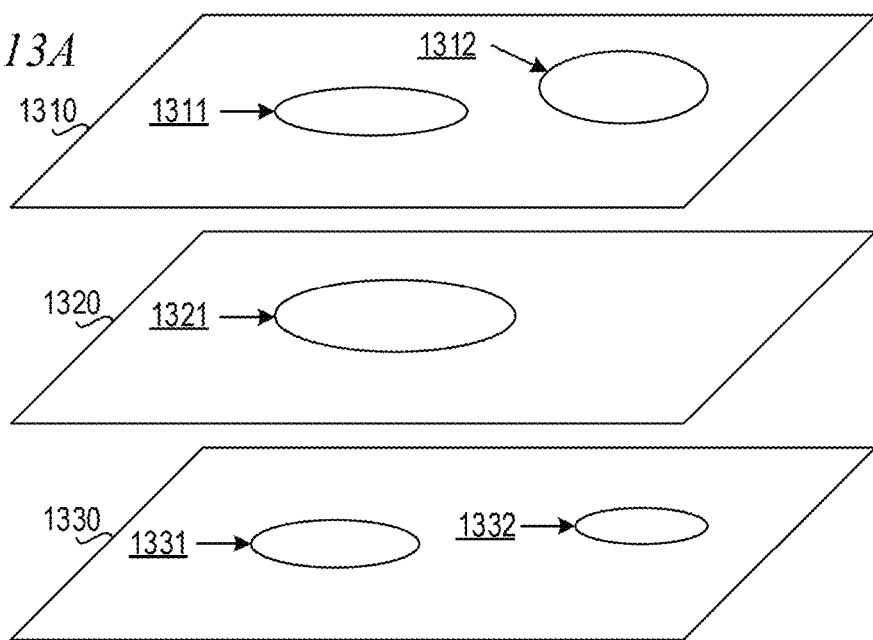
FIGS. 13A-13C illustrate z-wise connection of lesions in accordance with one illustrative embodiment.
Figure 13B:
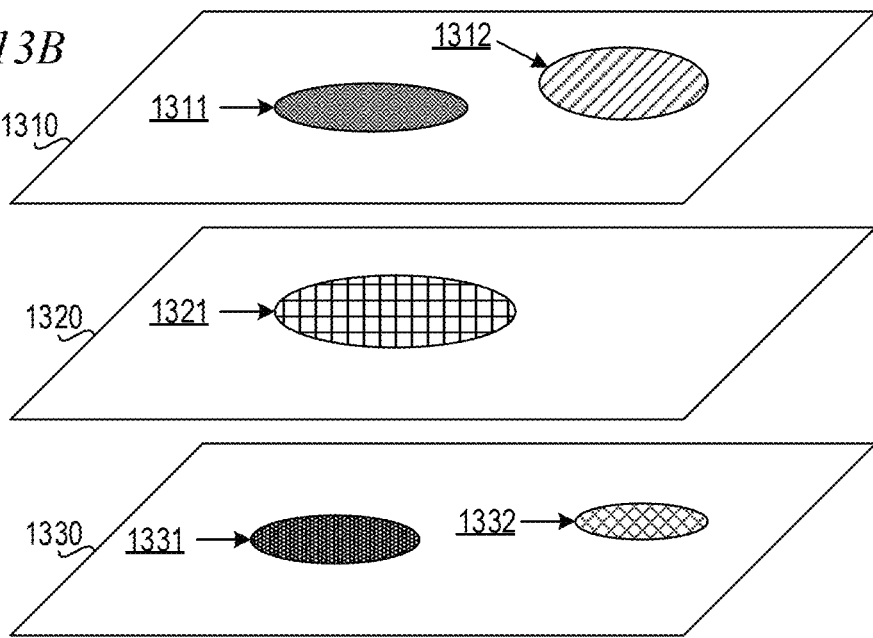
Figure 13C:
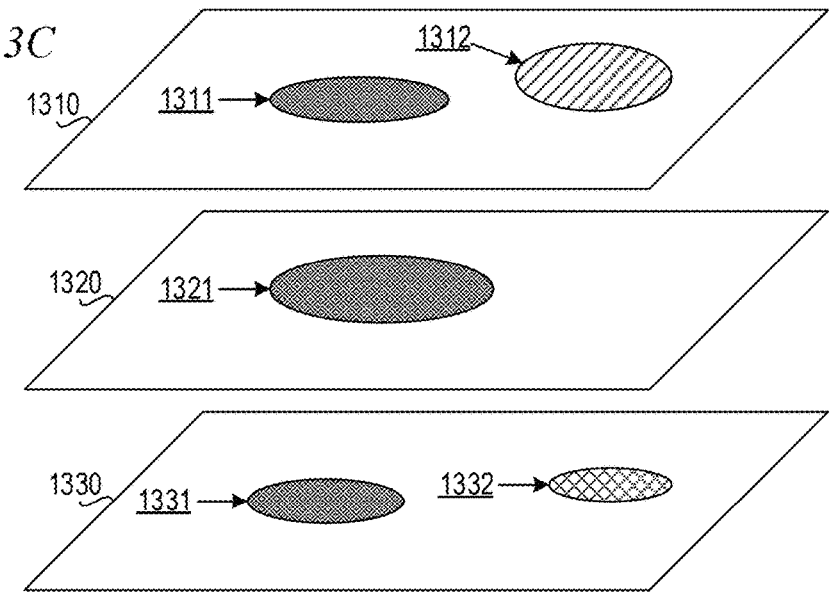

FIGS. 13A-13C illustrate a process for z-wise connection of lesions in accordance with one illustrative embodiment. FIG. 13A depicts a lesion mask input. FIG. 13B depicts the lesions after slice-wise lesion splitting, which may employ the relabeling improved lesion splitting mechanisms of the illustrative embodiments as described previously. As shown in FIGS. 13A-13B, slice 1310 has lesions 1311 and 1312, slice 1320 has lesion 1321, and slice 1330 has lesions 1331 and 1332. The z-wise connection of lesions mechanism, i.e. the logistic regression model, executes on the split lesion masks for each neighboring pair of the slices in the input volume so as to compare each lesion in a given slice to each lesion in the paired neighboring slice. For example, the z-wise connection of lesions mechanism compares lesion 1311 (lesion A) in slice 1310 to lesion 1321 (lesion B) in slice 1320. For each comparison, the mechanism treats each lesion as a set of voxels and determines the intersection between lesion A (set of voxels in lesion A) and lesion B (set of voxels in lesion B) with respect to the size of lesion A and with respect to the size of lesion B. The z-wise connection of lesions mechanism determines whether lesion A and lesion B are connected using the logistic regression model based on two overlap ratios, as follows:

$$r_0 = \frac{|A \cap B|}{\min(|A|, |B|)}, r_1 = \frac{|A \cap B|}{\max(|A|, |B|)}$$

Where |A| denotes the area of the circle represented by seed A, |B| denotes the area of the circle represented by seed B, and |A∩B| denotes the area of the intersection of the circles represented by seed A and seed B. The mechanism uses these two ratios, as input features, to train a logistic regression model to determine the probability that lesion A and lesion B are connected. That is, using a machine learning process, such as previously described above, the logistic regression model is trained on volumes of training images to generate predictions with regard to the probability that, in each pairwise combination of slices in each training volume, whether a lesion in one slice is the same or different lesion as a lesion represented in a neighboring slice. This prediction is compared to a ground truth indication of whether the lesions are the same or different lesions in order to generate a loss or error. The operational parameters, e.g., coefficients or weights, of the logistic regression model are then modified so as to reduce this loss or error until a predetermined number of epochs of training have been performed or a predetermined stopping condition is satisfied.

Logistic regression models are widely used for solving binary classification problems. In the context of the illustrative embodiments, however, this logistic regression model predicts a probability for two cross-sections of lesions to be part of the same lesion. To this end, the logistic regression uses the two overlap ratios $r_0$ and $r_1$, as mentioned previously. Specifically, the logistic model learns to linearly combine the two features as follows:

$$f(r_0, r_1; c_0, c_1, b) = \frac{1}{1 + \exp(c_0 r_0 + c_1 r_1 + b)}$$

in which ($c_0$, $c_1$, b) are the operational parameters to be learned from the training volumes via the machine learning training operation. Notation-wise, $r_0$ and $r_1$ denote respectively minimum overlap ratio and maximum overlap ratio. The state of the operational parameters after training of the logistic regression model may be denoted by ($c_0^*$, $c_1^*$, $b^*$). At inference time, i.e., after the training of the logistic regression model, when processing a new input volume of images (slices) a threshold t is set so that two cross-sections are deemed as belonging to the same lesion if, and only if, the relation $f(r_0, r_1; c_0^*, c_1^*, b^*) > t$ holds, i.e. the predicted probability is higher than the set threshold.

There are two extreme cases. First, when the threshold t is set to 0, the z-wise connection mechanism of the illustrative embodiments always determines that the lesions are the same lesion, i.e. that the cross-sections are connected. Then both the true positive rate and false positive rate will be 1. Second, when the threshold t is set to 1, the z-wise connection mechanism will not identify any cross-sections of lesions to be connected. In this case, both true positive rate and false positive rate will be 0. Therefore, only when a threshold t is in the interval (0, 1), will the logistic regression model make a determination as to whether lesion cross-sections are associated with the same lesion or not across neighboring slices. With an ideal logistic regression model, the true positive rate is equal to 1 (all the true connections are identified) and at the same time, false positive rate is 0 (zero false connection is made).

Thus, once the logistic regression model is trained, new pairs of slices may be evaluated in this manner by calculating these ratios for the pairs and inputting them into the trained logistic regression model as input features so as to generate predictions for each of these pairs and then, if the predicted probability is equal to or greater than a predetermined threshold probability, the lesions A and B are considered to be associated with the same lesion in three dimensions. Appropriate relabeling of the lesions across the slices may then be performed so as to properly associate lesions in two-dimensional slices with the same lesion representation in other neighboring slices and thereby identify three-dimensional lesions within the input volume.

There are rationales that support the two ratio input features used to train the logistic regression model. For example, if lesions A and B are sufficiently different in size, then it is unlikely they are part of the same lesions. Moreover, if lesions A and B do not intersect, as with lesion 1312 in slice 1310 and lesion 1321 in slice 1320, then the features $r_0$, $r_1$ will have a zero value. As noted above, the logistic regression model performs the regression given the two feature values $r_0$, $r_1$ and outputs a probability value between 0 and 1 that represents a likelihood lesion A and lesion B are part of the same lesion.

FIG. 13C depicts a cross-section connection between slices in accordance with one illustrative embodiment. As shown in FIG. 13C, the mechanism determines that lesion 1311 in slice 1310 and lesion 1321 in slice 1321 are part of the same lesion by executing the trained logistic regression model of the illustrative embodiments that predicts lesion commonality based on overlap ratios as discussed above. The mechanism also determines that lesion 1321 in slice 1320 and lesion 1331 in slice 1330 are part of the same lesion in a similar manner. Thus, the mechanism propagates the intersecting lesions along the z-axis and performs z-axis connection of lesions.

Based on the pairwise evaluation of slices in the input volume with regard to identifying z-wise connection of lesions across the two-dimensional slices, and the determination by the trained logistic regression model whether lesions are connected or not along the z-axis, relabeling of lesions may be performed so as to make sure that the same label for a lesion is applied to each of the lesion masks present in each of the slices of the input volume, e.g., all of the lesion masks across a set of slices in the input volume, where the lesions masks are determined by the logistic regression model to be associated with the same lesion A, may be relabeled to specify that they are part of the same lesion A. This may be performed for each lesion cross-section in each of the slices of the input volume to thereby generate three-dimensional associations of lesion masks for one or more lesions present in the input volume. This information may then be used to represent or otherwise process lesions, such as in later downstream computing system operations, in three-dimensions since all of the cross-sections associated with the same lesion are properly labeled in the input volume.

Figure 14A:
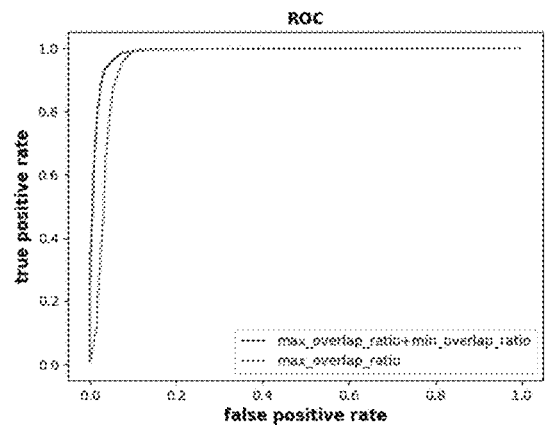
FIGS. 14A and 14B illustrate results of a trained model for z-wise lesion connection in accordance with one illustrative embodiment.
Figure 14B:
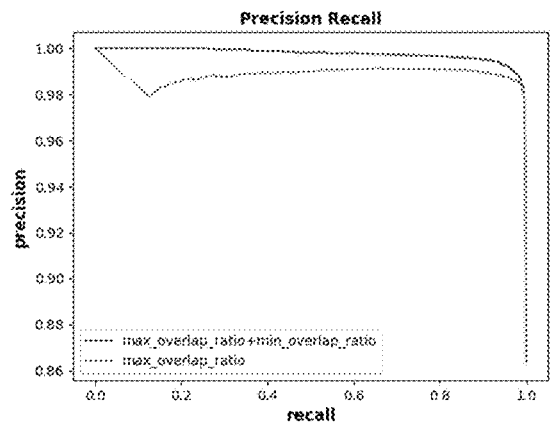

FIGS. 14A and 14B illustrate results of the trained logistic regression model in accordance with one illustrative embodiment. FIG. 14A illustrates a receiver operating characteristic (ROC) curve for a maximum overlap ratio ($r_0$)+ minimum overlap ratio ($r_1$) metric, and for a maximum overlap ratio metric. A ROC curve is a graphical plot that illustrates the diagnostic ability of a binary classifier system as its discrimination threshold is varied. The ROC curve is created by plotting the true positive rate (TPR) against the false positive rate (FPR) at various threshold settings. FIG. 14B illustrates a precision-recall curve for a maximum overlap ratio+minimum overlap ratio metric, and for a maximum overlap ratio metric. A precision-recall curve is a plot of the precision (y-axis) and the recall (x-axis) for different thresholds, much like the ROC curve, where precision is the fraction of relevant instances among retrieved instances, and recall (or sensitivity) is the fraction of the total amount of relevant instances that were actually retrieved. As shown in these figures, the two-feature logistic model outperforms its one-feature counterpart. Both features thus bring valuable information for this prediction task.

Looking at the maximum overlap ratio ($r_0$)+minimum overlap ratio ($r_1$) metric curve in FIG. 14A, it can be seen that with an appropriate threshold t, the trained logistic regression model is able to produce a true positive rate ~=95% at the cost of a false positive rate at roughly 3%. Looking at FIG. 14B, the depicted plot assess the trained logistic regression model in terms of precision and recall, and shows that both measures are able to achieve very good results with the selection of a proper threshold t.

Figure 15:
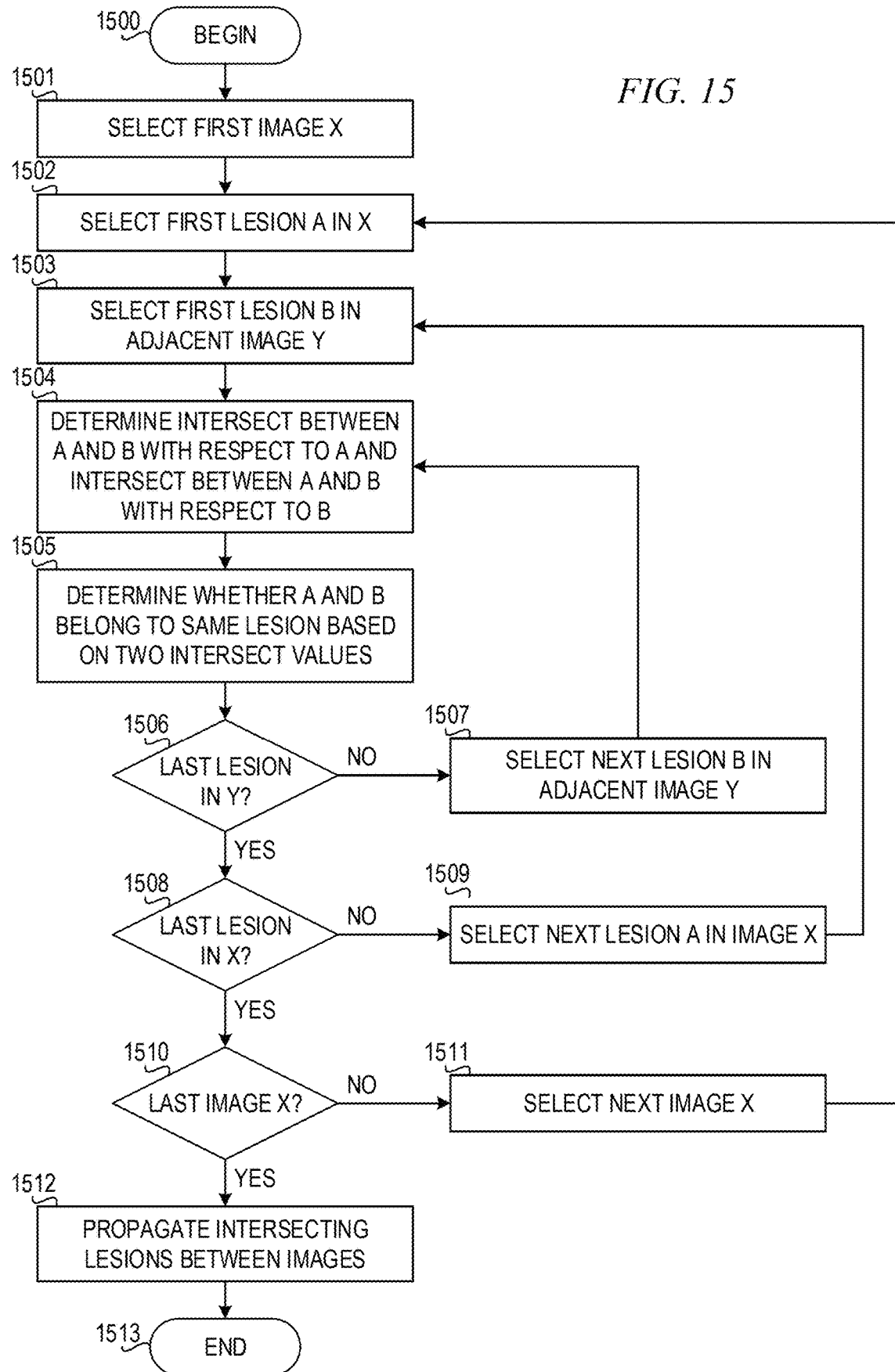
FIG. 15 is a flowchart outlining an example operation of a mechanism for connecting two-dimensional lesions along the z-axis in accordance with one illustrative embodiment.

FIG. 15 is a flowchart outlining an example operation of a mechanism for connecting two-dimensional lesions along the z-axis in accordance with one illustrative embodiment. As shown in FIG. 15, the operation begins (step 1500), and the mechanism selects a first image X from the input volume (step 1501) and selects a first lesion A in image X (step 1502). In some illustrative embodiments, the images or slices in the input volume may be processed using the splitting and relabeling mechanism described previously, however this is not required. To the contrary, the mechanisms of the illustrative embodiments directed to the z-wise connection of lesions may in fact be performed with any input volume in which lesion masks have been identified.

The z-wise connection mechanism of the illustrative embodiments then select a first lesion B in an adjacent image Y (step 1503). Then, the mechanism determines an intersect between lesion A and lesion B with respect to lesion A and determines an intersect between lesion A and lesion B with respect to lesion B (step 1504). The mechanism determines whether lesion A and lesion B belong to the same lesion based on the two intersect values by applying the trained logistic regression model to the $r_0$ and $r_1$ features for the intersections of lesion A and lesion B to generate a prediction or probability that lesion A and lesion B are the same lesion and then compare the probability to a threshold probability (step 1505). Based on the results of this determination, the cross-sections of lesions in the images may be labeled or relabeled to indicate whether or not they are part of the same lesion.

The mechanism determines whether lesion B in image Y is the last lesion in image Y (step 1506). If lesion B is not the last lesion, then the mechanism considers the next lesion B in the adjacent image Y (step 1507), and operation returns to step 1504 to determine the intersect between the lesion A and the new lesion B.

If lesion B is the last lesion in the adjacent slice or image Y at step 1506, then the mechanism determines whether lesion A is the last lesion in image X (step 1508). If lesion A is not the last lesion in image X, then the mechanism considers the next lesion A in image X (step 1509), and operation returns to step 1502 to consider the first lesion B in an adjacent image Y.

If lesion A is the last lesion in image X at step 1508, then the mechanism determines whether image X is the last image to consider (step 1510). If image X is not the last image, then the mechanism considers the next image X (step 1511), and operation returns to step 1502 to consider the first lesion A in the new image X.

If image X is the last image to consider at step 1510, then the mechanism propagates intersecting lesions between images along the z-axis, where propagation means that the labels associated with the same lesion as determined through the above process are set to a same value to indicate that they are part of the same lesion (step 1512). This is performed for each separate lesion identified in the input volume such that cross-sections in each of the images that are associated with the same lesion are appropriately labeled and thus, a three-dimensional representation of each lesion is generated through the z-wise connection of the cross-sections. Thereafter, the operation ends (step 1513).

Contour Refinement

The above processes yield accurate results in terms of the number and relative positions of lesions and connecting lesions across two-dimensional spaces (within an image or slice) and three-dimensional spaces (across images or slices in an input volume). However, lesion contours (boundaries) are not always well-defined and require improvement. The illustrative embodiments provide a mechanism for improving lesion contour accuracy. This additional mechanism may be employed with the above described mechanisms as part of lesion segmentation, or may be employed in other illustrative embodiments which do not require the specific lesion detection, lesion splitting and relabeling, and/or z-wise connection mechanisms described above.

Existing contour algorithms only work well when there is a lesion in the middle of the anatomical structure with no surrounding lesions, but perform poorly when there are different circumstances leading to a "leaking" problem where two or more close-by lesions have their initially distinct contours merged into one single all-encompassing contour, thereby completely erasing the benefits brought by the earlier two dimensional lesion mask splitting. In some cases, where the lesion is at the vicinity of the anatomical structure boundary, e.g., the liver boundary, the contouring algorithm distinguishes between pixels of the anatomical structure relative to pixels for other anatomical structures, e.g., organs, in the image, rather than distinguishing one lesion from another, because these are most distinguishable by the contouring algorithm.

Figure 16:
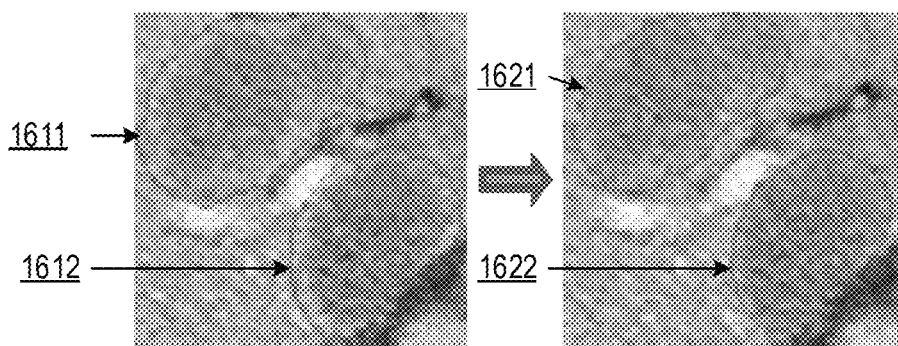
FIG. 16 illustrates an example with contours for two lesions in the same image in accordance with one illustrative embodiment.

The mechanisms of the illustrative embodiment in-paint areas that are not of interest in the images or slices. FIG. 16 illustrates an example with contours for two lesions in the same image in accordance with an illustrative embodiment. On the left side of FIG. 16, an active contour algorithm is used to determine contours 1611 and 1612 for the two lesions. Active contour algorithms are a class of algorithms that make a contour evolve iteratively to fit image content better.

In accordance with the illustrative embodiment, the mechanism in-paints within contour 1612 and non-liver tissue in the vicinity of contour 1611, but not within contour 1611, where the in-painting means that the pixel values for pixels of the contour 1612 and within the contour 1612 and healthy tissue (non-lesion tissue) in the vicinity of contour 1611 are set to a specified value such that they all have a same value. For example, this value may be the average tissue value in the region identified as not being associated with a lesion, i.e. healthy tissue of the anatomical structure, e.g., the liver.

This in-painting may be performed with respect to a selected lesion contour 1611 such that the in-painting is applied to the healthy tissue and other lesions, e.g., lesion 1612, in the image. In this way, the contour and pixels associated with the selected lesion, e.g., 1611, are separately considered from the other portions of the image when re-evaluating the contour 1611. The contour 1611 may then be re-evaluated and a determination may be made as to whether the re-evaluation of the contour 1611 results in an improved definition of the contour 1611. That is, an initial determination of the contrast and variance between pixels associated with the selected lesion contour 1611 and pixels near the selected lesion contour 1611 may be generated. After calculating this contrast and variance prior to in-painting, the in-painting may be performed with respect to the selected lesion 1611 such that pixels associated with other lesion contours, e.g., 1612, and areas of the anatomical structure representing healthy tissues in the image, are in-painted with an average pixel intensity value of the healthy tissue.

The variance of a set of values is determined as follows. Consider a voxel set, comprising of, say n voxels. First, the arithmetic average is computed by summing up their intensity values and then dividing the resulting sum by n. This is denoted the resulting quantity by A. Second, these voxel values are squared individually and then the arithmetic average is computed. The result is denoted as B. The variance is then defined as B−A*A, i.e., the difference between B and the squared A.

Thus, the variance of a set of n values $\{x_1, \ldots, x_n\}$ is defined as follows:

$$\frac{\sum_{i=1}^{n} x_i^2}{n} - \left(\frac{\sum_{i=1}^{n} x_i}{n}\right)^2.$$

The variance is computed between voxels inside and outside a given contour. Voxels inside a counter are those enclosed by the contour, and voxels outside refer to those outside the contour but remaining within a pre-determined distance away from the contour.

The mechanism recalculates the contour 1611 of the selected lesion after the in-painting using an active contouring algorithm as previously described above, and recalculates the contrast and/or variance of the new contour 1611 to determine if these values have improved (higher contrast value or lower variance value inside and/or outside of the lesion). If the contrast and variance have improved, then the newly calculated contour 1611 is maintained as the contour of the corresponding lesion. This process may then be performed with regard to the lesion 1612 as the selected lesion by then in-painting the pixels associated with lesion 1611 and the health tissue near contour 1612. In this way, each lesion is separately evaluated to generate a contour for the lesion and thereby prevent leakage of lesions into each other.

The mechanism for calculating the contours of the lesion after in-painting may be based on the Chan-Vese Segmentation algorithm which is designed to segment objects without clearly defined boundaries. This algorithm is based on level sets that are evolved iteratively to minimize an energy, which is defined by weighted values corresponding to the sum of differences intensity from the average value outside the segmented region, the sum of differences from the average value inside the segmented region, and a term which is dependent on the length of the boundary of the segmented region. Initialization is done using partitioned detection map (solve energy local minima issues).

Once the mechanism has a segmentation, the mechanism initializes the contour with previous estimates and determines whether the new contour is better, e.g., the contrast and variance of the contour are improved. If the original contour is better, then the original is maintained. If the new contour is better, e.g., the contrast and variance of the contour are improved, then the mechanism uses the new contour. In some illustrative embodiments, the mechanism determines which contour is better based on a homogenous area and computing a variance. If the variance is reduced both inside and outside of the contour, then the mechanism uses the new contour; otherwise, the mechanism uses the old contour. In another illustrative embodiment, the mechanism determines whether contrast (mean inside the contour versus mean in the vicinity of the contour) is improved. Other techniques using different measures may be used to choose between the old contour and the new contour without departing from the spirit and scope of the illustrative embodiments.

Figure 17:
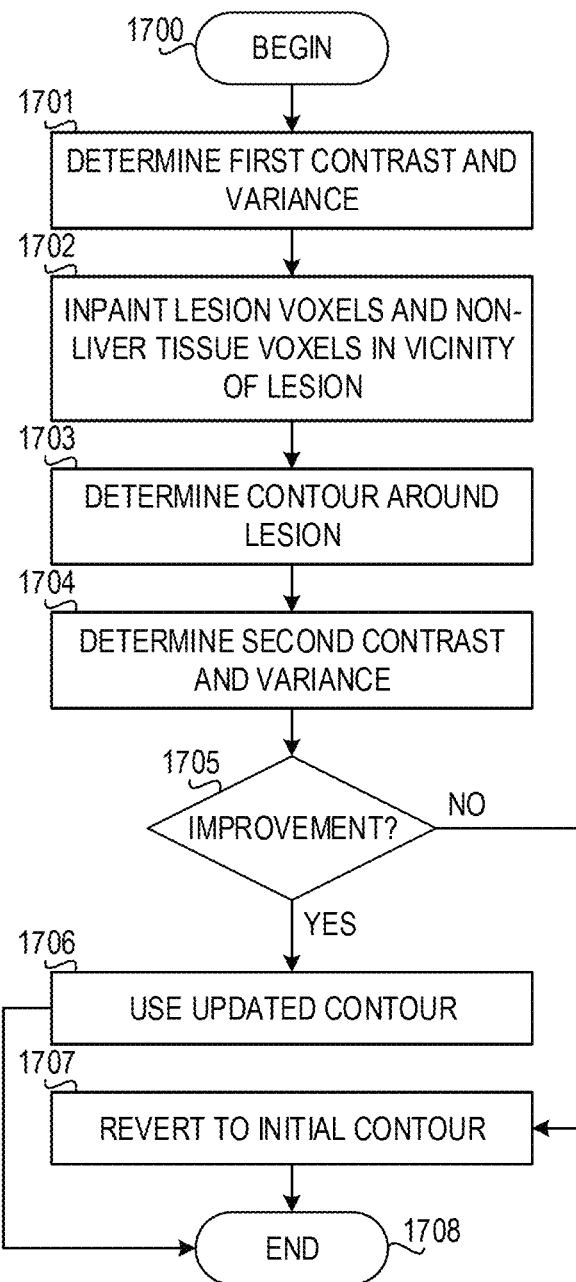
FIG. 17 is a flowchart outlining an example operation of a mechanism for slice-wise contour refinement in accordance with one illustrative embodiment.

FIG. 17 is a flowchart outlining an example operation of a mechanism for slice-wise contour refinement in accordance with an illustrative embodiment. As shown in FIG. 17, the operation begins for a given contour in an image segmented to show lesions, such as in a liver, for example (step 1700), and the mechanism determines a first contrast and variance for an initial contour (step 1701). The mechanism in-paints the lesion pixels (or voxels in three dimensions) in the vicinity of the lesion (step 1702). The mechanism then determines a contour around the lesion (step 1703). Then, the mechanism determines a second contrast and variance for the new contour (step 1704). The mechanism determines whether the second contrast and variance represent an improvement compared to the first contrast and variance (step 1705). If the second contrast and variance represent an improvement, then the mechanism uses the updated contour to represent the lesion (step 1706). Thereafter, operation ends (step 1708).

If the second contrast and variance do not represent an improvement in step 1705, then the mechanism reverts to the initial contour (step 1707). Thereafter, operation ends (step 1708). This process may be repeated for each lesion identified in the input slices and/or an input volume so as to recalculate the contours and improve the contours associated with each of the lesions present in the image/input volume.

False Positive Removal

After performing lesion segmentation to generate a list of lesions and their contours, the AI pipeline 100 performs a false positive stage of processing 150 to remove lesions from the list of lesions that are falsely indicated. This false positive stage 150 may take many forms to reduce the number of falsely identified lesions in the list of lesions, e.g., the contours and map 135 in FIG. 1 output by the liver/lesion detection logic 130 which are then merged by segmentation and relabeling performed in lesion segmentation logic 140. The following description will set forth a novel false positive removal mechanism which may be used to perform this false positive removal, but this particular false positive removal is not required. Moreover, the false positive removal mechanisms described hereafter may be used separately from the other mechanisms described above and may be applied to any listing of objects identified in images, with the illustrative embodiments utilizing such false positive removal specifically with lesions in medical images. That is, the false positive removal mechanisms described in this section may be implemented separately and distinctly from the other mechanisms described herein above.

For purposes of illustration, it will be assumed that the false positive removal mechanisms are implemented as part of the AI pipeline 100 and as part of the false positive removal logic 150 of the AI pipeline 100. Thus, in the false positive stage 150, the false positive removal mechanisms described in this section operate on the listing of lesions that results from the liver/lesion detection logic and the segmentation and relabeling of lesions, taking into account the three-dimensional nature of the input volume with the z-wise connection of lesions and contour refinement described above. This listing 148 in FIG. 1 is input to the false positive removal logic stage 150 which processes the listing 148 in the manner described hereafter and outputs a filtered or modified list of lesions, in which falsely identified lesions are minimized in the modified list of lesions, to a lesion classification stage 160. The lesion classification stage then classifies the various lesions indicated in the modified list of lesions.

That is, the capturing of all lesions in the previous stages of the AI pipeline 100 may lead to increased sensitivity settings that cause the AI pipeline 100 to mis-identify pixels that do not actually represent lesions as being part of a lesion. As a result, there may be false positives that should be removed. The false positive stage 150 comprises logic that operates on the list of lesions and their contours to remove false positives. It should be appreciated that such false positive removal must also balance the risk that, at the exam (set of input volumes level as opposed to the lesion level, removal of false positives, if not done appropriately, may result in lesions going undetected. This may be problematic because the physician and patient may not be made aware of lesions that need treatment. It should be appreciated that an exam can theoretically contain several volumes of images for the same patient. However, because in some illustrative embodiments in which there is a single phase detection implemented AI pipeline, only one volume of images is processed, it is assumed that the processing is performed with regard to a single volume. For the sake of clarity, "patient level" is used in place of "exam level" hereafter as this is what is of interest to the illustrative embodiment (does the patient have a lesion or not). It should be appreciated that in other illustrative embodiments, the operations described herein may be extended to an exam level, in which multiple volumes of images for the same patient may be evaluated.

With the illustrative embodiments, given the outputs of the prior stage of the AI pipeline 100 (slices, masks, lesions, lesion and anatomical structure contours, etc.) as inputs 148 to the false positive removal stage 150, the false positive removal stage 150 operates at a highly specific operating point at a patient level (the input volume level) in order to admit only a few patient level false positives (normal patients/volume where at least one lesion is detected). This point can be retrieved from the analysis of a patient receiver operating characteristic (ROC) (patient level sensitivity vs patient level specificity) analysis. For those volumes where using the highly specific operating point, referred to herein as the patient level operating point $OP_{patient}$, yields at least some lesions, a more sensitive operating point is used at a lesion level, referred to herein as the lesion level operating point $OP_{lesion}$. The lesion level operating point $OP_{lesion}$ can be identified from the analysis of a lesion level ROC curve (lesion sensitivity vs lesion specificity) in order to maximize the number of lesions being kept.

The two operating points, i.e. $OP_{patient}$ and $OP_{lesion}$, may be implemented in one or more trained ML/DL computer models. The one or more trained ML/DL computer models are trained to classify the input volume and/or its listing of lesions (results of the segmentation logic) as to whether the identified lesions are true lesions or false lesions, i.e. true positives or false positives. The one or more trained ML/DL computer models may be implemented as binary classifiers, where the output indicates for each lesion whether it is a true positive or a false positive. The set of outputs comprising the binary classification for all of the lesions in the input listing of lesions may be used to filter the listing of lesions to remove the false positives. In one illustrative embodiment, the one or more trained ML/DL computer models first implement the patient level operating point to determine if the results of the classification indicate any of the lesions in the listing of lesions to be true positives while filtering out false positives. If there are any true positives left in the first filtered listing of lesions after the patient level (input volume level) filtering, then the lesion level operating point is used to filter out the remaining false positives, if any. As a result, a filtered listing of lesions is generated which minimizes false positives.

The implementation of the operating points may be with regard to a single trained ML/DL computer model or multiple trained ML/DL computer models. For example, using a single trained ML/DL computer model, the operating points may be settings of operating parameters of the ML/DL computer model which may be switched dynamically. For example, the inputs to the ML/DL computer model may be processed using the patient level operating point to generate a result indicating whether or not the listing of lesions includes a true positive after classification of each of the lesions and then, if it does, the operating point of the ML/DL computer model may be switched to the lesion level operating point and the input processed again with the false positives of each pass through the ML/DL computer model being removed from the final listing of lesions output by the false positive removal stage. Alternatively, in some illustrative embodiments, two separate ML/DL computer models may be trained, one for the patient level operating point and one for the lesion level operating point, such that the results of the first ML/DL computer model indicating at least one true positive causes processing of the input through the second ML/DL computer model and the false positives identified by both models being removed from the final listing of lesions output by the false positive removal stage of the AI pipeline.

The training of the ML/DL computer model(s) may involve a machine learning training operation in which the ML/DL computer model processes training inputs comprising volumes of images and corresponding listings of lesions, where the listing of lesions includes lesion masks or contours, to generate a classification for each lesion in the image as to whether it is a true or false positive. The training input further is associated with ground truth information indicating whether the image includes a lesion or not which can then be used to evaluate the output generated by the ML/DL computer model to determine a loss or error and then modify the operating parameters of the ML/DL computer model to reduce the determined loss/error. In this way, the ML/DL computer model learns features of the input that are representative of true/false positive lesion detection. This machine learning may be performed with regard to each of the operating points, i.e. $OP_{patient}$ and $OP_{lesion}$, such that the operating parameters of the ML/DL computer model are learned taking into account the patient level sensitivity/specificity and/or lesion level sensitivity/specificity.

In classifying lesions as to whether or not they are true positives or false positives, an input volume (representing the patient at the "patient level") is considered to be positive if it contains at least one lesion. An input volume is considered to be negative if it contains no lesions. With this in mind, a true positive is defined as a positive input volume, i.e. an input volume that has at least one finding classified as a lesion that is actually a lesion. A true negative is defined as a negative input volume, i.e. an input volume that has no lesion, and where no finding has been classified as a lesion. A false positive is defined as a negative input volume in which there is no lesion, however the input indicates a lesion in the findings, i.e. the AI pipeline lists a lesion when one is not present. A false negative is defined as a positive input volume that has a lesion, but the AI pipeline does not indicate a lesion in the findings. The trained ML/DL computer model classifies lesions in the input as to whether they are true positives or false positives. False positives are filtered out of the output generated by the false positive removal. The detection of false positives is performed at different levels of sensitivity/specificity at a patient level and lesion level, i.e. the two different operating points.

The two different operating points for patient level and lesion level may be determined based on a ROC curve analysis. ROC curves may be computed using ML/DL computer model validation data composed of several input volumes (e.g., several input volumes corresponding to different patient exams) that may contain some lesions (between 0 and K lesion(s) per exam). The input to the trained ML/DL computer model(s), or "classifier(s)," are previously detected findings in the input that are either actual lesions or false positives, e.g., output of the lesion detection and segmentation stages of the AI pipeline. The first operating point, i.e. the patient level operating point $OP_{patient}$, patient, is defined to maintain at least X % of the lesions identified as true positives, meaning that almost all the true positives are kept while removing some false positives. The value of X may be set based on the analysis of the ROC curve and may be any suitable value for the particular implementation. In one illustrative embodiment, the value of X is set to 98% such that almost all of the true positives are maintained while some false positives are removed.

Figure 18A:
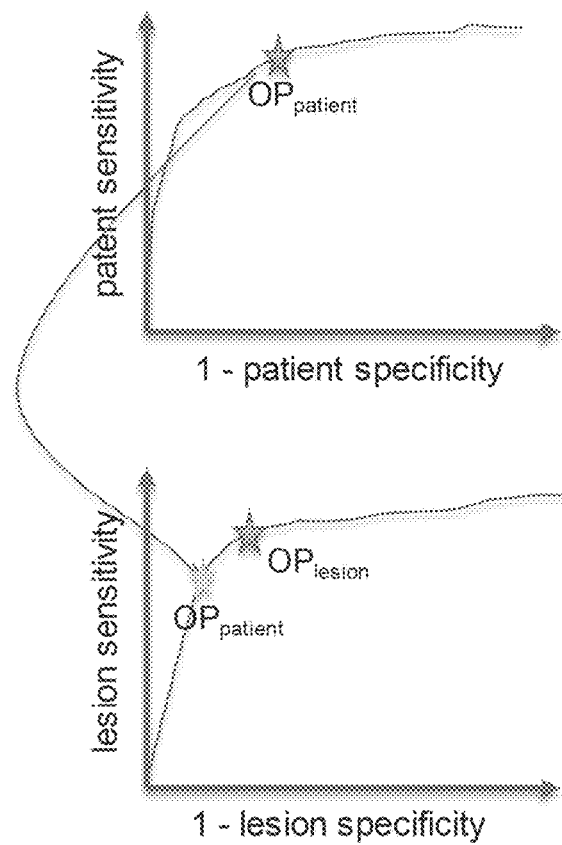
FIG. 18A is an example of ROC curves for patient level and lesion level operating point determination in accordance with one illustrative embodiment.

The second operating point, i.e. the lesion level operating point $OP_{lesion}$, is defined such that lesion sensitivity is above the lesion sensitivity obtained for the first operating point, i.e. patient level operating point $OP_{patient}$ patient, and such that the specificity is above Y %, where Y depends on the actual performance of the trained ML/DL computer model. In one illustrative embodiment, Y is set to 30%. An example of ROC curves for patient level and lesion level operating point determination is shown in FIG. 18A. As shown in FIG. 18A, the lesion level operating point is selected along the lesion level ROC curve such that the lesion sensitivity is above the lesion sensitivity for the patient level operating point.

Figure 18B:
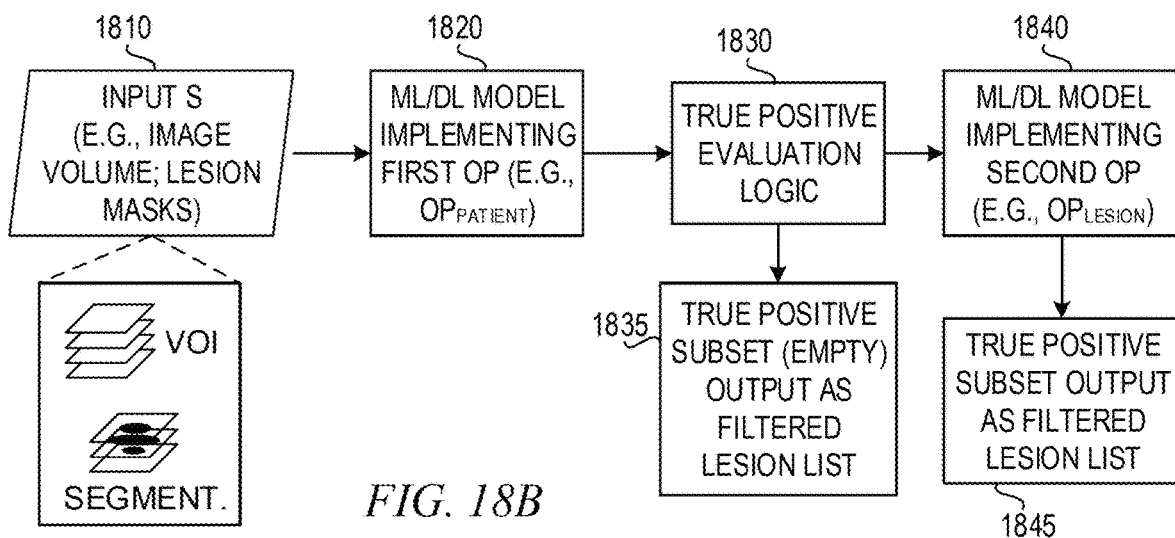
FIG. 18B is an example flow diagram of an operation for performing false positive removal based on patient and lesion level operating points in accordance with one illustrative embodiment.

FIG. 18B is an example flow diagram of an operation for performing false positive removal based on patient and lesion level operating points in accordance with one illustrative embodiment. As shown in FIG. 18B, the results of the segmentation stage logic of the AI pipeline are input 1810 to a first trained ML/DL computer model 1820 which implements the first operating point. The input 1810 includes the input volume (or volume of images (VOI)) and the listing of lesions, which includes the lesion masks or contour data specifying pixels or voxels that correspond to each of the lesions identified in the image data of the volume of images and the labels associated with these pixels specifying which lesions they correspond to three-dimensional space of the input volume, i.e. the output of the segmentation, z-wise connection, and contour refinement described previously. The input may be denoted as set S. The first trained ML/DL computer model 1820 implements the patient level operation point in its training so as to classify features extracted from the input with X %, e.g., 98%, of true positives being maintained in the resulting filtered listing of lesions generated by the classifications of the trained ML/DL computer model 1820 and some of the false positives being removed in the resulting listing. The resulting listing comprises a subset $S^+$ containing the true positive lesions classified by the first ML/DL computer model 1820 and a subset $S^-$ containing the false positive lesions classified by the first ML/DL computer model 1820.

The false positive removal logic further comprises true positive evaluation logic 1830 which determines whether the subset of true positives output by the first ML/DL computer model 1820 is empty or not. That is, the true positive evaluation logic 1830 determines if no element from S is classified as a true lesion by the first ML/DL computer model 1820. If the subset of true positives is empty, the true positive evaluation logic 1830 causes the true positive subset $S^+$ to be output as the filtered listing of lesions 1835, i.e. no lesions will be identified in the output sent to the lesion classification stage of the AI pipeline. If the true positive evaluation logic 1830 determines that the subset of true positives $S^+$ is not empty, then a second ML/DL computer model 1840 is executed on the input S, where this second ML/DL computer model 1840 implements the second operating point in its training, i.e. the lesion level operating point $OP_{lesion}$. It should be appreciated that while two ML/DL computer models 1820 and 1840 are shown for ease of explanation, as noted above, these two operating points may be implemented in different sets of trained operating parameters for configuring the same ML/DL computer model such that the second ML/DL computer model may be a processing of the input S with the same ML/DL computer model as 1820 but with different operational parameters corresponding to the second operating point.

The second ML/DL computer model 1840 processes the input with the trained operational parameters corresponding to the second operating point to again generate classifications of lesions as to whether or not they are true positives or false positives. The result is a subset $S'^+$ containing the predicted lesions (true positives) and a subset $S'^-$ containing the predicted false positives. The filtered listing of lesions 1845 is then output as the subset $S'^+$, thereby effectively eliminating the false positives specified in the subset $S'^-$.

Figure 18C:
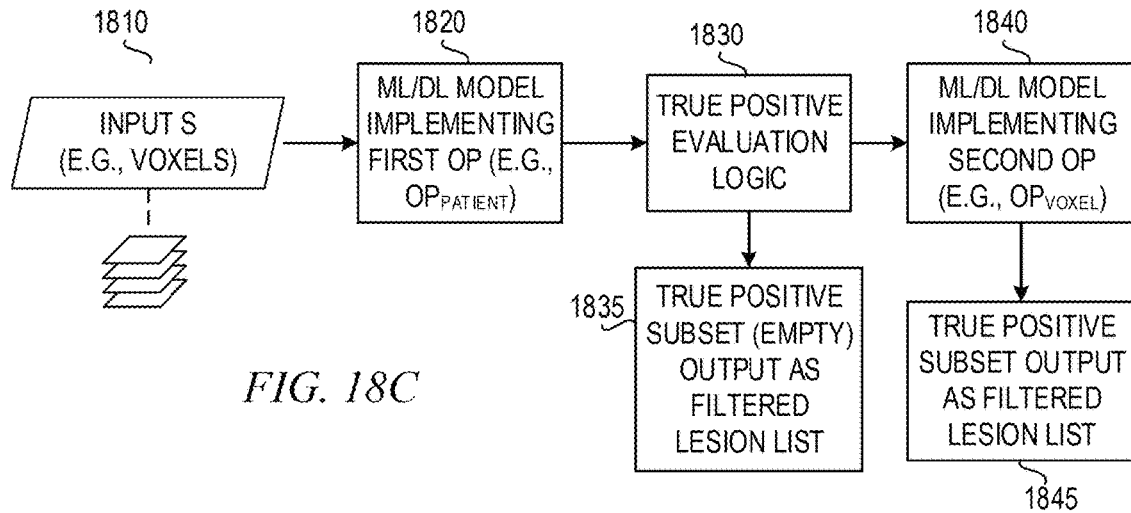
FIG. 18C is an example flow diagram of an operation for performing voxel-wise false positive removal based on input volume level and voxel level operating points in accordance with one illustrative embodiment.

The example embodiments shown in FIGS. 18A and 18B are described in terms of patient level and lesion level operating points. It should be appreciated that the mechanisms of the false positive removal may be implemented with various different levels of operating points. For example, a similar operation may be performed for image volume level and voxel level operating points in a "voxel-wise" false positive removal operation. FIG. 18C is an example flow diagram of an operation for performing voxel-wise false positive removal based on input volume level and voxel level operating points in accordance with one illustrative embodiment. The operation in FIG. 18C is similar to that of FIG. 18B but with the operations being performed with regard to voxels in the input set S. With the voxel-wise false positive removal, the first operating point may again be a patient level, or input volume level, operating point, while the second operating point may be at voxel level operating point $OP_{voxel}$. In this case, true positives and false positives are evaluated at the voxel level such that if any voxel is indicated to be associated with a lesion, and it is in fact associated with a lesion, it is a true positive, but if a voxel is indicated as being associated with a lesion and it is not in fact associated with a lesion, it is regarded as a false positive. Appropriate settings of the operating points may be generated again based on corresponding ROC curves such that similar balances between sensitivity and specificity are achieved as described above.

It should also be appreciated that while the above illustrative embodiments of the false positive removal mechanisms assume a single input volume from a patient exam, the illustrative embodiments may be applied to any grouping of one or more images (slices). For example, the false positive removal may be applied to a single slice, a set of slices smaller than an input volume, or even multiple input volumes from the same exam.

Figure 19:
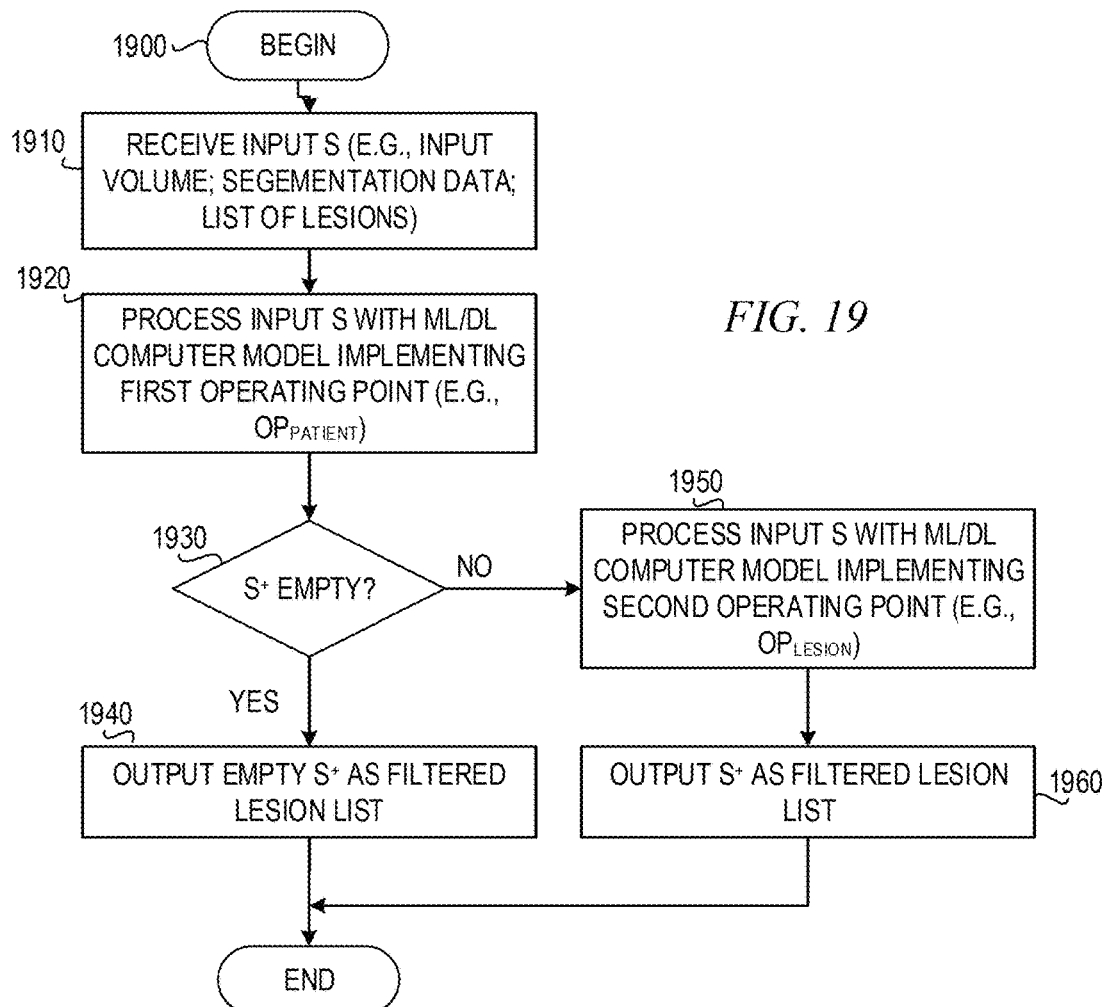
FIG. 19 is a flowchart outlining an example operation of false positive removal logic of an AI pipeline in accordance with one illustrative embodiment.

FIG. 19 is a flowchart outlining an example operation of false positive removal logic of an AI pipeline in accordance with one illustrative embodiment. As shown in FIG. 19, the operation starts (step 1900) with receiving the input S from the previous stage of the AI pipeline, where the input may include, for example, the input volume of images and the corresponding listing of lesions including masks, contours, etc. (step 1910). The input is processed by a first trained ML/DL computer model that is trained implementing a first operating point, e.g., patient level operating point that is relatively more highly specific and less sensitive, to generate a first set of classifications for lesions comprising a true positive subset and a false positive subset (step 1920). A determination is made as to whether the true positive subset is empty (step 1930). If the true positive subset is empty, then the operation outputs the true positive subset as the filtered listing of lesions (step 1940) and the operation terminates. If the true positive subset is not empty, then the input S is processed by a second ML/DL computer model that is trained implementing a second operating point that is relatively more sensitive and less specific than the first operating point (step 1950). As noted above, in some illustrative embodiments, the first and second ML/DL computer model may be the same model but configured with different operating parameters corresponding to the different training implementing the different operating points. The result of the processing of the second ML/DL computer model is a second set of classifications for lesions comprising a second true positive subset and a second false positive subset. The second true positive subset is then output as the filtered listing of lesions (step 1960) and the operation terminates.

Example Computer System Environment

Figure 20:
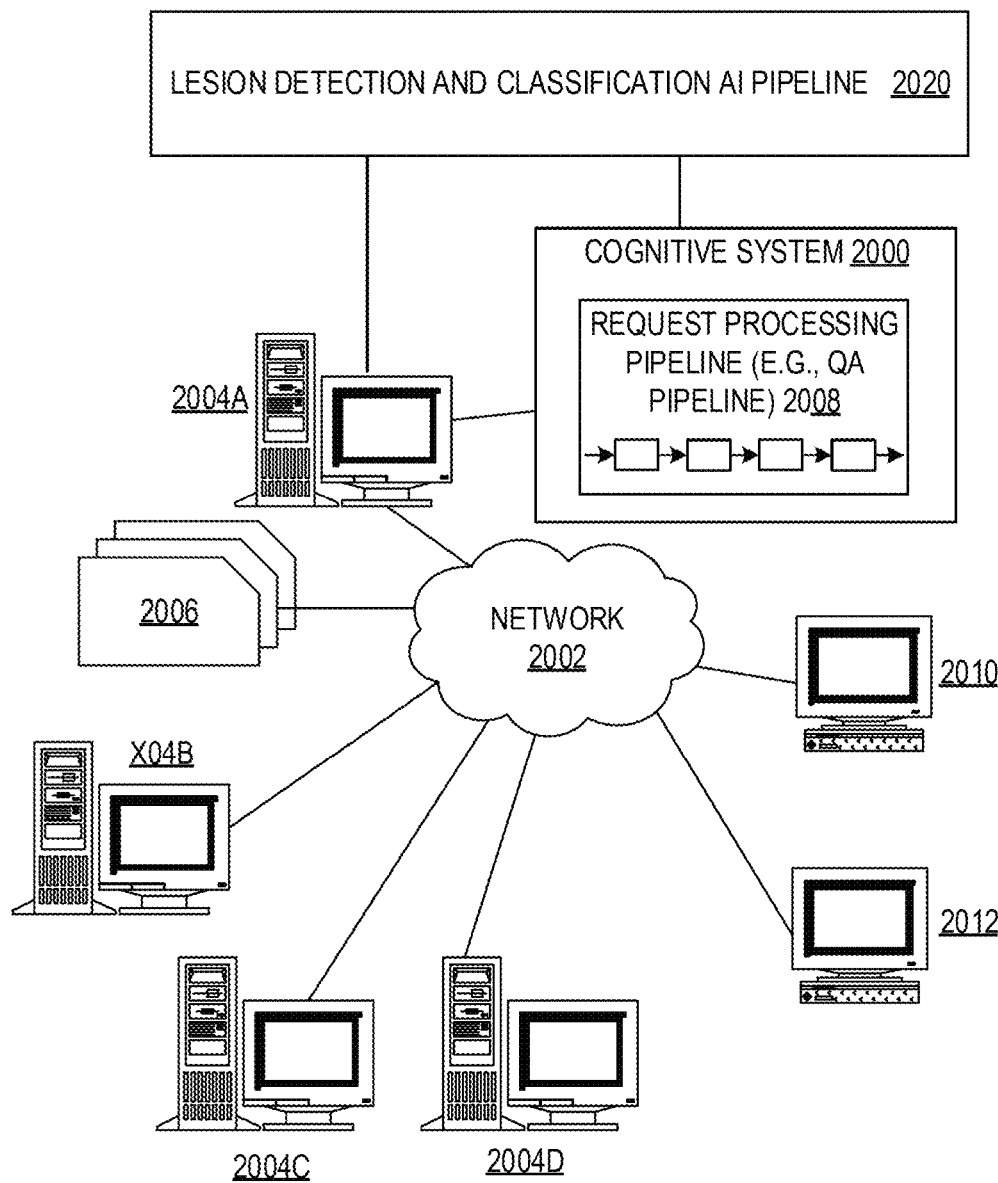
FIG. 20 is an example diagram of a distributed data processing system in which aspects of the illustrative embodiments may be implemented.
Figure 21:
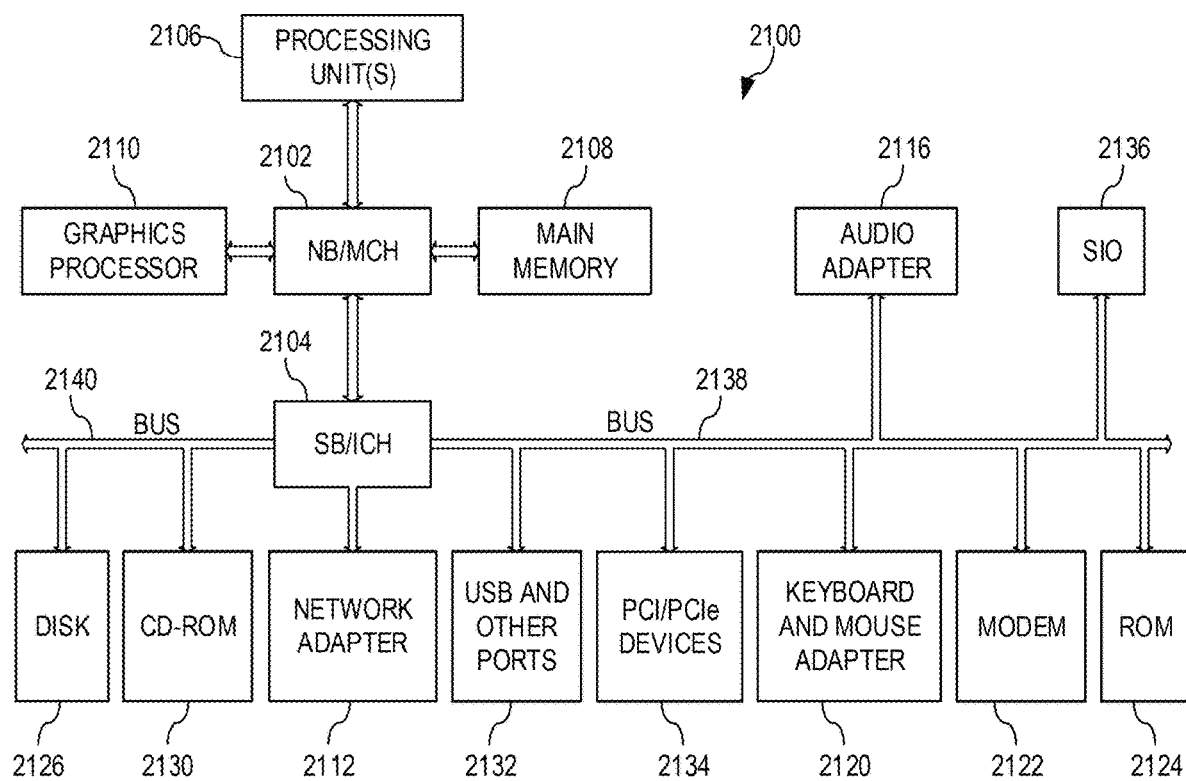
FIG. 21 is an example block diagram of a computing device in which aspects of the illustrative embodiments may be implemented.

The illustrative embodiments may be utilized in many different types of data processing environments. In order to provide a context for the description of the specific elements and functionality of the illustrative embodiments, FIGS. 20 and 21 are provided hereafter as example environments in which aspects of the illustrative embodiments may be implemented. It should be appreciated that FIGS. 20 and 21 are only examples and are not intended to assert or imply any limitation with regard to the environments in which aspects or embodiments of the present invention may be implemented. Many modifications to the depicted environments may be made without departing from the spirit and scope of the present invention.

FIG. 20 depicts a schematic diagram of one illustrative embodiment of a cognitive system 2000 implementing a request processing pipeline 2008, which in some embodiments may be a question answering (QA) pipeline, treatment recommendation pipeline, medical imaging augmentation pipeline, or any other artificial intelligence (AI) or cognitive computing based pipeline that processes a request using complex artificial intelligence mechanism that approximate human though processes with regard to a result generated, but through different computer specific processes. For purposes of the present description, it will be assumed that the request processing pipeline 2008 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety.

The cognitive system 2000 is implemented on one or more computing devices 2004A-D (comprising one or more processors and one or more memories, and potentially any other computing device elements generally known in the art including buses, storage devices, communication interfaces, and the like) connected to the computer network 2002. For purposes of illustration only, FIG. 20 depicts the cognitive system 2000 being implemented on computing device 2004A only, but as noted above the cognitive system 2000 may be distributed across multiple computing devices, such as a plurality of computing devices 2004A-D. The network 2002 includes multiple computing devices 2004A-D, which may operate as server computing devices, and 2010-2012 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 2000 and network 2002 enables question processing and answer generation (QA) functionality for one or more cognitive system users via their respective computing devices 2010-2012. In other embodiments, the cognitive system 2000 and network 2002 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 2000 may be used with components, systems, sub-systems, and/or devices other than those that are depicted herein.

The cognitive system 2000 is configured to implement a request processing pipeline 2008 that receive inputs from various sources. The requests may be posed in the form of a natural language question, natural language request for information, natural language request for the performance of a cognitive operation, or the like. For example, the cognitive system 2000 receives input from the network 2002, a corpus or corpora of electronic documents 2006, cognitive system users, and/or other data and other possible sources of input. In one embodiment, some or all of the inputs to the cognitive system 2000 are routed through the network 2002. The various computing devices 2004A-D on the network 2002 include access points for content creators and cognitive system users. Some of the computing devices 2004A-D include devices for a database storing the corpus or corpora of data 2006 (which is shown as a separate entity in FIG. 20 for illustrative purposes only). Portions of the corpus or corpora of data 2006 may also be provided on one or more other network attached storage devices, in one or more databases, or other computing devices not explicitly shown in FIG. 20. The network 2002 includes local network connections and remote connections in various embodiments, such that the cognitive system 2000 may operate in environments of any size, including local and global, e.g., the Internet.

In one embodiment, the content creator creates content in a document of the corpus or corpora of data 2006 for use as part of a corpus of data with the cognitive system 2000. The document includes any file, text, article, or source of data for use in the cognitive system 2000. Cognitive system users access the cognitive system 2000 via a network connection or an Internet connection to the network 2002, and input questions/requests to the cognitive system 2000 that are answered/processed based on the content in the corpus or corpora of data 2006. In one embodiment, the questions/ requests are formed using natural language. The cognitive system 2000 parses and interprets the question/request via a pipeline 2008, and provides a response to the cognitive system user, e.g., cognitive system user 2010, containing one or more answers to the question posed, response to the request, results of processing the request, or the like. In some embodiments, the cognitive system 2000 provides a response to users in a ranked list of candidate answers/responses while in other illustrative embodiments, the cognitive system 2000 provides a single final answer/response or a combination of a final answer/response and ranked listing of other candidate answers/responses.

The cognitive system 2000 implements the pipeline 2008 which comprises a plurality of stages for processing an input question/request based on information obtained from the corpus or corpora of data 2006. The pipeline 2008 generates answers/responses for the input question or request based on the processing of the input question/request and the corpus or corpora of data 2006.

In some illustrative embodiments, the cognitive system 2000 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 2006. Based on the application of the queries to the corpus or corpora of data 2006, a set of hypotheses, or candidate answers/responses to the input question/request, are generated by looking across the corpus or corpora of data 2006 for portions of the corpus or corpora of data 2006 (hereafter referred to simply as the corpus 2006) that have some potential for containing a valuable response to the input question/response (hereafter assumed to be an input question). The pipeline 2008 of the IBM Watson™ cognitive system then performs deep analysis on the language of the input question and the language used in each of the portions of the corpus 2006 found during the application of the queries using a variety of reasoning algorithms.

The scores obtained from the various reasoning algorithms are then weighted against a statistical model that summarizes a level of confidence that the pipeline 2008 of the IBM Watson™ cognitive system 2000, in this example, has regarding the evidence that the potential candidate answer is inferred by the question. This process is be repeated for each of the candidate answers to generate ranked listing of candidate answers which may then be presented to the user that submitted the input question, e.g., a user of client computing device 2010, or from which a final answer is selected and presented to the user. More information about the pipeline 2008 of the IBM Watson™ cognitive system 2000 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 2000 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. For example, a physician, patient, or the like may issue a request via their client computing device 2010 to the cognitive system 2000 for a particular medical imaging based operation, e.g., "identify liver lesions present in patient ABC" or "provide treatment recommendations for patient" or "identify changes in liver lesions for patient ABC", or the like. In accordance with the illustrative embodiments, such requests may be specifically directed to cognitive computer operations that employ the lesion detection and classification mechanisms of the illustrative embodiments to provide a listing of lesions, contours of lesions, classification of lesions, and contours of the anatomical structure of interest, upon which the cognitive system 2000 operates to provide a cognitive computing output. For example, the request processing pipeline 2008 may process a request such as "identify liver lesions present in patient ABC" to parse this request and thereby identify the anatomical structure of interest to be the "liver", the particular input volume being a medical imaging volume for patient "ABC", and that "lesions" in the anatomical structure are to be identified. Based on this parsing, the particular medical imaging volume corresponding to patient "ABC" may be retrieved from the corpus 2006 and input to the lesion detection and classification AI pipeline 2020 which operates on this input volume as previously described above so as to identify the listing of liver lesions which is output to the cognitive computing system 2000 for further evaluation through the request processing pipeline 2008, for generating a medical imaging viewer application output, or the like.

As shown in FIG. 20, one or more of the computing devices, e.g., server 2004, may be specifically configured to implement the lesion detection and classification AI pipeline 2020, such as the AI pipeline 100 in FIG. 1, for example. The configuring of the computing device may comprise the providing of application specific hardware, firmware, or the like to facilitate the performance of the operations and generation of the outputs described herein with regard to the illustrative embodiments. The configuring of the computing device may also, or alternatively, comprise the providing of software applications stored in one or more storage devices and loaded into memory of a computing device, such as server 2004, for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of the illustrative embodiments and is not a general purpose computing device. Moreover, as described herein, the implementation of the mechanisms of the illustrative embodiments improves the functionality of the computing device and provides a useful and concrete result that facilitates automatic lesion detection in an anatomical structure of interest, as well as classification of such lesions, which reduces error and improves efficiency relative to manual processes.

As noted above, the mechanisms of the illustrative embodiments utilize specifically configured computing devices, or data processing systems, to perform the operations for performing anatomical structure identification, lesion detection and classification. These computing devices, or data processing systems, may comprise various hardware elements which are specifically configured, either through hardware configuration, software configuration, or a combination of hardware and software configuration, to implement one or more of the systems/subsystems described herein. FIG. 21 is a block diagram of just one example data processing system in which aspects of the illustrative embodiments may be implemented. Data processing system 2100 is an example of a computer, such as server 2004 in FIG. 20, in which computer usable code or instructions implementing the processes and aspects of the illustrative embodiments of the present invention may be located and/or executed so as to achieve the operation, output, and external effects of the illustrative embodiments as described herein.

In the depicted example, data processing system 2100 employs a hub architecture including north bridge and memory controller hub (NB/MCH) 2102 and south bridge and input/output (I/O) controller hub (SB/ICH) 2104. Processing unit 2106, main memory 2108, and graphics processor 2110 are connected to NB/MCH 2102. Graphics processor 2110 may be connected to NB/MCH 2102 through an accelerated graphics port (AGP).

In the depicted example, local area network (LAN) adapter 2112 connects to SB/ICH 2104. Audio adapter 2116, keyboard and mouse adapter 2120, modem 2122, read only memory (ROM) 2124, hard disk drive (HDD) 2126, CD-ROM drive 2130, universal serial bus (USB) ports and other communication ports 2132, and PCI/PCIe devices 2134 connect to SB/ICH 2104 through bus 2138 and bus 2140. PCI/PCIe devices may include, for example, Ethernet adapters, add-in cards, and PC cards for notebook computers. PCI uses a card bus controller, while PCIe does not. ROM 2124 may be, for example, a flash basic input/output system (BIOS).

HDD 2126 and CD-ROM drive 2130 connect to SB/ICH 2104 through bus 2140. HDD 2126 and CD-ROM drive 2130 may use, for example, an integrated drive electronics (IDE) or serial advanced technology attachment (SATA) interface. Super I/O (SIO) device 2136 may be connected to SB/ICH 2104.

An operating system runs on processing unit 2106. The operating system coordinates and provides control of various components within the data processing system 2100 in FIG. 21. As a client, the operating system may be a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 2100 may be, for example, an IBM eServer™ System P® computer system, Power™ processor based computer system, or the like, running the Advanced Interactive Executive (AIX) operating system or the LINUX® operating system. Data processing system 2100 may be a symmetric multiprocessor (SMP) system including a plurality of processors in processing unit 2106. Alternatively, a single processor system may be employed.

Instructions for the operating system, the object-oriented programming system, and applications or programs are located on storage devices, such as HDD 2126, and may be loaded into main memory 2108 for execution by processing unit 2106. The processes for illustrative embodiments of the present invention may be performed by processing unit 2106 using computer usable program code, which may be located in a memory such as, for example, main memory 2108, ROM 2124, or in one or more peripheral devices 2126 and 2130, for example.

A bus system, such as bus 2138 or bus 2140 as shown in FIG. 21, may be comprised of one or more buses. Of course, the bus system may be implemented using any type of communication fabric or architecture that provides for a transfer of data between different components or devices attached to the fabric or architecture. A communication unit, such as modem 2122 or network adapter 2112 of FIG. 21, may include one or more devices used to transmit and receive data. A memory may be, for example, main memory 2108, ROM 2124, or a cache such as found in NB/MCH 2102 in FIG. 21.

As mentioned above, in some illustrative embodiments the mechanisms of the illustrative embodiments may be implemented as application specific hardware, firmware, or the like, application software stored in a storage device, such as HDD 2126 and loaded into memory, such as main memory 2108, for executed by one or more hardware processors, such as processing unit 2106, or the like. As such, the computing device shown in FIG. 21 becomes specifically configured to implement the mechanisms of the illustrative embodiments and specifically configured to perform the operations and generate the outputs described herein with regard to the lesion detection and classification artificial intelligence pipeline.

Those of ordinary skill in the art will appreciate that the hardware in FIGS. 20 and 21 may vary depending on the implementation. Other internal hardware or peripheral devices, such as flash memory, equivalent non-volatile memory, or optical disk drives and the like, may be used in addition to or in place of the hardware depicted in FIGS. 20 and 21. Also, the processes of the illustrative embodiments may be applied to a multiprocessor data processing system, other than the SMP system mentioned previously, without departing from the spirit and scope of the present invention.

Moreover, the data processing system 2100 may take the form of any of a number of different data processing systems including client computing devices, server computing devices, a tablet computer, laptop computer, telephone or other communication device, a personal digital assistant (PDA), or the like. In some illustrative examples, data processing system 2100 may be a portable computing device that is configured with flash memory to provide non-volatile memory for storing operating system files and/or user-generated data, for example. Essentially, data processing system 2100 may be any known or later developed data processing system without architectural limitation.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to implement a false positive removal engine for removing falsely identified objects in a listing of objects input data set, the method comprising:

receiving, by the false positive removal engine, a received input comprising a listing of detected objects in one or more images of an input volume of images;

configuring, by the false positive removal engine, at least one machine learning classifier computer model, by executing a first machine learning training operation, using a compilation of image volume data, to classify objects as to whether they are true positive object detections, based on first operational parameters to implement a first operating point for the at least one machine learning classifier computer model, and thereby generate a first operating point configured model;

configuring, by the false positive removal engine, the at least one machine learning classifier computer model, by executing a second machine learning training operation, using the compilation of image volume data, based on second operational parameters to implement a second operating point, different from the first operating point, for the at least one machine learning classifier computer model, and thereby generate a second operating point configured model;

processing, by the first operating point configured model, the received input to classify each detected object in the listing of objects as to whether or not the detected object is a true positive or a false positive to thereby generate a first set of detected objects classified as true positive;

determining, by logic of the false positive removal engine, whether the first set is empty;

in response to the first set being empty, outputting, by the false positive removal engine, the first set as a filtered list of objects; and in response to the first set not being empty, processing, by the second operating point configured model, the received input to classify each detected object in the listing of objects as to whether or not the detected object is a true positive or a false positive to thereby generate a second set of detected objects classified as true positive and outputting, by the false positive removal engine, the second set of detected objects as the filtered list of objects.

2. The method of claim 1, wherein the first operating point is a group level operating point that has a relatively higher specificity than the second operating point, and wherein the first set of operational parameters are operational parameters optimized to minimize group level false positives generated by the at least one machine learning classifier computer model.

3. The method of claim 1, wherein the second operating point is an element level operating point that has a relatively higher sensitivity than the first operating point, and wherein the second set of operational parameters are operational parameters optimized to increase a number of element level true positives generated by the at least one machine learning classifier computer model.

4. The method of claim 1, wherein the first operating point is selected by analyzing a group level receiver operating characteristic (ROC) curve plotting group level object detection sensitivity versus group level object detection specificity, to select a point along the group level ROC curve in which a pairing of object detection sensitivity and object detection specificity results in a predetermined percentage of true positive object detections being maintained in the first set of detected objects.

5. The method of claim 1, wherein the second operating point is selected by analyzing an element level receiver operating characteristic (ROC) curve plotting object detection sensitivity versus object detection specificity, to select a point along the element level ROC curve having an object detection sensitivity that is higher than an object detection sensitivity corresponding to the first operating point, and provides at least a predetermined level of object detection specificity corresponding to a performance of the at least one machine learning classifier computer model.

6. The method of claim 1, wherein the at least one machine learning classifier computer model comprises a first machine learning classifier computer model and a second machine learning classifier computer model, and wherein configuring at least one machine learning classifier computer model with first operational parameters to implement a first operating point comprises performing machine learning training of the first machine learning classifier computer model based on the first operating point, and wherein configuring at least one machine learning classifier computer model with second operational parameters to implement a second operating point comprises performing machine learning training of the second machine learning classifier computer model based on the second operation point.

7. The method of claim 1, wherein the objects are lesions, and wherein the false positive removal engine is a stage of computer logic in a lesion detection and classification artificial intelligence (AI) pipeline comprising a plurality of trained machine learning computer models, and wherein the received input is received from a lesion segmentation logic stage of the AI pipeline that implements an ensemble of at least one trained machine learning computer model that generates the listing of objects.

8. The method of claim 7, wherein the plurality of trained machine learning computer models of the AI pipeline comprises:
one or more first machine learning computer models of the AI pipeline that process an input volume of medical images to detect lesions present in the medical images of the input volume which correspond to an anatomical structure of interest; and
one or more second machine learning computer models of the AI pipeline that processes the detected lesions to perform lesion segmentation and combining of lesion contours of different images in the input medical image associated with a same lesion, to generate the listing of lesions and corresponding lesion contours.

9. The method of claim 7, wherein the plurality of trained machine learning computer models comprise one or more machine learning computer models that process the filtered listing of lesions output by the false positive removal engine to classify the lesions in the listing of lesions into one or more predetermined classes of lesions corresponding to the anatomical structure of interest.

10. The method of claim 8, wherein the anatomical structure of interest is a human liver.

11. A computer program product comprising a computer readable storage medium having a computer readable program stored therein, wherein the computer readable program, when executed on a computing device, causes the computing device to implement a false positive removal engine for removing falsely identified objects in a listing of objects input data set, and to:
receive, by the false positive removal engine, a received input comprising a listing of detected objects in one or more images of an input volume of images;
configure, by the false positive removal engine, at least one machine learning classifier computer model, by executing a first machine learning training operation, using a compilation of image volume data, to classify objects as to whether they are true positive object detections, based on first operational parameters to implement a first operating point for the at least one machine learning classifier computer model, and thereby generate a first operating point configured model;
configure, by the false positive removal engine, the at least one machine learning classifier computer model, by executing a second machine learning training operation, using the compilation of image volume data, based on second operational parameters to implement a second operating point, different from the first operating point, for the at least one machine learning classifier computer model, and thereby generate a second operating point configured model;
process, by the first operating point configured model, the received input to classify each detected object in the listing of objects as to whether or not the detected object is a true positive or a false positive to thereby generate a first set of detected objects classified as true positive;
determine, by logic of the false positive removal engine, whether the first set is empty;
in response to the first set being empty, outputting, by the false positive removal engine, the first set as a filtered list of objects; and
in response to the first set not being empty, process, by the second operating point configured model, the received input to classify each detected object in the listing of objects as to whether or not the detected object is a true positive or a false positive to thereby generate a second set of detected objects classified as true positive and outputting, by the false positive removal engine, the second set of detected objects as the filtered list of objects.

12. The computer program product of claim 11, wherein the first operating point is a group level operating point that has a relatively higher specificity than the second operating point, and wherein the first set of operational parameters are operational parameters optimized to minimize group level false positives generated by the at least one machine learning classifier computer model.

13. The computer program product of claim 11, wherein the second operating point is an element level operating point that has a relatively higher sensitivity than the first operating point, and wherein the second set of operational parameters are operational parameters optimized to increase a number of element level true positives generated by the at least one machine learning classifier computer model.

14. The computer program product of claim 11, wherein the first operating point is selected by analyzing a group level receiver operating characteristic (ROC) curve plotting group level object detection sensitivity versus group level object detection specificity, to select a point along the group level ROC curve in which a pairing of object detection sensitivity and object detection specificity results in a predetermined percentage of true positive object detections being maintained in the first set of detected objects.

15. The computer program product of claim 11, wherein the second operating point is selected by analyzing an element level receiver operating characteristic (ROC) curve plotting object detection sensitivity versus object detection specificity, to select a point along the element level ROC curve having an object detection sensitivity that is higher than an object detection sensitivity corresponding to the first operating point, and provides at least a predetermined level of object detection specificity corresponding to a performance of the at least one machine learning classifier computer model.

16. The computer program product of claim 11, wherein the at least one machine learning classifier computer model comprises a first machine learning classifier computer model and a second machine learning classifier computer model, and wherein configuring at least one machine learning classifier computer model with first operational parameters to implement a first operating point comprises performing machine learning training of the first machine learning classifier computer model based on the first operating point, and wherein configuring at least one machine learning classifier computer model with second operational parameters to implement a second operating point comprises performing machine learning training of the second machine learning classifier computer model based on the second operation point.

17. The computer program product of claim 11, wherein the objects are lesions, and wherein the false positive removal engine is a stage of computer logic in a lesion detection and classification artificial intelligence (AI) pipeline comprising a plurality of trained machine learning computer models, and wherein the received input is received from a lesion segmentation logic stage of the AI pipeline that implements an ensemble of at least one trained machine learning computer model that generates the listing of objects.

18. The computer program product of claim 17, wherein the plurality of trained machine learning computer models of the AI pipeline comprises:
   one or more first machine learning computer models of the AI pipeline that process an input volume of medical images to detect lesions present in the medical images of the input volume which correspond to an anatomical structure of interest; and
   one or more second machine learning computer models of the AI pipeline that processes the detected lesions to perform lesion segmentation and combining of lesion contours of different images in the input medical image associated with a same lesion, to generate the listing of lesions and corresponding lesion contours.

19. The computer program product of claim 17, wherein the plurality of trained machine learning computer models comprise one or more machine learning computer models that process the filtered listing of lesions output by the false positive removal engine to classify the lesions in the listing of lesions into one or more predetermined classes of lesions corresponding to the anatomical structure of interest.

20. An apparatus comprising:
   a processor; and
   a memory coupled to the processor, wherein the memory comprises instructions which, when executed by the processor, cause the processor to implement a false positive removal engine for removing falsely identified objects in a listing of objects input data set, and to:
   receive, by the false positive removal engine, a received input comprising a listing of detected objects in one or more images of an input volume of images;
   configure, by the false positive removal engine, at least one machine learning classifier computer model, by executing a first machine learning training operation, using a compilation of image volume data, to classify objects as to whether they are true positive object detections, based on first operational parameters to implement a first operating point for the at least one machine learning classifier computer model, and thereby generate a first operating point configured model;
   configure, by the false positive removal engine, the at least one machine learning classifier computer model, by executing a second machine learning training operation, using the compilation of image volume data, based on second operational parameters to implement a second operating point, different from the first operating point, for the at least one machine learning classifier computer model, and thereby generate a second operating point configured model;
   process, by the first operating point configured model, the received input to classify each detected object in the listing of objects as to whether or not the detected object is a true positive or a false positive to thereby generate a first set of detected objects classified as true positive;
   determine, by logic of the false positive removal engine, whether the first set is empty;
   in response to the first set being empty, outputting, by the false positive removal engine, the first set as a filtered list of objects; and
   in response to the first set not being empty, process, by the second operating point configured model, the received input to classify each detected object in the listing of objects as to whether or not the detected object is a true positive or a false positive to thereby generate a second set of detected objects classified as true positive and outputting, by the false positive removal engine, the second set of detected objects as the filtered list of objects.

* * * * *